United States Patent [19]
Horwell et al.

[11] Patent Number: 5,981,755
[45] Date of Patent: Nov. 9, 1999

[54] TACHYKININ ANTAGONISTS

[75] Inventors: David Christopher Horwell, Foxton; William Howson, Weston Colville; Martyn Clive Pritchard, St. Ives; Edward Roberts, Newmarket; David Charles Rees, Glasgow, all of United Kingdom

[73] Assignee: Warner-Lambert Company, Morris Plains, N.J.

[21] Appl. No.: 09/168,512

[22] Filed: Oct. 8, 1998

Related U.S. Application Data

[62] Division of application No. 08/953,037, Oct. 17, 1993, Pat. No. 5,856,354, which is a division of application No. 08/727,067, Oct. 8, 1996, Pat. No. 5,716,979, which is a division of application No. 08/344,064, Nov. 29, 1994, Pat. No. 5,594,022, and a continuation-in-part of application No. 08/097,264, Jul. 23, 1993, abandoned, and a continuation-in-part of application No. 07/930,252, Aug. 13, 1992, abandoned.

[51] Int. Cl.[6] ...................... C07D 209/04; C07D 209/18; C07D 209/20; C07D 405/06
[52] U.S. Cl. ...................... 546/277.4; 548/491; 548/496; 549/29; 549/49; 549/56; 549/58; 549/59; 549/429; 549/462
[58] Field of Search .............................. 424/9.1; 548/491, 548/496; 546/277.4

[56] References Cited

FOREIGN PATENT DOCUMENTS

| | | |
|---|---|---|
| 394989A3 | 10/1990 | European Pat. Off. . |
| 428434A3 | 5/1991 | European Pat. Off. . |
| 443132A1 | 8/1991 | European Pat. Off. . |
| 93/01160 | 1/1993 | WIPO . |
| 93/01165 | 1/1993 | WIPO . |
| 93/01169 | 1/1993 | WIPO . |
| 93/18023 | 9/1993 | WIPO . |

OTHER PUBLICATIONS

*Physiological Reviews*, 67(4):1117–1142 (1987), S. Nakanishi, "Substance P Precursor and Kininogen . . . ".
*Neurochem. Int.*, 18(2):149–165 (1991), S. Guard et al. "Tachykinin Receptor Types, Classification and . . . ".
*Annu. Rev. Neurosci.*, 14:123–136 (1991), S. Nakanishi, "Mammalian Tachykinin Receptors".
*Pharmacological Reviews*, 35(2):85–141 (1983), B. Pernow, "Substance P".
*Current Opinion in Therapeutic Patents*, 1:197 (1991), B. E. Tomczuk et al..
*Science*, 251:435–437 (1991), R. M. Snider et al., "A Potent Nonpeptide Antagonist of the Substance P . . . ".
*Proc. Natl. Acad. Sci.*, 88:10208–10212 (1991), C. Garret et al., "Pharmacological properties of potent . . . ".
*Brit. J. Pharmacol.*, 105:78 (1992), N. Watson et al., "Demonstration of a Facilitatory Role of . . . ".
*Neuropeptides*, 22:24 (1992), T. Fujii et al., "Effect of Novel Substance P Antagonsit, FK888, on Airway...".
Tomczuk, B.E. et al. *Current Opinions in Therapeutic Patents* 1991;1:197.

*Primary Examiner*—Johann Richter
*Assistant Examiner*—Jane C. Osweki
*Attorney, Agent, or Firm*—Elizabeth M. Anderson

[57] ABSTRACT

The invention concerns tachykinin antagonists. The compounds are nonpeptides which have utility in treating disorders mediated by tachykinins. Such disorders are respiratory, inflammatory, gastrointestinal, ophthalmic, allergies, pain, vascular, diseases of the central nervous system, and migraine. Methods of preparing compounds and novel intermediates are also included. The compounds are expected to be especially useful in asthma and rheumatoid arthritis.

2 Claims, No Drawings

TACHYKININ ANTAGONISTS

CROSS-REFERENCE TO RELATED APPLICATION

This application is a divisional of U.S. patent application Ser. No. 08/953,037 filed Oct. 17, 1997, now U.S. Pat. No. 5,856,354 which is a divisional of U.S. patent application Ser. No. 08/727,067 filed Oct. 8, 1996, now U.S. Pat. No. 5,716,979; which is a divisional of U.S. patent application Ser. No. 08/344,064 filed Nov. 29, 1994, now U.S. Pat. No. 5,594,022; and is a continuation-in-part of U.S. patent application Ser. No. 08/097,264, filed Jul. 23, 1993, now abandoned; and is a continuation-in-part of U.S. application Ser. No. 07/930,252, filed Aug. 13, 1992, now abandoned.

BACKGROUND OF THE INVENTION

Over the last decade, major advances have been made in the understanding of the biology of the mammalian tachykinin neuropeptides. It is now well established that substance-P (1), neurokinin A (NKA) (2), and neurokinin B (NKB) (3), all of which share a common C-terminal sequence Phe-X-Gly-Leu-Met-$NH_2$, (Nakanishi S, *Physiol Rev* 1987;67:117), are widely distributed throughout the periphery and central nervous system (CNS) where they appear to interact with at least three receptor types referred to as $NK_1$, $NK_2$, and $NK_3$, (Guard S, et al., *Neurosci Int* 1991;18:149). Substance-P displays highest affinity for $NK_1$ receptors, whereas NKA and NKB bind preferentially to $NK_2$ and $NK_3$ receptors, respectively. Recently, all three receptors have been cloned and sequenced and shown to be members of the G-protein-linked "super family" of receptors (Nakanishi S, *Annu Rev Neurosci* 1991;14:123). A wealth of evidence supports the involvement of tachykinin neuropeptides in a variety of biological activities including pain transmission, vasodilation, smooth muscle contraction, bronchoconstriction, activation of the immune system (inflammatory pain), and neurogenic inflammation (Pernow B, *Pharmacol Rev* 1983;35:85). However, to date, a detailed understanding of the physiological roles of tachykinin neuropeptides has been severely hampered by a lack of selective, high affinity, metabolically stable tachykinin receptor antagonists that possess both good bioavailability and CNS penetration. Although several tachykinin receptor antagonists have been described (Tomczuk B E, et al., *Current Opinions in Therapeutic Patents* 1991;1:197), most have been developed through the modification and/or deletion of one or more of the amino acids that comprise the endogenous mammalian tachykinins such that the resulting molecules are still peptides that possess poor pharmacokinetic properties and limited in vivo activities.

However, since 1991, a number of high-affinity nonpeptide antagonists have been reported. Snider R M, et al, (*Science* 1991;251:435), and Garret C, et. al, (*Proc Natl Acad Sci* 1991;88:10208), described CP-96,345 and RP 67580, respectively, as antagonists at the $NK_1$ receptor, while Advenier C, et al., (*Brit J Pharmacol* 1992;105:78), presented data on SR 48969 showing its high affinity and selectivity for $NK_2$ receptors. It is of interest that most of the nonpeptide tachykinin receptor antagonists described to date arose, either directly or indirectly, out of the screening of large compound collections using a robust radioligand binding assay as the primary screen. Recently, FK 888, a "dipeptide" with high affinity for the $NK_1$ receptor was described (Fujii J, et al., *Neuropeptide* 1992;22:24).

International Publication Numbers WO 93/01169, WO 93/01165, and WO 93/001160 cover certain nonpeptide tachykinin receptor antagonists.

Substance-P is widely distributed throughout the periphery and central nervous system. It is believed to mediate a variety of biological actions, via an interaction with three receptor types referred to as $NK_1$, $NK_2$, and $NK_3$, including smooth muscle contraction, pain transmission, neuronal excitation, secretion of saliva, angiogenesis, bronchoconstriction, activation of the immune system and neurogenic inflammation.

Accordingly, compounds capable of antagonizing the effects of substance-P at $NK_1$ receptors will be useful in treating or preventing a variety of brain disorders including pain, anxiety, panic, depression, schizophrenia, neuralgia, and addiction disorders; inflammatory diseases such as arthritis, asthma, and psoriasis; gastrointestinal disorders including colitis, Crohn's disease, irritable bowel syndrome, and satiety; allergic responses such as eczema and rhinitis; vascular disorders such as angina and migraine; neuropathological disorders including Parkinson's disease, multiple sclerosis, and Alzheimer's disease; and ophthalmic diseases including scleroderma.

The compounds of the invention, $NK_1$ receptor antagonists, are useful as anti-angiogenic agents for the treatment of conditions associated with aberrant neovascularization such as rheumatoid arthritis, atherosclerosis, and tumor cell growth. They will also be useful as agents for imaging $NK_1$ receptors in vivo in conditions such as ulcerative colitis and Crohn's disease.

SUMMARY OF THE INVENTION

The invention covers tachykinin antagonists. The compounds are nonpeptides which have proved to be highly selective and functional tachykinin antagonists. These compounds are unique in the alkylation/substitution pattern along their back bone.

Compounds of the invention are those of formula

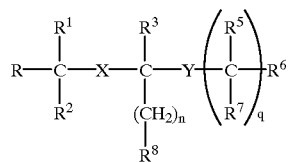

I or a pharmaceutically acceptable salt thereof wherein
R is phenyl,
  pyridine,
  thiophene,
  furan,
  naphthalene,
  indole,
  benzofuran, or
  benzothiophene each unsubstituted,
  mono-, di-, or trisubstituted by
    alkyl,
    hydroxy,
    alkoxy,
    $NO_2$,
    halogen,
    $NH_2$, or
    $CF_3$;
$R^1$ and $R^2$ are each independently hydrogen or alkyl of from 1 to 4 atoms;
R and $R^2$, when joined by a bond, can form a ring;

X is

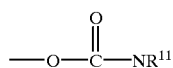

wherein $R^{11}$ is hydrogen or alkyl of from 1 to 3 carbon atoms;
$R^3$ is hydrogen or $(CH_2)_m R^{13}$ where m is an integer of from 1 to 6 and $R^{13}$ is H, CN, $NH_2$, $N(CH_3)_2$, or $NHCOCH_3$;
n is an integer of from 1 to 2;
$R^8$ is phenyl,
  pyridine,
  thiophene,
  furan,
  naphthalene,
  indole,
  benzofuran, or
  benzothiophene each unsubstituted, or
  mono-, di-, or trisubstituted by
    alkyl,
    hydroxy,
    alkoxy,
    $NO_2$,
    halogen,
    $NH_2$, or
    $CF_3$;
Y is

wherein $R^4$ is hydrogen or alkyl of from 1 to 3 carbon atoms,
—$CO_2$—,
—$COCH_2$—,
—$CH_2O$—,
—$CH_2NH$—,
—CH=CH—,
—$CH_2CH_2$—,
—$CHOHCH_2$—,

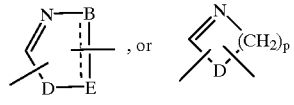

wherein B is nitrogen, CH, $CH_2$, oxygen, or sulfur, D is; nitrogen, oxygen, or sulfur, E is nitrogen or CH, $CH_2$, p is an integer of from 3 to 4, and the dotted lines indicates a double or single bond;
$R^5$ and $R^7$ are each independently hydrogen or alkyl of from 1 to 4 carbon atoms;
q is an integer of from 0 to 1; and
$R^6$ is phenyl,
  pyridine,
  thiophene,
  furan,
  naphthalene,
  indole,
  benzofuran, or
  benzothiophene each unsubstituted, or
  mono-, di-, or trisubstituted by
    alkyl,
    hydroxy,
    alkoxy,
    halogen,
    $NH_2$, or
    $CF_3$;
straight alkyl of from 1 to 8 carbons, branched alkyl of from 3 to 8 carbons, cycloalkyl of from 5 to 8 carbons, or heterocycloalkyl.

Other cyclic derivatives of Formula I are contemplated such as would occur to one skilled in the art.

Prodrugs of the above are also contemplated such as would occur to one skilled in the art, see Bundgaard, et al., *Acta Pharm Suec*, 1987;24:23:1–246. For example, where a suitable moiety has been attached to the linker X or Y or the indole N.

Preferred compounds of the invention are those of Formula I above wherein
R is pyridine,
  thiophene,
  furan,
  naphthalene,
  indole,
  benzofuran, or
  benzothiophene each unsubstituted,
  mono-, di-, or trisubstituted by
    alkyl,
    hydroxy,
    alkoxy,
    halogen,
    $NH_2$, or
    $CF_3$;
$R^1$ and $R^2$ are each independently hydrogen or alkyl of from 1 to 4 atoms;
R and $R^2$, when joined by a bond, can form a ring;
X is

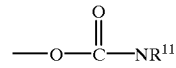

wherein $R^{11}$ is hydrogen or alkyl of from 1 to 3 carbon atoms;
$R^3$ is hydrogen or $(CH_2)_m R^{13}$ where m is an integer of from 1 to 6 and $R^{13}$ is H, CN, $NH_2$, $N(CH_3)_2$, or $NHCOCH_3$;
n is an integer of from 1 to 2;
$R^8$ is phenyl,
  pyridine,
  thiophene,
  furan,
  naphthalene,
  indole,
  benzofuran, or
  benzothiophene each unsubstituted, or
  mono-, di-, or trisubstituted by
    alkyl,
    hydroxy,
    alkoxy,
    halogen,
    $NH_2$, or
    $CF_3$;

Y is

wherein $R^4$ is hydrogen or alkyl of from 1 to 3 carbon atoms,
—$CO_2$—,
—$COCH_2$—,
—$CH_2O$—,
—$CH_2NH$—,
—CH=CH—,
—$CH_2CH_2$—,
—$CHOHCH_2$—,

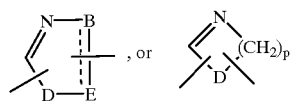

wherein B is nitrogen, CH, $CH_2$, oxygen, or sulfur, D is nitrogen, oxygen, or sulfur, E is nitrogen, CH, $CH_2$, p is an integer of from 3 to 4, and the dotted line indicates a double or single bond;
$R^5$ and $R^7$ are each independently hydrogen or alkyl of from 1 to 4 carbon atoms;
q is an integer of from 0 to 1; and
$R^6$ is phenyl,
pyridine,
thiophene,
furan,
naphthalene,
indole,
benzofuran, or
benzothiophene each unsubstituted, or
mono-, di-, or trisubstituted by
alkyl,
hydroxy,
alkoxy,
$NO_2$,
halogen,
$NH_2$, or
$CF_3$;
straight alkyl of from 1 to 8 carbons, branched alkyl of from 3 to 8 carbons, cycloalkyl of from 5 to 8 carbons, or heterocycloalkyl;
More preferred compounds of the invention are those of Formula I above wherein
R is phenyl
pyridyl,
thiophene,
furan,
naphthalene,
indole each unsubstituted, or
mono- or disubstituted by alkyl of 1 to 3 carbons, methoxy, ethoxy, chlorine, fluorine, $NH_2$, or $CF_3$;
$R^1$ and $R^2$ are each independently selected from hydrogen and methyl;

X is

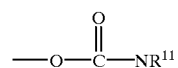

wherein $R^{11}$ is hydrogen or methyl;
$R^3$ is hydrogen or $(CH_2)_mR^{13}$ where m is an integer of from 1 to 6 and $R^{13}$ is H, CN, $NH_2$, $N(CH_3)_2$, or $NHCOCH_3$;
n is 1;
$R^8$ is phenyl,
naphthyl,
indole, or
benzothiophene;
Y is

wherein $R^4$ is hydrogen or methyl —$CO_2$—,

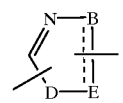

wherein B is CH, $CH_2$, D is sulfur, and E is CH, $CH_2$;
$R^5$ and $R^7$ are each independently hydrogen or methyl;
q is an integer of from 0 to 1, and
$R^6$ is phenyl, substituted phenyl, or cyclohexyl.
Still more preferred compounds of the invention are those of Formula I wherein
R is phenyl
thiophene,
furan,
each unsubstituted, or mono- or disubstituted by alkyl of 1 to 3 carbons, methoxy, ethoxy, chlorine, fluorine, $NH_2$, or $CF_3$;
$R^1$ and $R^2$ are each independently hydrogen or methyl;
X is

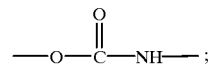

$R^3$ is hydrogen or methyl;
n is 1;
$R^8$ is indole;
Y is

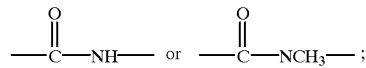

$R^5$ and $R^7$ are each independently hydrogen or methyl;
q is 1;
$R^6$ is phenyl,
substituted phenyl, or cyclohexyl.
Still more especially preferred compounds of the invention are:

phenylmethyl(S)-[1-(1H-indol-3-ylmethyl)-2-[methyl (phenylmethyl)amino]-2-oxoethyl]carbamate;
phenylmethyl[R-(R*,S*)]-[1-(1H-indol-3-ylmethyl)-2-oxo-2-[(1-phenylethyl)amino]ethyl]carbamate;
phenylmethyl[R-(R*,S*)]-[1-(1H-indol-3-ylmethyl)-1-methyl-2-oxo-2-[(1-phenylethyl)amino]ethyl]carbamate;
phenylmethyl[S-(R*,R*)]-[1-(1H-indol-3-ylmethyl)-2-oxo-2-[(1-phenylethyl)amino]ethyl]methyl]carbamate;
phenylmethyl[S-(R*,S*)]-[1-(1H-indol-3-ylmethyl)-2-oxo-2-[(1-phenylethyl)amino]ethyl]methylcarbamate;
(4-chlorophenyl)methyl(S)-[1-(1H-indole-3-ylmethyl)-2-oxo-2-[(phenylmethyl)amino]ethyl]methyl]carbamate;
(4-methoxyphenyl)methyl[R-(R*,S*)]-[1-(1H-indol-3-ylmethyl)-1-methyl-2-oxo-2-[(1-phenylethyl)amino] ethyl]carbamate;
(4-chlorophenyl)methyl[R-(R*,S*)]-[1-(1H-indol-ethyl] carbamate;
(4-methylphenyl)methyl[R-(R*,S*)]-[1-(1H-indol-3-ylmethyl)-1-methyl-2-oxo-2-[(1-phenylethyl)amino] ethyl]carbamate;
phenylmethyl(S)-[1-(1H-indol-3-ylmethyl)-2-[methyl (phenylmethyl)amino]-2-oxoethyl]carbamate;
phenylmethyl(S)-[2-[[(4-chlorophenyl)methyl]-amino]1-(1H-indol-3-ylmethyl)-2-oxoethyl]-methylcarbamate;
phenylmethyl(S)-[1-(1H-indol-3-ylmethyl)-2-oxo-2-[[[4-(trifluoromethyl)phenyl]methyl]amino]ethyl]-methylcarbamate;
methyl N-[(phenylmethoxy)carbonyl]-, [3,5-bis (trifluoromethyl)phenyl]-L-tryptophan;
phenylmethyl[1-(1H-indol-3-ylmethyl)-1-methyl-2-[[1-(4-methylphenyl)ethyl]amino]-2-oxoethyl]carbamate;
phenylmethyl[R-(R*,R*)]-[2-[(1-cyclohexylethyl)-amino]-1-(1H-indol-3-ylmethyl)-1-methyl-2-oxoethyl] carbamate;
phenylmethyl[2-[[1-[3,5-bis(trifluoromethyl)-phenyl]ethyl]amino]-1-(1H-indol-3-ylmethyl)-1-methyl-2-oxoethyl] carbamate;
phenylmethyl (R,RS)-[1-(1H-indol-3-ylmethyl)-2-[[1-(4-methoxyphenyl)ethyl]amino]-1-methyl-2-oxoethyl] carbamate;
4-pyridinylmethyl[R-(R*,S*)]-[1-(1H-indol-3-ylmethyl)-1-methyl-2-oxo-2-[(1-phenylethyl)amino]carbamate;
3-thienylmethyl[R-(R*,S*)]-[1-(1H-indol-3-ylmethyl)-1-methyl-2-oxo-2-[(1-phenylethyl)amino]ethyl]carbamate;
2-thienylmethyl[R-(R*,S*)]-[1-(1H-indol-3-ylmethyl)-1-methyl-2-oxo-2-[(1-phenylethyl)amino]ethyl]carbamate;
2,3-dihydro-1H-inden-3-yl [R-(R*,S*)]-[1-(1H-indol-3-ylmethyl)-1-methyl-2-oxo-2-[(phenylethyl)amino]ethyl] carbamate;
1-naphthalenylmethyl[R-(R*,S*)]-[1-(1H-indol-3-ylmethyl)-1-methyl-2-oxo-2-[(phenylethyl)amino]ethyl] carbamate;
2,3-dihydro-1H-inden-2-yl[1-(1H-indol-3-ylmethyl)-1-methyl-2-oxo-2-[(phenylethyl)amino]ethyl]carbamate;
(2-fluorophenyl)methyl[R-(R*,S*)]-[1-(1H-indol-3-ylmethyl)-1-methyl-2-oxo-2-[(phenylethyl)amino]ethyl] carbamate;
3-furanylmethyl[R-(R*,S*)]-[1-(1H-indol-3-ylmethyl)-1-methyl-2-oxo-2-[(phenylethyl)amino]ethyl]carbamate;
2-furanylmethyl[R-(R*,S*)]-[1-(1H-indol-3-ylmethyl)-1-methyl-2-oxo-2-[(phenylethyl)amino]ethyl]carbamate;
(3-fluorophenyl)methyl[R-(R*,S*)]-[1-(1H-indol-3-ylmethyl)-1-methyl-2-oxo-2-[(phenylethyl)amino]ethyl] carbamate;
(2,3-difluorophenyl)methyl[R-(R*,S*)]-[1-(1H-indol-3-ylmethyl)-1-methyl-2-oxo-2-[(phenylethyl)amino]ethyl] carbamate;
(4-fluorophenyl)methyl[R-(R*,S*)]-[1-(1H-indol-3-ylmethyl)-1-methyl-2-oxo-2-[(phenylethyl)amino]ethyl] carbamate;
(2,4-difluorophenyl)methyl[R-(R*,S*)]-[1-(1H-indol-3-ylmethyl)-1-methyl-2-oxo-2-[(phenylethyl)amino]ethyl] carbamate;
(2,5-difluorophenyl)methyl[R-(R*,S*)]-[1-(1H-indol-3-ylmethyl)-1-methyl-2-oxo-2-[(phenylethyl)amino]ethyl] carbamate;
phenylmethyl[R-(R*,S*)] and [S-(R*,R*)]-[1-(1H-indazol-3-ylmethyl)-2-oxo-2-[(1-phenylethyl)amino]ethyl] carbamate;
phenylmethyl[R-(R*,S*)] and [S-(R*,R*)]-[1-[(5-fluoro-1H-indol-3-yl)methyl]-2-oxo-2-[(1-phenylethyl)amino] ethyl]carbamate;
-phenylmethyl[1-(1-methyl-1H-indol-3-ylmethyl)-2-oxo-2-[(1-phenylethyl)amino]ethyl]carbamate;
phenylmethyl[R-(R*,S*)]-[1-(2-naphthalenyl-methyl)-2-oxo-2-[(1-phenylmethyl)amino]ethyl]carbamate;
1-phenylethyl (S)-N-[(phenylmethoxy)carbonyl)]-DL-tryptophan, (S)-;
phenylmethyl[1-(benzo[b]thien-3-ylmethyl)-1-methyl-2-oxo-2-[(1-phenylethyl)amino]ethyl]carbamate;
carbamic acid, [1-(1H-indol-3-ylmethyl)-1-methyl-2-oxo-2-[(1-phenylethyl)amino]ethyl]-, 2-benzofuranyl-methyl ester, [R-(R*,S*)];
carbamic acid, [1-(1H-indol-3-ylmethyl)-1-methyl-2-oxo-2-[(1-phenylethyl)amino]ethyl]-, benzo[b]thien-2-ylmethyl ester, [R-(R*,S*)];
[2-(1H-indol-3-yl)-1-methyl-1-(1-phenyl-ethylcarbamoyl)-ethyl]-carbamic acid 2-fluoro-5-methyl-benzyl ester;
carbamic acid, [1-(1H-indol-3-ylmethyl)-1-methyl-2-oxo-2-[[1-(4-pyridinyl)ethyl]amino]ethyl]-, 2-benzofuranylmethyl ester, monohydrochloride, [R-(R*,S*)];
carbamic acid, [1-(1H-indol-3-ylmethyl)-2-[methyl-(phenylmethyl)amino]-2-oxoethyl]-, 2-benzofuranylmethyl ester, (S)-;
carbamic acid, [1-(1H-indol-3-ylmethyl)-2-[methyl-(phenylmethyl)amino]-2-oxoethyl]-, benzo[b]thien-2-ylmethyl ester, (S)-.

Another aspect of the invention is a pharmaceutical composition comprising an amount of a compound according to Formula I effective to treat respiratory disorders in a mammal suffering therefrom, and a pharmaceutically acceptable carrier.

Another aspect of the invention is a method for treating respiratory disorders in a mammal such as a human comprising administering a therapeutically effective amount of a compound according to Formula I.

Another aspect of the invention is a pharmaceutical composition comprising an amount of a compound according to Formula I effective to treat inflammation in a mammal suffering therefrom, and a pharmaceutically acceptable carrier.

Another aspect of the invention is a method for treating inflammation in a mammal such as a human comprising administering a therapeutically effective amount of a compound according to Formula I.

Another aspect of the invention is a pharmaceutical composition comprising an amount of a compound according to Formula I effective to treat gastrointestinal disorders in a mammal suffering therefrom, and a pharmaceutically acceptable carrier.

Another aspect of the invention is a method for treating gastrointestinal disorders in a mammal such as a human comprising administering a therapeutically effective amount of a compound according to Formula I.

Another aspect of the invention is a pharmaceutical composition comprising an amount of a compound according to Formula I effective to treat eye diseases such as dry eye and conjunctivitis in a mammal suffering therefrom, and a pharmaceutically acceptable carrier.

Another aspect of the invention is a method for treating eye diseases in a mammal such as a human comprising administering a therapeutically effective amount of a compound according to Formula I.

Another aspect of the invention is a pharmaceutical composition comprising an amount of a compound according to Formula I effective to treat allergies in a mammal suffering therefrom, and a pharmaceutically acceptable carrier.

Another aspect of the invention is a method for treating allergies in a mammal such as a human comprising administering a therapeutically effective amount of a compound according to Formula I.

Another aspect of the invention is a pharmaceutical composition comprising an amount of a compound according to Formula I effective to treat diseases of the central nervous system in a mammal suffering therefrom, and a pharmaceutically acceptable carrier.

Another aspect of the invention is a method for treating diseases of the central nervous system in a mammal such as a human comprising administering a therapeutically effective amount of a compound according to Formula I.

Another aspect of the invention is a pharmaceutical composition comprising an amount of a compound according to Formula I effective to treat migraine in a mammal suffering therefrom, and a pharmaceutically acceptable carrier.

Another aspect of the invention is a method for treating migraine in a mammal such as a human comprising administering a therapeutically effective amount of a compound according to Formula I.

Another aspect of the invention is a pharmaceutical composition comprising an amount of compound according to Formula I effective to treat pain arising from neurogenic inflammation or inflammatory pain.

Another aspect of the invention is a method for treating pain such as pain arising from neurogenic inflammation in inflammatory pain status.

Another aspect of the invention is a pharmaceutical composition comprising an amount of a compound according to Formula I effective in treating conditions associated with aberrant neovascularization: rheumatoid arthritis, atherosclerosis, and tumor cell growth.

Another aspect of the invention is a method of treating conditions associated with aberrant neovascularization: rheumatoid arthritis, atherosclerosis, and tumor cell growth.

Another aspect of the invention is using the compounds as imaging agents for imaging $NK_1$ receptors in vivo.

Processes for preparing the compounds and novel intermediates are included in the invention.

DETAILED DESCRIPTION OF THE INVENTION

The following terms are descriptive of the compounds of the instant invention.

The alkyl groups contemplated by the invention include straight, branched, or cyclic carbon chains of from 1 to 8 carbon atoms except where specifically stated otherwise. Representative groups are methyl ethyl, propyl, isopropyl, n-propyl, n-butyl, iso-butyl, sec-butyl, 2-methylhexyl, n-pentyl, 1-methylbutyl, 2,2-dimethylbutyl, 2-methylpentyl, 2,2-dimethylpropyl, n-hexyl, and the like.

The cycloalkyl groups contemplated by the invention comprise those having 3 to 6 carbon atoms.

The alkoxy groups contemplated by the invention comprise both straight and branched carbon chains of from 1 to 6 carbon atoms unless otherwise stated. Representative groups are methoxyl, ethoxy, propoxy, i-propoxy, t-butoxy, and hexoxy.

The term halogen is intended to include fluorine, chlorine, bromine, and iodine.

The term aryl is intended to include substituted or unsubstituted phenyl, naphthyl, biphenyl, and indanyl. The substituents include one or more substituents such as halogens, nitro, alkyl, alkoxy, alkylthio, hydroxy, trifluoromethyl, and others as specified or as would occur to one skilled in the art.

The term arylalkyl is as described above for the two terms individually.

The term heterocyclic comprises substituted or unsubstituted pyridyl, 2- or 3-indolyl, thienyl, quinolyl, furanyl, isoquinolyl, benzofuranyl, and benzothiophenyl.

The term amide/ester replacement refers to such moieties as ketomethylene, methyleneoxy, tetrazole, 1,2,4-oxadiazole, and thiazole, etc. See for example Fincham, et al, *J Med Chem*, 1992;35:1472–1482 or Saunders, et al., *J Med Chem*, 1990;33:1128–1138.

The compounds of the instant invention are highly selective antagonists of the tachykinin receptor.

One such compound (Ex. 15) is an antagonist of the $NK_1$ in contrast to substance-P methyl ester which is a known selective $NK_1$ receptor agonist. See Table I below.

TABLE I $NK_1$ Antagonist Activity

| | $pk_B/pA_2$ | |
|---|---|---|
| Example | Guinea Pig Trachea[a] | Guinea Pig Ileum[b] |
| 15 | 7.4 | 7.8 |
| 20 | 7.0 | 7.7 |
| 22 | 7.0 | 7.8 |
| 45 | 7.2 | 8.0 |
| 47 | 7.3 | 8.4 |
| 53 | 8.1 | 8.6 |
| 54 | 7.9 | 8.3 |
| 63 | 8.7 | 9.5 |
| 64 | 7.1 | 8.7 |
| 67 | — | 7.9 |

[a]Ireland SJ, et al., Regulatory Peptides 1988;22:93.
[b]McKnight AT, et al., Br J Pharmacol 1991;104:355-60.

As can be seen from the data in Table I above, the compounds of the invention (for example, Ex. 15), is a tachykinin $NK_1$ receptor antagonist in a number of in vitro $NK_1$ preparations, i.e., it antagonizes the pharmacological action of the selective $NK_1$ receptor agonist substance-P methylester on these tissues with a $pK_B$ of about 8. Therefore, it could be of use in therapeutic disorders where attenuation of the $NK_1$ receptor response is an appropriate form of intervention.

These compounds are active in vivo as $NK_1$ receptor antagonists (see Table II). They antagonize the ability of a $NK_1$ receptor selective agonist (SPOMe) to induce plasma protein extravasation in the guinea pig bladder. The protocol is similar to that described by Eglezos, et al., *Eur J Pharmacol* 1991;209:277–279.

TABLE II

Guinea Pig Plasma Extravasation

| Example | $ID_{50}$ (mg/kg IV) |
|---|---|
| 22 | 0.64 |
| 45 | 0.61 |
| 47 | 0.13 |
| 53 | 0.071 |

TABLE II-continued

Guinea Pig Plasma Extravasation

| Example | ID$_{50}$ (mg/kg IV) |
|---|---|
| 54 | 0.051 |
| 63 | 0.024 |
| 66 | 2.8 |
| 67 | 0.91 |

The compounds of the invention were also evaluated in three tachykinin binding assays. For the NK$_1$ receptor measurement of the binding of [$^{125}$I-BH]. Substance-P, 0.1 nM to guinea pig cerebral cortex membranes was measured as in Lee C M, et al, *Eur J Pharmacol* 1986;130:209 and in *Br J Pharmacol* 1990;99:767.

For the NK$_2$ receptor measurement of the binding of [$^{125}$I]-iodohistidyl neurokinin A (0.1 nM) to hamster urinary bladder membrane was measured as described in Buck, Shatzer *Life Sci* 1988;42:2701.

For the NK$_3$ receptor measurement of the binding of [$^3$H]-Senktide (2 nM) to a guinea pig cerebral cortex membrane was taken as described in Lee C M, above.

See Table III below for the binding data for representative compounds of the invention. This table shows in vitro NK$_1$ receptor binding data for certain compounds of the invention.

TABLE III

In Vitro NK$_1$ Receptor Binding Data

| Example | Binding IC$_{50}$ (nM) |
|---|---|
| 1 | 341 |
| 3 | 218 |
| 4 | 198 |
| 6 | 75 |
| 7 | 306 |
| 15 | 36 |
| 16 | 702 |
| 20 | 64 |
| 21 | 27 |
| 22 | 17 |
| 23 | 168 |
| 24 | 185 |
| 27 | 306 |
| 29 | 487 |
| 35 | 233 |
| 36 | 70 |
| 37 | 290 |
| 38 | 100 |
| 39 | 10,000 |
| 40 | 210 |
| 41 | >10,000 |
| 42 | 140 |
| 43 | 100 |
| 44 | 110 |
| 45 | 14 |
| 46 | 110 |
| 47 | 10 |
| 48 | 230 |
| 49 | 120 |
| 50 | 120 |
| 51 | 230 |
| 52 | 49 |
| 53 | 39 |
| 54 | 19 |
| 55 | >1000 |
| 56 | 3200 |
| 57 | 3400 |
| 58 | 1700 |
| 60 | >1000 |
| 63 | 9 |

TABLE III-continued

In Vitro NK$_1$ Receptor Binding Data

Table II shows the concentration of the compounds of the instant invention which is needed to displace 50% of a specific radioligand ([125I] Bolton Hunter labeled Substance-P) from tachykinin NK$_1$ receptor sites in guinea pig cerebral cortex membranes. It is a measure of the affinity these compounds have for this receptor.

As can be seen from the binding data above, several of these compounds have high affinity for the NK$_1$ receptor.

Compounds of the invention are expected to be useful in treating disorders mediated by tachykinins such as respiratory disorders, especially asthma.

They are also expected to be useful in treating inflammation such as arthritis, gastrointestinal disorders such as colitis, Crohn's disease, and irritable bowel syndrome.

They are further expected to be useful in treating and/or preventing eye diseases such as dry eye and conjunctivitis.

They are further expected to be useful in treating allergies such as rhinitis (common cold), and eczema.

The compounds are expected to treat vascular disorders such as angina and migraine.

They are further expected to be useful in preventing and/or treating diseases of the central nervous system such as schizophrenia.

Scheme I below illustrates the synthesis of Examples 1–8 and 35, CBZ-Trp-OPFP (carbobenzoxy-Trp-pentafluorophenyl) was treated with N-methyl benzylamine in EtOAc to give Examples 1–3 when using the appropriate tryptophan stereochemistry (i.e., Example 2 uses R-Trp etc). Examples 4–8 were prepared using the same pentafluorophenyl ester of tryptophan as above but this time it was reacted with RS,R or S α-methylbenzylamine using EtOAc as the solvent. The compound of Example 35 was prepared by reacting the above PFP ester with 3,5 di-CF$_3$ benzyl alcohol.

SCHEME I

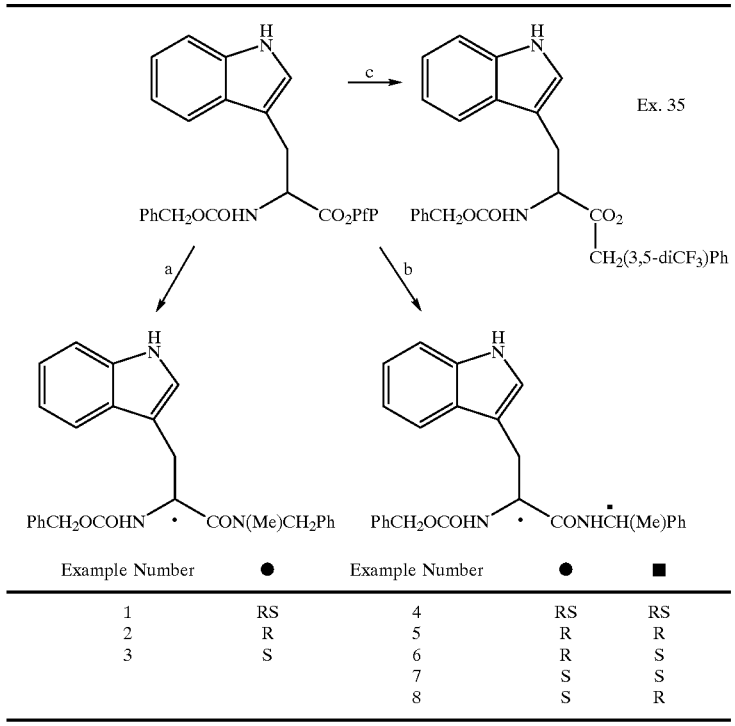

Reagents: a) PhCH$_2$N(Me)H; b) PhCH(Me)NH$_2$; c) (3,5-diCF$_3$)PhCH$_2$OH

In Scheme II (see below) the versatile intermediate, CBZ-tryptophanyl pentafluorophenyl ester was treated with a variety of arylmethylamines. Example 9 was prepared using 4-chlorobenzylamine in ethyl acetate. Similarly, Example 10 was prepared using 1,2,3,4-tetrahydronaphthyl-1-amine under similar conditions to that for Example 9.

Another versatile intermediate shown in Scheme II is the N-terminal unprotected tryptophanyl benzylamide, treatment of this in dry dichloromethane with 1-phenylethanol in the presence of 4-nitrophenylchloroformate yielded Example 11.

SCHEME II

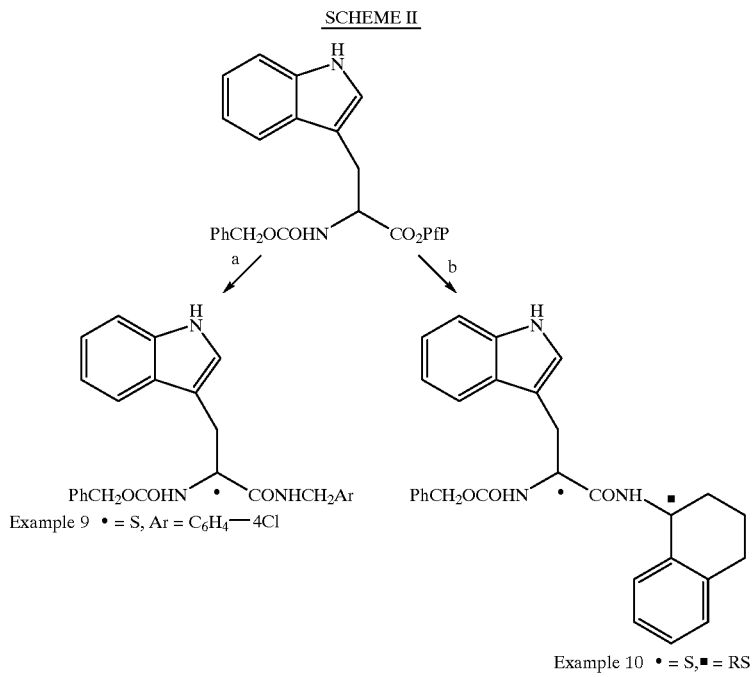

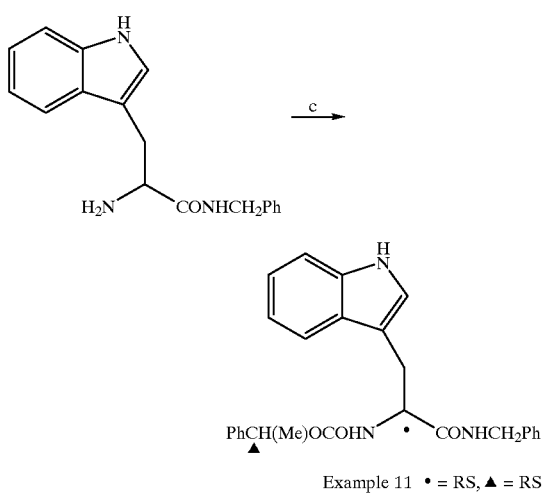

Example 11 • = RS, ▲ = RS

Reagents: a) ArCH₂NH₂; b) 1,2,3,4-tetrahydronaphthyl-1-amine; c) 1-phenylethanol and nitrophenylchloroformate Scheme III below outlines the synthesis of Examples 12–18, α-Methyl tryptophan methylester was initially treated with benzylchloroformate in aqueous 1,4-dioxane and in the presence of base to give the CBZ-protected ester. This ester was then saponified with lithium hydroxide to the corresponding acid which was then treated with dicyclohexylcarbodiimide (DCC) in the presence of pentafluorophenol (PFP—OH) to give CBZ-α-methyl tryptophan pentafluorophenyl ester. This active ester was treated with benzylamine to give Example 12. The same ester was also treated with N-methylbenzylamine to yield Example 13. Examples 14–18, 36, 37, 38, 39, and 40 were prepared again from this PFP-ester using the appropriate amine.

SCHEME III

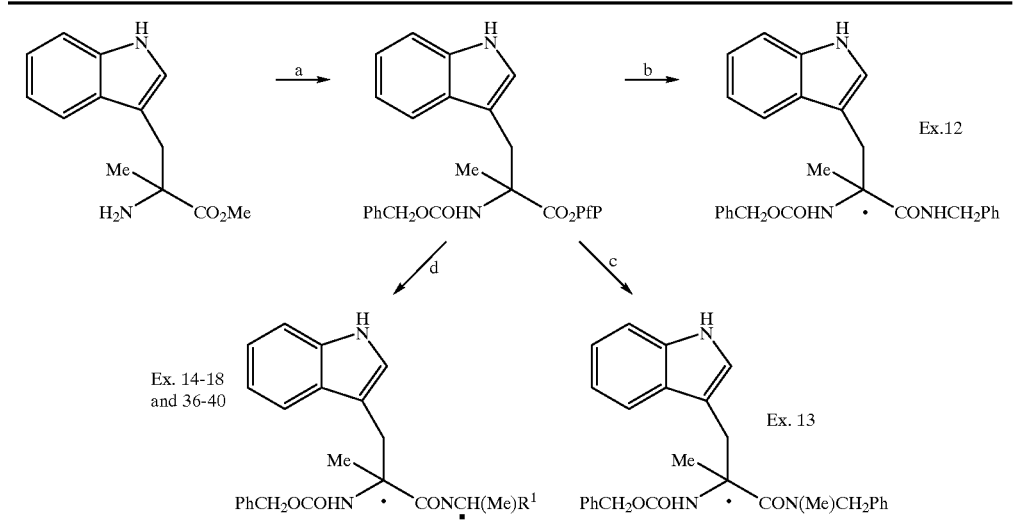

| Example Number | ● | ■ | R¹ |
|---|---|---|---|
| 12 | RS | — | — |
| 13 | R | — | — |
| 14 | R | RS | 4ClPh |
| 15 | R | S | Ph |
| 16 | S | S | Ph |
| 17 | S | R | Ph |
| 18 | R | R | Ph |
| 36 | R | R or S | 4-CH₃Ph |
| 37 | R | R or S | 4-CH₃Ph |
| 38 | R | S | c-Hexyl |
| 39 | R | R,S | (3,5-diCF₃)Ph |
| 40 | R | R,S | 4-OCH₃Ph |

Reagents: a) i. PhCH₂OCOCl; ii. LiOH; iii. DCC,PfP; b) PhCH₂NH₂; c) PhCH₂N(Me)H; d) R¹CH(Me)NH₂

The synthetic routes described in Scheme IV below involve the very useful intermediate α-methyltryptophanyl-1-phenethylamide which can be synthesized from Example 15 by hydrogenation of the CBZ-N-terminal protecting group using Pearlmans catalyst in ethanol. This free amine may then be reacted with the appropriate chloroformate or active carbonate to give Examples 20–22, 41–54, and 63–65. Example 19 was prepared by the action of the amine on benzyl isocyanate.

Example 25 was synthesized by preparing an active ester of the abrine derivative with pentafluorophenol and dicyclohexylcarbodiimide then reacting this with N-methylbenzylamine. Similarly, Examples 23, 26, and 28

SCHEME IV

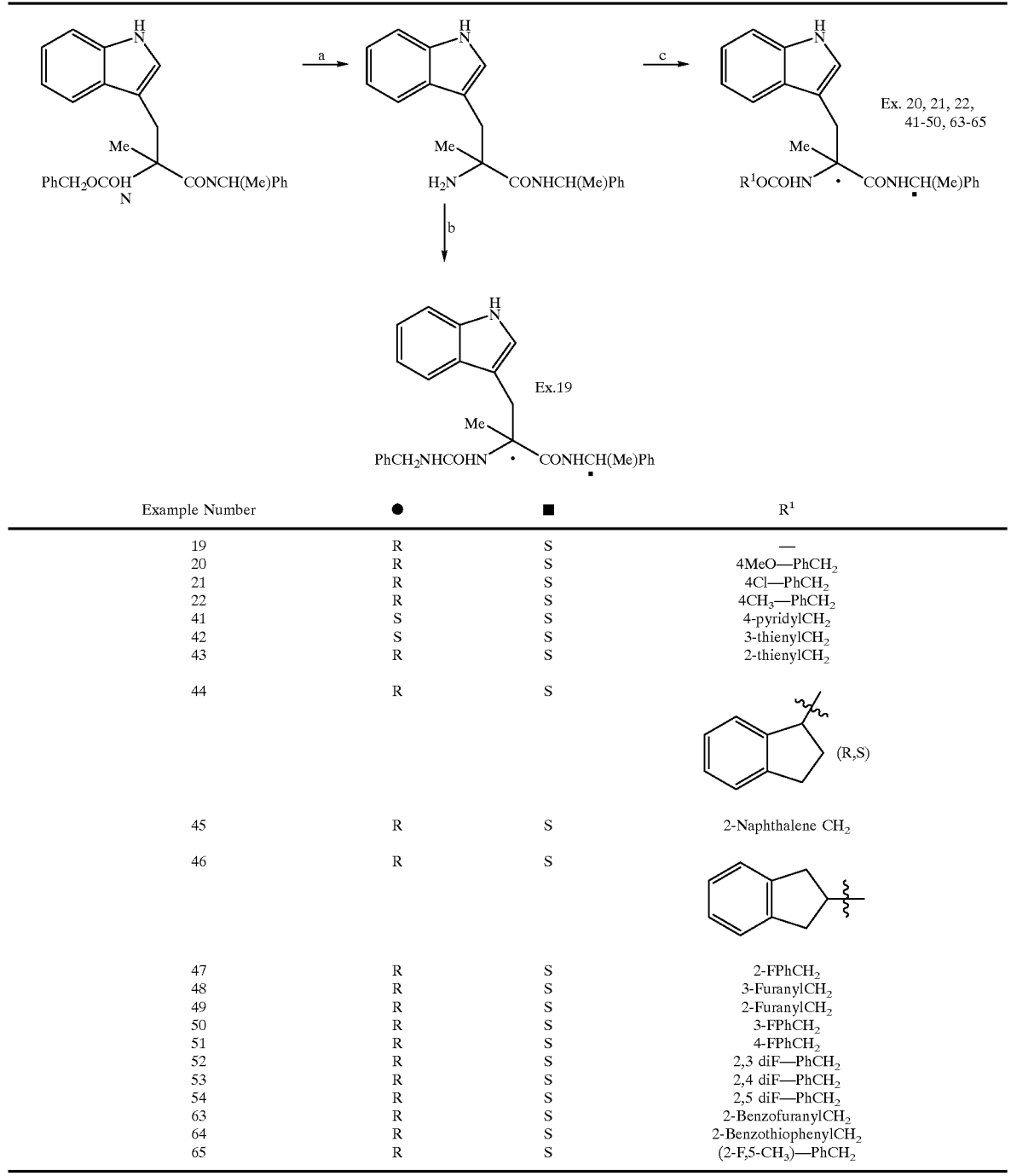

| Example Number | ● | ■ | R¹ |
|---|---|---|---|
| 19 | R | S | — |
| 20 | R | S | 4MeO—PhCH$_2$ |
| 21 | R | S | 4Cl—PhCH$_2$ |
| 22 | R | S | 4CH$_3$—PhCH$_2$ |
| 41 | S | S | 4-pyridylCH$_2$ |
| 42 | S | S | 3-thienylCH$_2$ |
| 43 | R | S | 2-thienylCH$_2$ |
| 44 | R | S | (R,S) indanyl |
| 45 | R | S | 2-Naphthalene CH$_2$ |
| 46 | R | S | indanyl |
| 47 | R | S | 2-FPhCH$_2$ |
| 48 | R | S | 3-FuranylCH$_2$ |
| 49 | R | S | 2-FuranylCH$_2$ |
| 50 | R | S | 3-FPhCH$_2$ |
| 51 | R | S | 4-FPhCH$_2$ |
| 52 | R | S | 2,3 diF—PhCH$_2$ |
| 53 | R | S | 2,4 diF—PhCH$_2$ |
| 54 | R | S | 2,5 diF—PhCH$_2$ |
| 63 | R | S | 2-BenzofuranylCH$_2$ |
| 64 | R | S | 2-BenzothiophenylCH$_2$ |
| 65 | R | S | (2-F,5-CH$_3$)—PhCH$_2$ | from Scheme III
Reagents: a) Pd(OH)$_2$, H$_2$, EtOH; b) PhCH$_2$N=C=O; c) ArCH$_2$OCOX As illustrated in Scheme V below, abrine (N-methyl tryptophan) gave benzyloxycarbonyl-abrine when exposed to benzylchloroformate in aqueous 1,4-dioxane in the presence of base. This N-protected abrine was then used to prepare many derivatives having various C-terminal groups.

were prepared by the reaction of this active ester with various aryl amines such as 4-trifluoromethylbenzylamine (Example 26) and 4-chlorobenzylamine (Example 28). Examples 24 and 27 were made by reaction of the same active ester with α-methylbenzylamine (1-phenethylamine).

SCHEME V

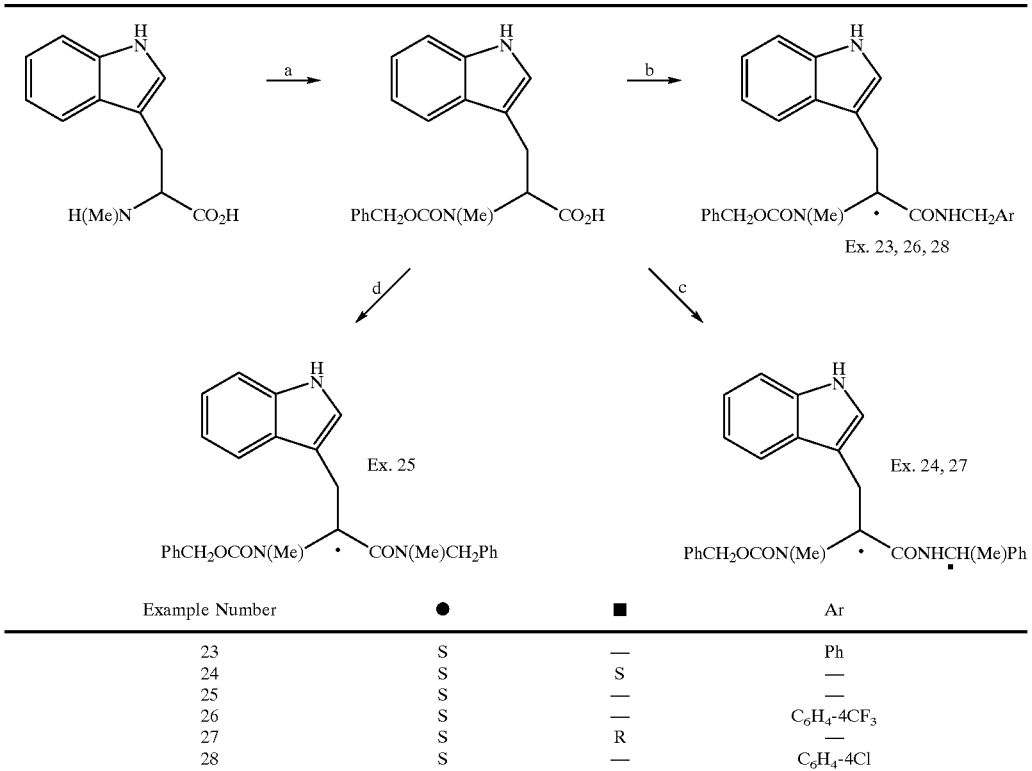

| Example Number | ● | ■ | Ar |
|---|---|---|---|
| 23 | S | — | Ph |
| 24 | S | S | — |
| 25 | S | — | — |
| 26 | S | — | $C_6H_4$-4$CF_3$ |
| 27 | S | R | — |
| 28 | S | — | $C_6H_4$-4Cl |

Reagents: a) $PhCH_2OCOCl$; b) i. DCC, PfP; ii. $ArCH_2NH_2$; c) i. DCC, PfP; ii. $PhCH_2(Me)NH_2$; d) i. DCC, PfP; ii. $PhCH_2N(Me)H$ Methods for derivatizing the N-terminus of the abrine-containing compounds were carried out via the methods shown in Scheme VI below. Abrine was treated with 9-fluorenylmethylchloroformate in aqueous 1,4-dioxane with sodium carbonate to give the FMOC-protected abrine. The active ester of this (PFP-OH,DCC) was then treated with benzylamine in ethyl acetate to give the amide which was deprotected under the standard conditions of 20% piperidine in DMF. This free amine was then treated with 4-chlorobenzyl chloroformate, 4-trifluoromethylbenzylchloroformate, and 2,3 dimethoxybenzyl-4'-nitrophenyl carbonate to give Examples 29, 30, and 31, respectively.

SCHEME VI

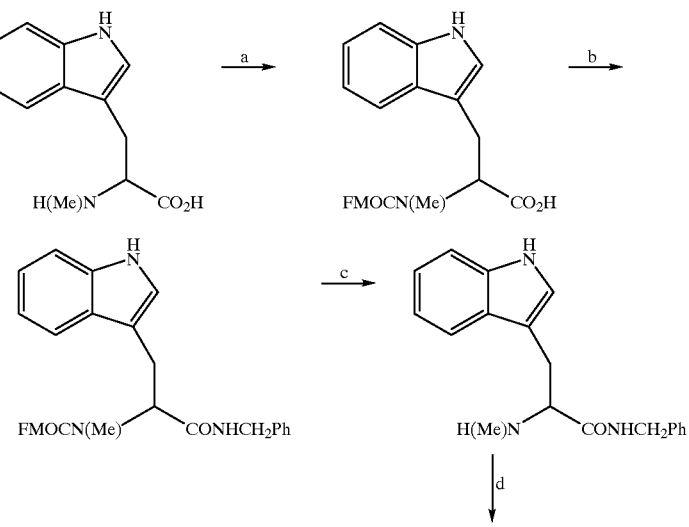

SCHEME VI-continued

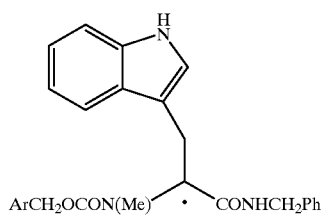

| Example Number | ● | Ar |
|---|---|---|
| 29 | S | $C_6H_4$-4Cl |
| 30 | S | $C_6H_4$-4$CF_3$ |
| 31 | S | $C_6H_3$-2,3,diMeO |

Reagents: a) FMOC—Cl; b) i. DCC, PfP; ii. $PhCH_2NH_2$; c) piperidine, DMF; d) $ArCH_2OCOX$ Examples 32, 33, 34, and 55–59 were prepared according to Scheme VII below. The appropriate amino acids were reacted to give their CBZ-protected derivatives. These compounds were then treated via their active esters with the appropriate amine or alcohol to produce the desired product.

SCHEME VII

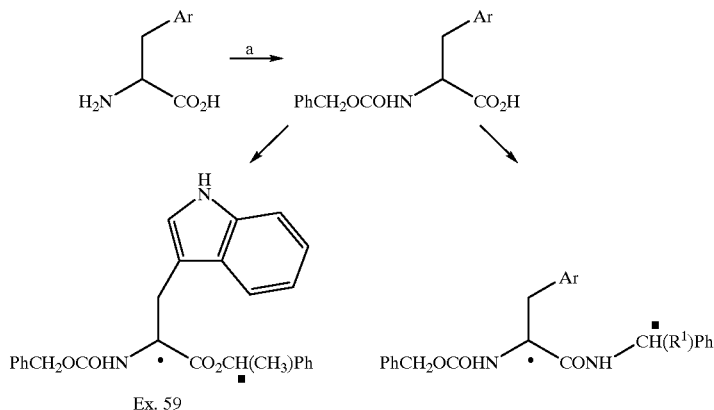

Ex. 59

| Example Number | ● | ■ | Ar | $R^1$ |
|---|---|---|---|---|
| 32 | R,S | — | (4-Cl)Ph | H |
| 33 | R,S | — | (4-Br)Ph | H |
| 34 | R,S | — | (3,4-diOH)Ph | H |
| 55 | R,S | S | 3-Indazole | $CH_3$ |
| 56 | R,S | S | 3-((5-F)Indole) | $CH_3$ |
| 57 | R,S | R,S | 3(N-Me Indole) | $CH_3$ |
| 58 | R | S | 2-Naphthalene | $CH_3$ |
| 59 | R,S | S | — | — |

Reagents:

a) $PhCH_2$—OCOX; X is a leaving group b) i. activation of carboxylic acid; ii. $PhCH(R^1)NH_2$ c) DCC, $PhCH(CH_3)OH$ Example 60 was prepared by the method shown in Scheme VIII below. The methyl ester of 3-benzothiophenylalanine was reacted with dibenzyldicarbonate to give the CBZ-protected derivative. This was then treated with base to give the carboxylic acid, which subsequently was activated and reacted with the appropriate amine.

SCHEME VIII
EXAMPLE 60

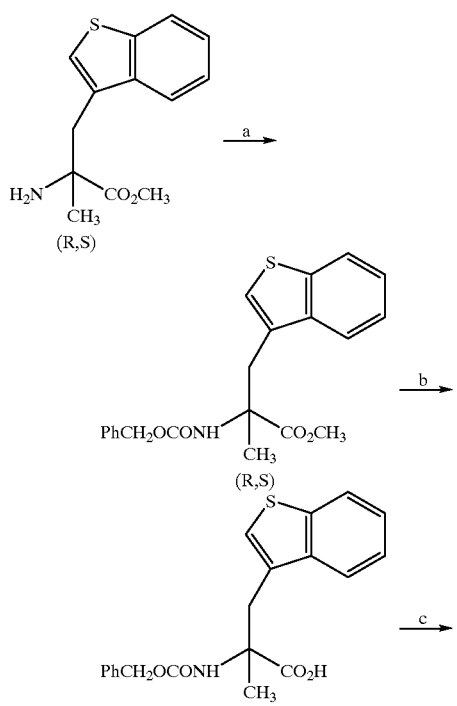

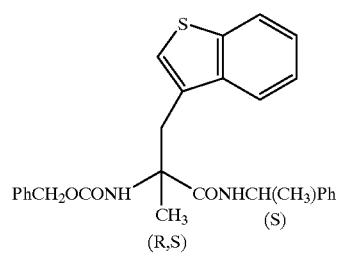

Reagents: a) (PhCH$_2$OCO)$_2$; b) LiOH; c) i. HOBt, DCC, ii. (S)PhCH(CH$_3$)NH$_2$ Example 61 was prepared by the method shown in Scheme IX below. CBZ α-Me tryptophan was activated to give the pentafluorophenyl ester (described in Scheme III) and reacted with the appropriate amino alcohol. This was then cyclized with Lawesson's reagent to give product.

SCHEME IX

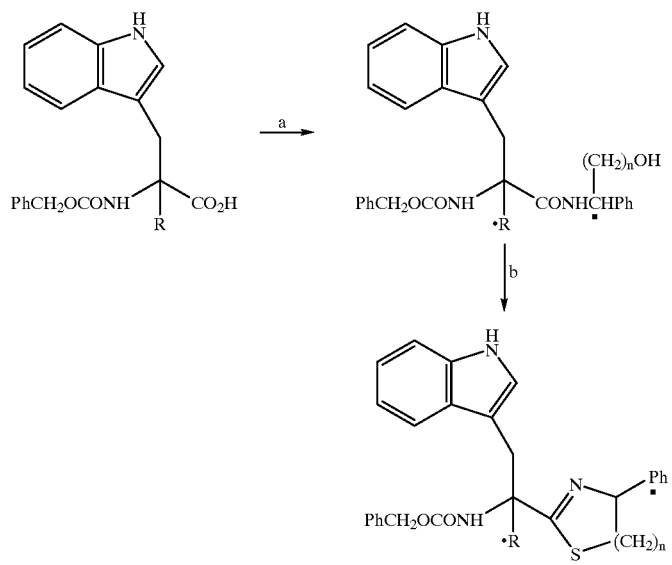

| Example Number | R | n | ● | ■ |
|---|---|---|---|---|
| 61 | CH$_3$ | 1 | R | R |

Reagents: a) i activation of acid; ii. amino alcohol b) Lawesson's reagent

Example 62 was prepared by the method shown in Scheme X below. The methyl ester of tryptophan was converted to the N-formyl derivative which was subsequently treated with (BOC)₂O to protect the indole nitrogen. The isonitrile was then formed and alkylated with bromoacetonitrile. The resulting product was treated with hydrochloric acid followed by benzylchloroformate to give the urethane. Next, the BOC-group was removed and the ester hydrolysed with lithium hydroxide. The acid was then activated an subsequently condensed with α-methylbenzylamine.

Example 66 was prepared by the method shown in Scheme XI below. The mixed carbonate was obtained by reduction of the carboxylic acid and reaction with p-nitrophenylchloroformate. This was then treated with the methyl ester of α-methyl tryptophan to yield the urethane; which was hydrolysed with base to give the acid. The resulting product was then activated as its p-nitrophenylester.

4-Acetyl pyridine was converted to the oxime, which was subsequently reduced to give the primary amine. This was reacted with the p-nitrophenyl-ester to give the amide. This was then converted to the hydrochloride salt.

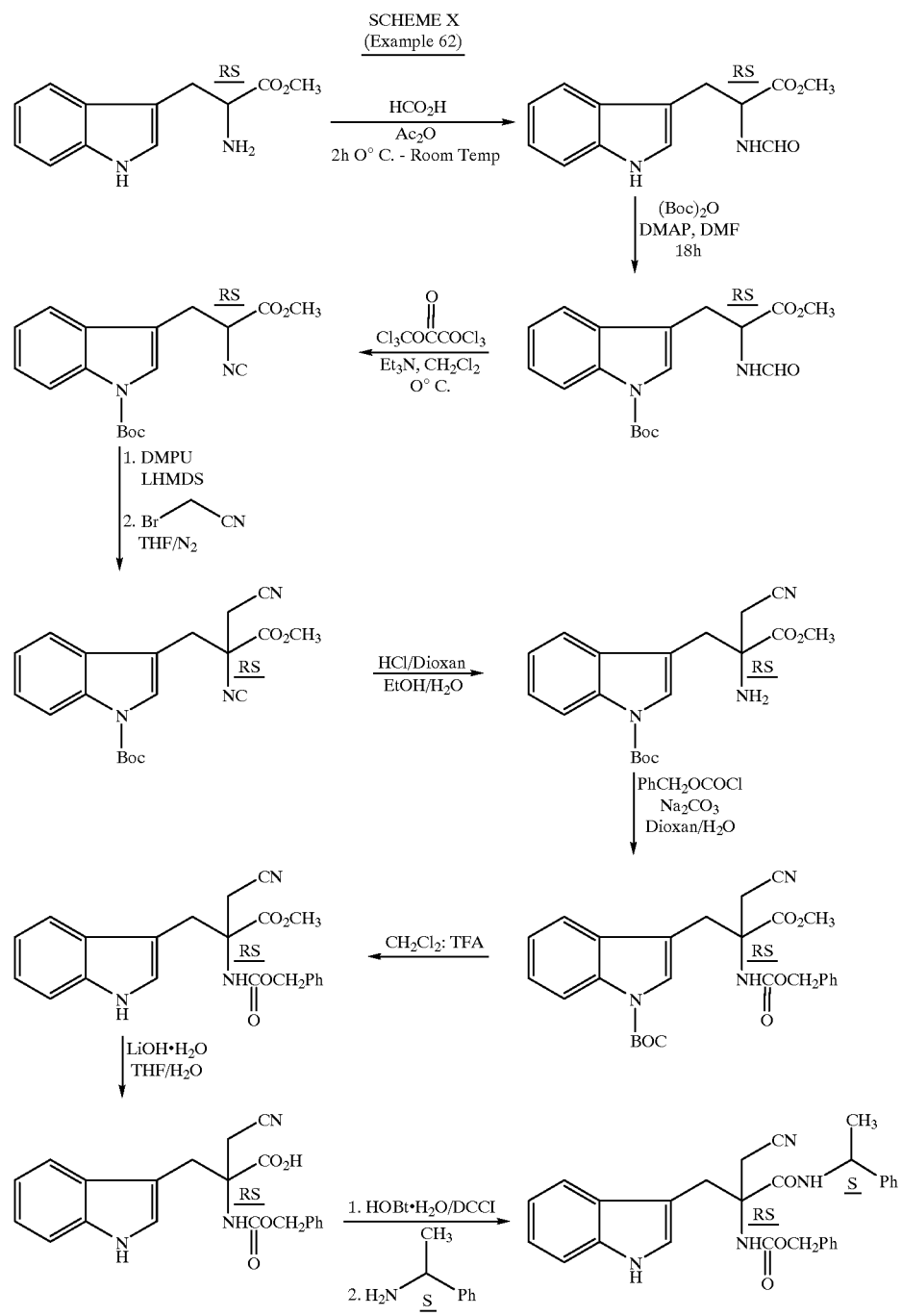

SCHEME XI
(Example 66)

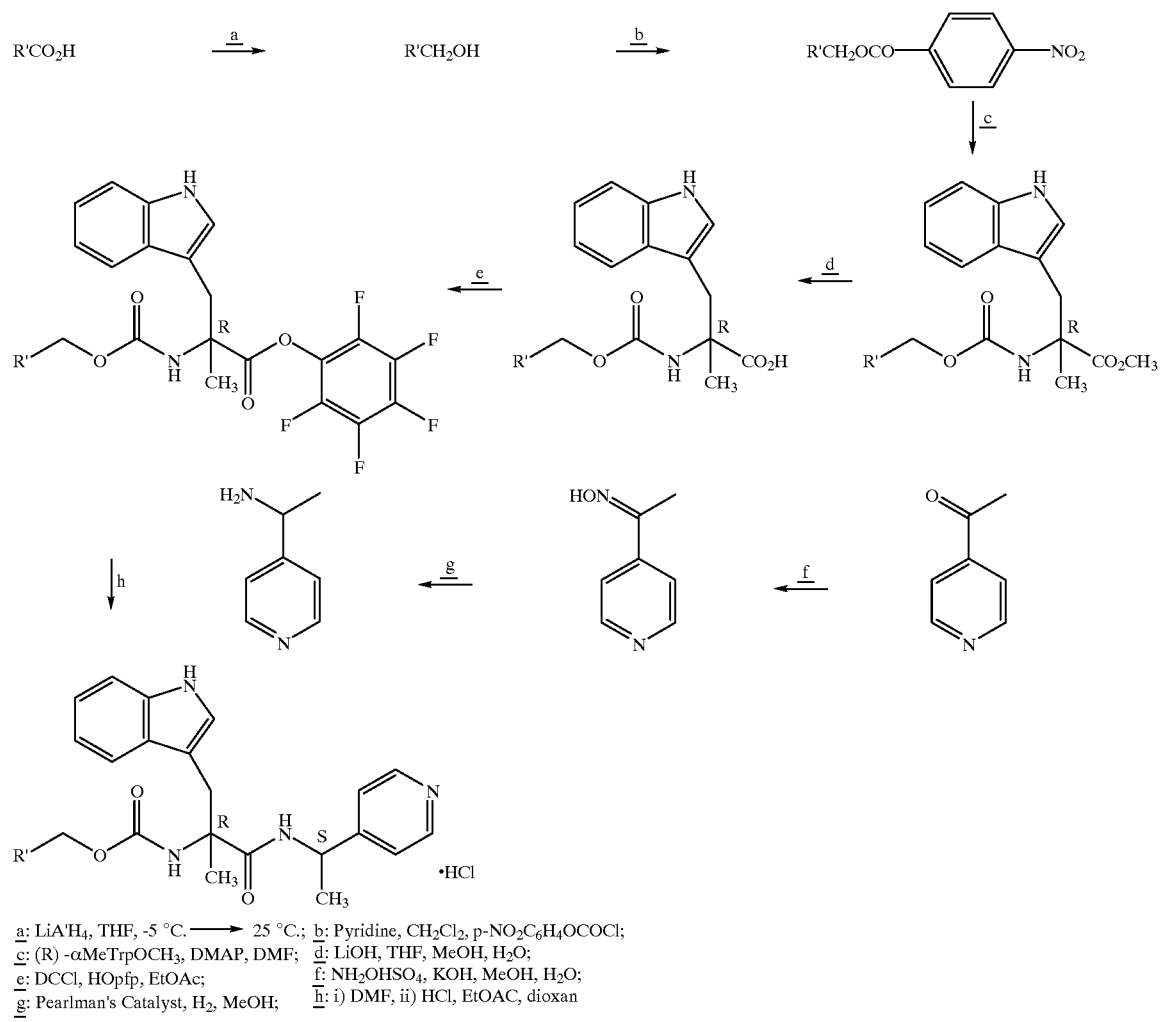

a: LiA'H₄, THF, -5 °C. ⟶ 25 °C.; b: Pyridine, CH₂Cl₂, p-NO₂C₆H₄OCOCl;
c: (R) -αMeTrpOCH₃, DMAP, DMF; d: LiOH, THF, MeOH, H₂O;
e: DCCl, HOpfp, EtOAc; f: NH₂OHSO₄, KOH, MeOH, H₂O;
g: Pearlman's Catalyst, H₂, MeOH; h: i) DMF, ii) HCl, EtOAC, dioxan Examples 67 and 68 were prepared by the method shown in Scheme XII below.

The BOC-protected-(S)-tryptophan-N-hydroxy-succinimidyl ester was reacted with N-methyl benzylamide to give the BOC-(s)-tryptophan-N-methyl-benzylamine which was deprotected with TFA to give the unprotected (S)-tryptophanyl-N-methyl benzylamide. This free amine was then reacted with the benzothiophenyl carbonate to give Example 68 and with the benzofuranylcarbonate to give Example 67.

SCHEME XII
(Examples 67 and 68)

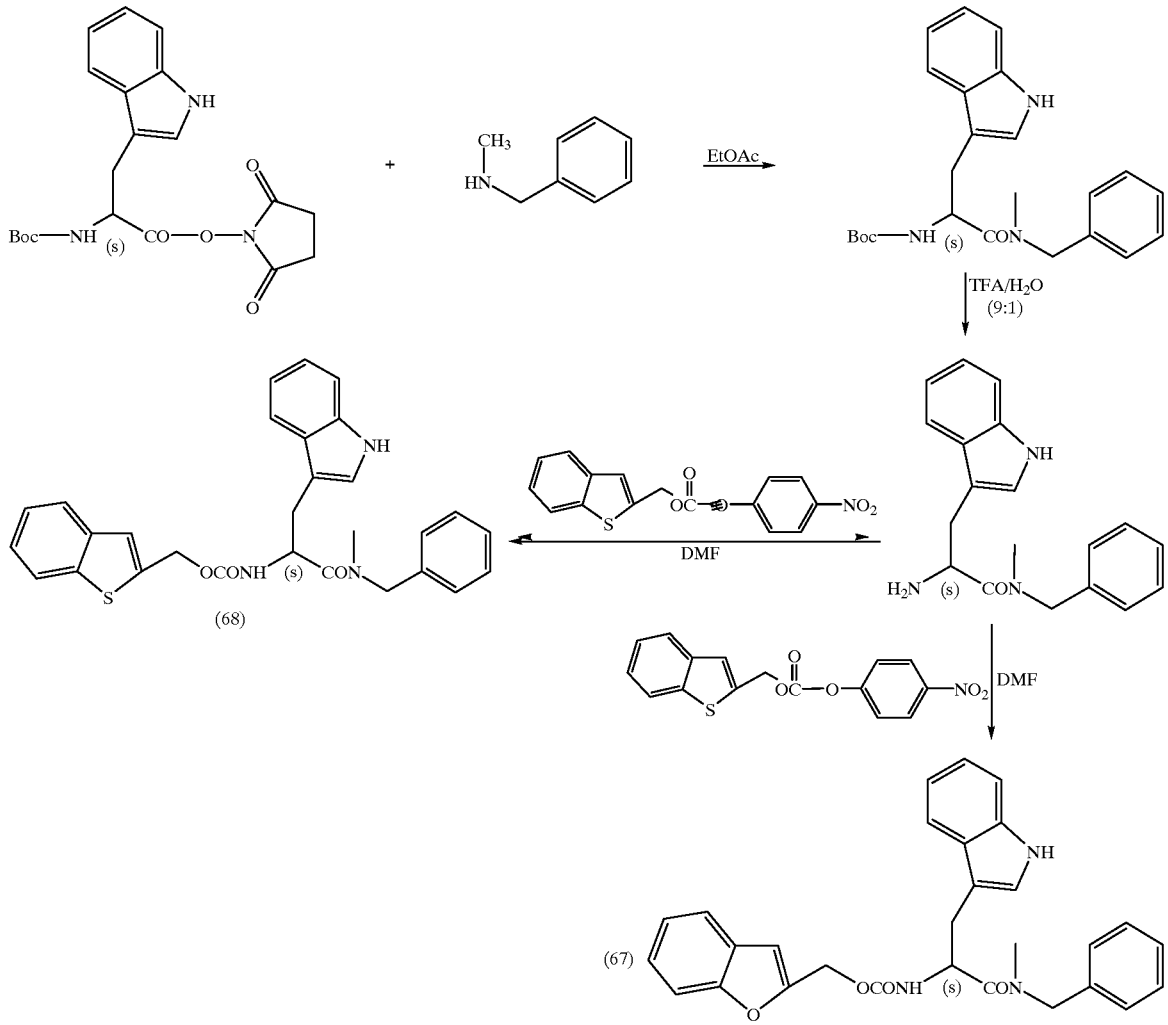

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

For preparing suppository preparations, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify.

The powders and tablets preferably contain 5% to about 70% of the active component. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

The compounds of the invention include solvates, hydrates, pharmaceutically acceptable salts, and polymorphs (different crystalline lattice descriptors) of the compounds of Formula I.

The compounds of the present invention can have multiple chiral centers in the above Formula I depending on their structures. In particular, the compounds of the present invention may exist as diastereomers, mixtures of diastereomers, or as the mixed or the individual optical enantiomers. The present invention contemplates all such forms of the compounds. The mixtures of diastereomers are typically obtained as a result of the reactions described more fully below. Individual diastereomers may be separated from mixtures of the diastereomers by conventional techniques such as column chromatography or repetitive recrystallizations. Individual enantiomers may be separated by conventional methods well known in the art such as conversion to a salt with an optically active compound, followed by separation by chromatography or recrystallization and reconversion to the nonsalt form.

Where it is appropriate to form a salt, the pharmaceutically acceptable salts are acetate, benzenesulfonate, benzoate, bicarbonate, bitartrate, bromide, calcium acetate, camsylate, carbonate, chloride, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate mesylate, methylbromide, methylnitrate, methylsulfate, mucate, napsylate, nitrate, pamoate (embonate), pantothenate, phosphate/diphosphate, polygalacturonate, salicylate, stearate, subacetate, succinate, sulfate, tannate, tartrate, theoclate, triethiodide, benzathine, chloroprocaine, choline, diethanolamine, ethylenediamine, meglumine, procaine, aluminum, calcium, lithium, magnesium, potassium, sodium, and zinc.

Cyclodextrin is one suitable inclusion in a pharmaceutical preparation.

The term "preparation" is intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid form preparations include solutions, suspensions, and emulsions. Sterile water or water-propylene glycol solutions of the active compounds may be mentioned as an example of liquid preparations suitable for parenteral administration. Liquid preparations can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Preferably the pharmaceutical preparation is in unit dosage form. In such form, the preparation is divided into unit doses containing appropriate quantities of the active component. The unit dosage form can be a packaged preparation, the package containing discrete quantities of the preparation, for example, packeted tablets, capsules, and powders in vials or ampoules. The unit dosage form can also be a capsule, cachet, or tablet itself, or it can be the appropriate number of any of these packaged forms.

EXAMPLE 1

(Scheme I)

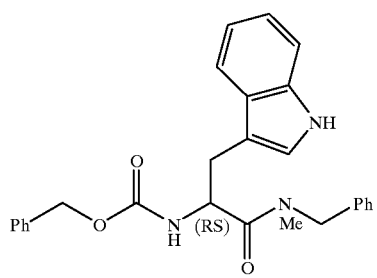

N-Methylbenzylamine (0.17 mL, 0.00126 mol) was added to a solution of CBZ-RS-Tryptophan pentafluorophenyl ester (0.64 g, 0.00126 mol) in EtOAc (5 mL) and the residue stirred at room temperature for 2 hours. The solvent was removed in vacuo and the residue dissolved in EtOAc (50 mL) and washed with 2 M hydrochloric acid (2×20 mL), water (2×10 mL), brine (20 mL), dried (MgSO$_4$) and the solvent evaporated in vacuo. The residue was purified via column chromatography eluting with dichloromethane:methanol (9:1) to give the product as a white solid (0.31 L g, 55%) mp 51–55° C.;

IR (film): 3301 (NH, urethane), 1708 (C=O, urethane), 1636 (C=O, amide), 1496, 1342, and 1232 cm$^{-1}$; NMR (CDCl$_3$): 2.51 and 2.74 (3H, s, CH$_3$N); 3.20 (2H, d, J=7 Hz, Trp-CH$_2$); 4.0–4.4 (2H, 2×m, ArCH$_2$N amide ROT); 4.9–5.1 (3H, m, ArCH$_2$O, αCH); 5.83 and 5.89 (1H, d, J=8 Hz, NH carbamate amide ROT); 6.7–7.7 (15H, m, aromatics); 8.2 and 8.3 (1H, s, NH, indole); MS m/e (CI) 442 (M$^+$+1).

EXAMPLE 2

(Scheme I)

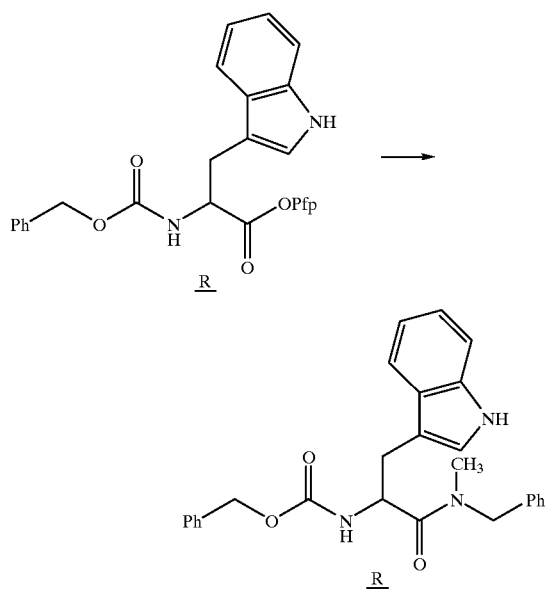

Method as described for Example 3, Scheme I, but using CBZ-R-Tryptophan pentafluorophenyl ester. Yield (0.08 g, 35%); mp 50–53° C.;

$[\alpha]_D^{23}$ −27.2 (C=0.25, MeOH); IR (film): 3296–2928, 1712 (urethane co), 1636 (amide I) and 1525 cm$^{-1}$ (amide II); NMR (DMSO-d$_6$): δ 2.75 (3H, s.CH$_3$); 3.01 (1H, d.d, J=7.5 and 13.9 Hz, one of Trp βCH$_2$); 444 (2H, s, CH$_2$Ph); 4.54 (1H, m, αCH), 5.01 (2H, s, PhCH$_2$O); 6.97–7.37 (15H, m, aromatics); 7.57 (1H, d, J=7.7 Hz, urethane NH); 10.7 (1H, S, indole NH); MS m/e (CI) 442 [M$^+$].

EXAMPLE 3

(Scheme I)

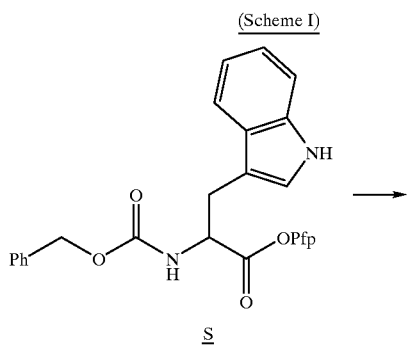

S

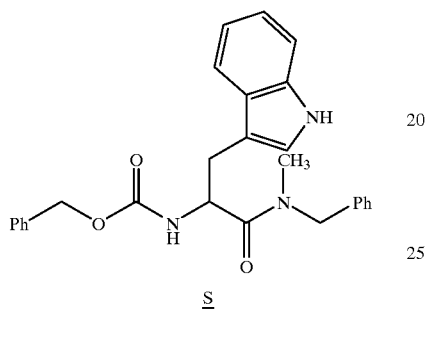

S

CBZ-L-tryptophan pentafluorophenyl ester (0.50 g, 1 mmol) was prepared in situ and reacted with benzylmethylamine (0.13 mL, 1 mmol) in ethylacetate (5 mL). The reaction mixture was stirred overnight at room temperature then washed with diluent HCl (1×10 mL), water (4×10 mL), and dried over MgSO$_4$. Removal of the solvent in vacuo resulted in a clear oil which was chromatographed to give the product (0.175 g, 40%); mp 48–50° C.;

$[\alpha]_D^{23}$=+30.4 (c=0.25, MeOH); IR (film): 3305–2927, 1710 (urethane CO), 1635 (amide I) and 1530 cm$^{-1}$ (amide II); NMR (DMSO-d$_6$, 1340K): δ 2.50 (3H, 3, CH$_3$); 3.0: (1H, d.d, J=7.3 and 13.8 Hz, one of βCH$_2$); 4.43 (2H, s, NCH$_2$Ph); 4.72 (1H, m, TrpαCH); 5.00 (2H, S, OCH$_2$Ph); 7.02–7.35 (15H, m, aromatics); 7.57 (1H, b, urethane NH); 10.65 (1H, s, indole NH); MS m/e (CI) 442 [M$^+$].

EXAMPLE 4

(Scheme I)

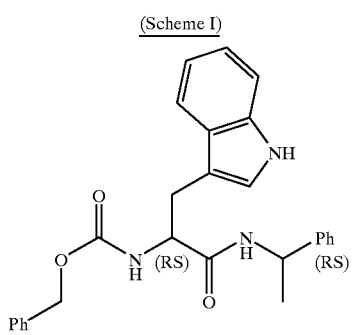

(RS) α-Methylbenzylamine (0.128 mL, 0.001 mol) was added to a solution of (CBZ-RS-tryptophan pentafluorophenyl ester (0.533 g, 0.001 mol) in EtOAc (15 mL) and the mixture stirred at room temperature for 15 min. The solvent was removed in vacuo and the residue dissolved in EtOAc (50 mL) and washed with 2 M hydrochloric acid (2×20 mL), water (2×10 mL), brine (20 mL), dried (MgSO$_4$) and the solvent evaporated in vacuo. The residue was purified via column chromatography eluting with hexane:ethyl acetate (8:2) to give Example 4 Scheme I as a white solid (0.33 g, 76%) mp 59–62° C.;

NMR: (CD$_3$SOCD$_3$): δ 1.23 and 1.34 (3H, d, J=7 Hz, CHC$\underline{H}_3$); 2.8–3.2 (2H, m, IndC$\underline{H}_2$); 4.3 (1H, m, CH); 4.9 (3H, m, ArCH$_2$O and NHCH); 6.9–7.4 (15H, aromatics and NH carbamate); 7.63 (1H, d, J=8 Hz, 4H-indole); 8.33 and 8.41 (1H, d, J=8 Hz NH amide); 10.8 (1H, s, indole NH); MS m/e (CI) 442 (M$^+$+H).

EXAMPLE 5

(Scheme I)

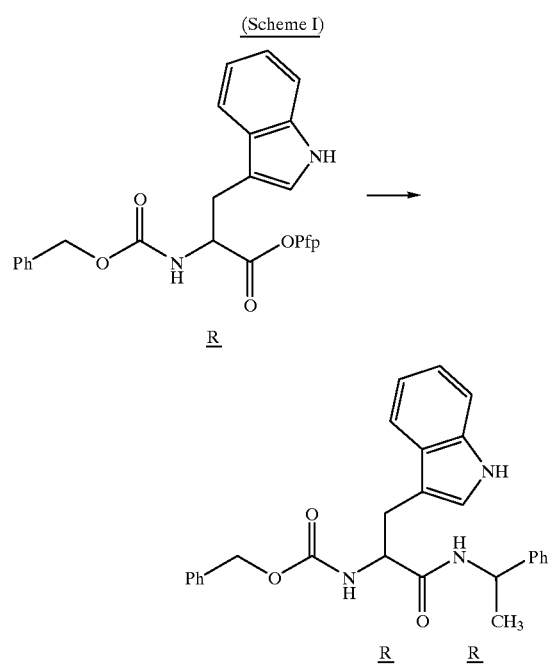

R

R R

CBZ-DL Tryptophan pentafluorophenyl ester (0.25 g, 0.5 mmol) was prepared in situ, dissolved in ethylacetate (2.5 mL) and (R)-(+)-α-methylbenzylamine (0.06 mL, 0.5 mmol) was added. The reaction mixture was stirred at room temperature until no starting material remained. The white precipitate was collected by filtration and recrystallized from ethylacetate to give Example 5 Scheme I (0.10 g, 44%); mp 169–170° C.;

$[\alpha]_D^{23}$=+12.8° (c=0.5, MeOH); IR (film): 3306, 1705 (urethane co), 1657 (amide I), and 1531 cm$^{-1}$ (amide II); NMR (DMSO-d$_6$): δ 1.35 (3H, d, J=6.7 Hz, CH$_3$); 2.87 (1H, d.d, J=9.2 and 14.3 Hz, one of Trp βCH$_2$); 3.06 (1H, d.d, J=4.8 and 14.3 Hz, one of Trp βCH$_2$); 4.36 (1H, m, C$\underline{H}$(CH$_3$Ph), 4.90–4.96 (3H, m, CH$_2$ Ph, αCH); 6.94–7.35 (15H, m, aromatics); 7.63 (1H, d, J=7.8 Hz, urethane NH); 8.41 (1H, d, J=7.8 Hz, amide NH); 10.8 (1H, s, indole NH); MS m/e (CI) 442 [M$^+$].

EXAMPLE 6

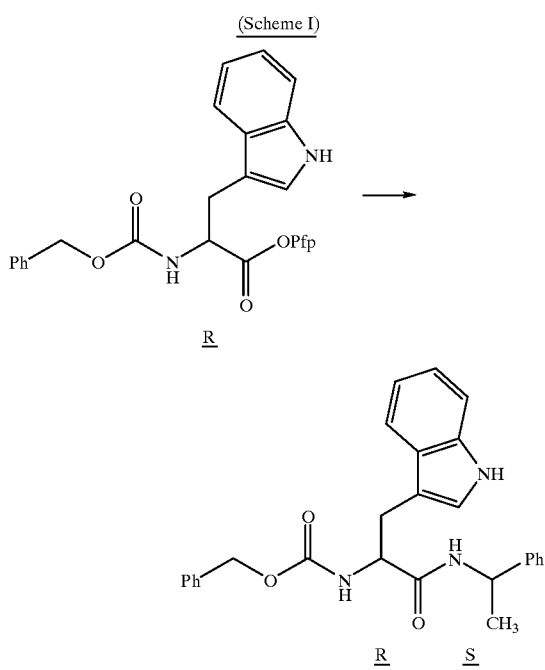

Method as described for Example 5, Scheme 1, but using (S)-(−)-α-methylbenzylamine. Yield (0.09 g, 21%); mp 160–161° C.;

$[\alpha]_D^{23}$=−26.0 (c=0.5, MeOH); IR (film): 3330, 1709 (urethane co), 1658 (amide I) and 1514 cm$^{-1}$ (amide II); NMR (DMSO-d$_6$): δ 1.23 (3H, d, J=6.8 Hz, CH$_3$); 2.95 (1H, d.d, J=9.4 and 14.3 Hz, one of Trp βCH$_2$); 3.08 (1H, d.d, J=5.4 and 14.3 Hz, one of Trp βCH$_2$); 4.32 (1H, m, CH(CH$_3$)Ph), 4.86–4.94 (3H, m, PhCH$_2$, αCH); 6.95–7.34 (15H, m.aromatics); 7.63 (1H, α, J=7.7 Hz, urethane NH); 8.33 (1H, d, J=7.5 Hz, amide NH); 10.8 (1H, s, indole NH); MS m/e (CI) 442 [M$^+$].

EXAMPLE 7

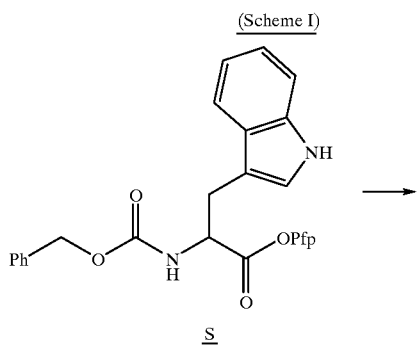

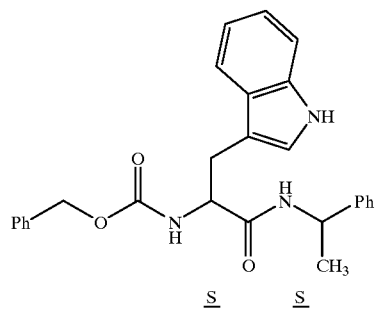

Example 5, Scheme I, but using (S)-(−)-α-methylbenzylamine method as described for Example 5, Scheme I. Recrystallization from ethyl acetate gave (0.057 g, 13%); mp 168–170° C.;

$[\alpha]_D^{23}$=−11.6 (c=0.5, MeOH); IR (film): 3294, 1704 (urethane CO), 1656 (amide I) and 1536 cm$^{-1}$ (amide II); NMR (DMSO-d$_6$): δ 1.35 (3H, d, J=6.9 Hz, CH$_3$); 2.86 (1H, d.d, J=9.2 and 14.3 Hz, one of βCH$_2$); 3.06 (1H, d.d, 5=4.8 and 14.3 Hz, one of βCH$_2$); 4.36 (1H , m, CH(CH$_3$)Ph); 4.90–4.96 (3H, m, PhCH$_2$, Trp αCH); 6.94–7.35 (15H, m, aromatics); 7.63 (1H, d, J=7.9 Hz, urethane NH); 8.41 (1H, d, J=7.7 Hz, amide NH); 10.8 (1H, s, indole NH); MS m/e (CI) 442 [M$^+$].

EXAMPLE 8

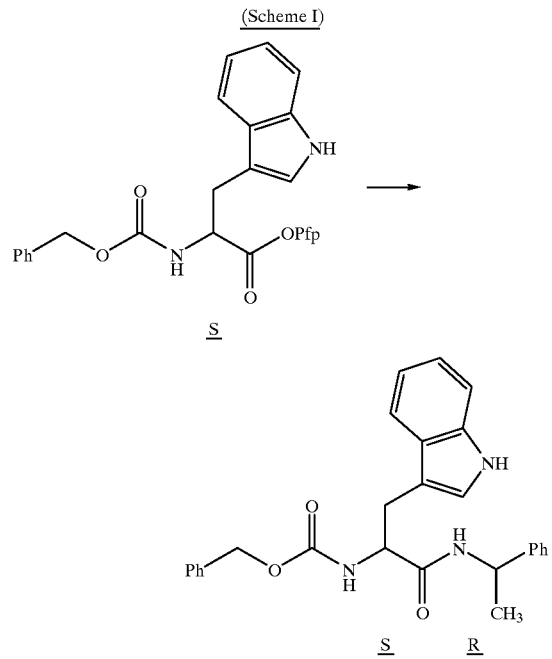

CBZ-S-Trp pentafluorophenyl ester (0.50 g, 1 mmol) was prepared in situ, then dissolved in ethyl acetate and (R)-(+)-α-methylbenzylamine (0.13 mL, 1 mmol) was added. The reaction mixture was stirred at rock temperature until no starting material remained. The white precipitate was collected by filtration and purified by chromatography to give the product (0.077 g, 17%); mp 160–163° C.;

$[\alpha]_D^{23}$=+24.4 (c=0.5, MeOH); IR (film): 3307, 1704 (urethane CO), 1657 (amide I) and 1517 cm$^{-1}$ (amide II);

NMR (DMSO-d$_6$): δ 1.24 (3H, d, J=7.0 Hz, CH$_3$); 2.95 (1H, d.d, J=9.4 and 14.3 Hz, one of βCH$_2$); 3.08 (1H, d.d, J=5.4 and 14.3 Hz, one of βCH$_2$); 4.32 (1H, m, C$\underline{H}$(CH$_3$)Ph); 4.86–4.94 (3H, m, PhC$\underline{H}_2$, Trp αCH); 6.95–7.34 (15H, m, aromatics); 7.63 (1H, d, J=7.7 Hz, urethane NH); 8.32 (1H, d, J=7.8 Hz, amide NH); 10.8 (1H, s, indole NH); MS me (CI) 442 M$^+$.

EXAMPLE 9

(Scheme II)

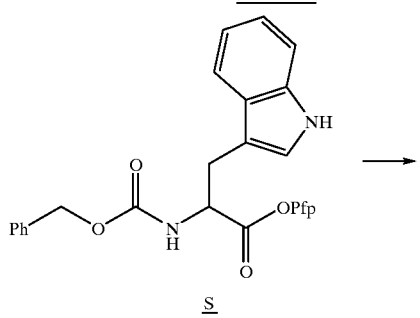

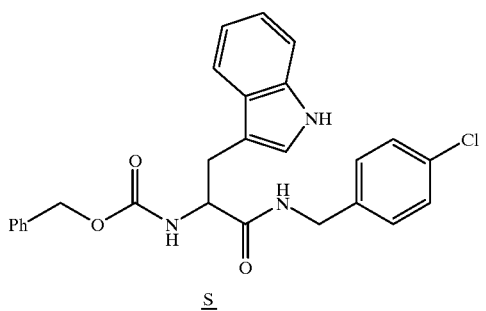

Method as described for Example 3, Scheme I, but using 4-chlorobenzylamine. Yield (0.05 g, 11%); mp 177–179° C.;

[α]$_D^{23}$=+10.8 (c=0.5, MeOH); IR (film): 3291, 1704 (urethane CO), 1658 (amide II), and 1535 cm$^{-1}$ (amide I); NMR (DMSO-d$_6$): δ 2.95 (1H, d.d, J=9.1 and 14.5 Hz, one of Trp βCH$_2$); 3.13 (1H, d.d, J=5.3 and 14.5 Hz, one of Trp βCH$_2$); 4.20–4.36 (3H, m, αCH, NHC$\underline{H}_2$); 4.97 (2H, s, PhC$\underline{H}_2$O); 6.94–7.46 (14H, m, aromatics); 7.62 (1H, d, J=7.8 Hz, urethane NH); 8.52 (1H, bt, amide NH); 10.8 (1H, s, indole NH); MS m/e (CI) 462 M$^+$.

EXAMPLE 10

(Scheme II)

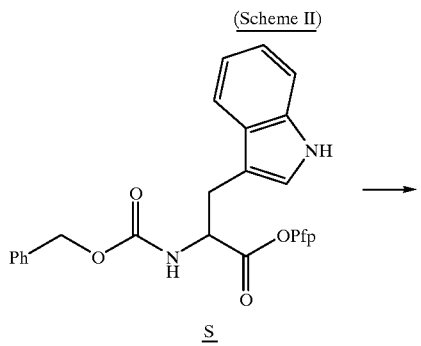

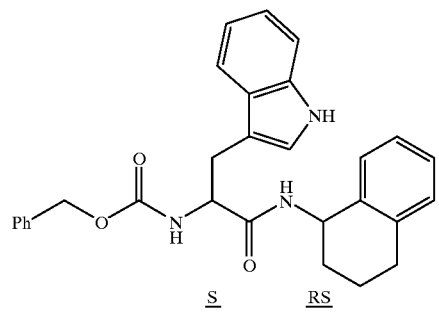

Method as described for Example 3, Scheme I; but using 1,2,3,4-tetrahydro-1-napthylamine. Yield. (0.298 g, 64%); mp 73–76° C.;

IR (film): 3298–2863, 1707 (urethane CO), 1651 (amide I) and 1538 cm$^{-1}$ (amide II); NMR (DMSO-d$_6$): δ 1.52–1.87 (4H, m, CH$_2$CH$_2$); 2.70 (2H, m, CH$_2$C$\underline{H}_2$Ph); 2.91–3.16 (2H, m, Trp βCH$_2$); 4.32 (1H, m, αCH); 4.96 (3H, m, PhC$\underline{H}_2$, NHC$\underline{H}$Ph); 6.74–7.37 (14H, m, aromatics); 7.63 (1H, m, urethane NH); 8.21 (½H, d, J=9.4 Hz, amide NH); 8.32 (½H, d, J=8.8 Hz, amide NH); 10.81, 10.79 (1H, 2×s, indole NH); MS m/e (CI) 468 [M$^+$].

EXAMPLE 11

(Scheme II)

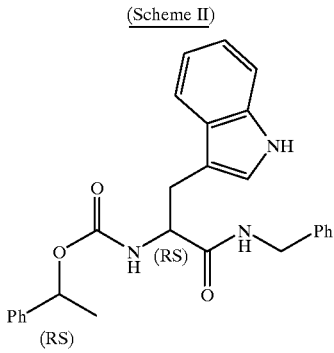

A solution of (RS) sec-phenethyl alcohol (2 g, 0.0163 mol) and dry pyridine (1.3 mL, 0.0163 mol) in dry dichloromethane (10 mL) was cooled to 0° C. A solution of 4-nitrophenyl chloroformate (3.28 g, 0.0163 mol) in dry dichloromethane (25 mL) was added dropwise over 15 minutes and the resulting solution stirred at room temperature for 15 hours. The solvent was removed in vacuo (the temperature being kept below 30° C.) and ether (50 mL) was added and the precipitate was removed by filtration. The solvent was removed in vacuo below 30° C. to give the crude mixed carbonate, vmax 1765 cm$^{-1}$ (c=0), which was used without further purification.

R,S-Tryptophan benzylamide (0.5 g, 0.0018 mol) and triethylamine (0.18 mL, 0.0018 mol) were dissolved in dry DMF (5 mL). A solution of the mixed carbonate (0.52 g, 0.0025 mol) in DMF (5 mL) was added dropwise over 5 minutes, there was an immediate yellow coloration upon addition of the mixed carbonate, and the yellow solution was stirred at room temperature for 5 hours. The reaction mixture was poured into water (50 mL) and extracted with EtOAc (3×10 mL). The organic phase was washed with dilute aqueous NaOH (approx. 1 M) until the disappearance of the yellow color (approx. 5×20 mL) and then with saturated aqueous citric acid (5×20 mL), water (10 mL), brine (20 mL), dried (MgSO$_4$), and the solvent removed. in vacuo. The crude product was purified by column chromatography, eluting with dichloromethane:ethanol (9:1) to give the urethane, Example 11, Scheme II, as a white solid (0.61 g, 77%); mp 128–132° C.; IR (film): 3317 (NH), 1706 (C=O, carbamate), 1659 (C=O, amide), 1497, 1456, 1378, and 1355 cm$^{-1}$; NMR (DMSO-d$_6$): 1.35 and 1.4 (3H, d, J=7 Hz, CHC$\underline{H}_3$); 2.8–3.2 (2H, m, IndC$\underline{H}_2$), 4.3 (3H, m, CONHC$\underline{H}_2$Ph, CH); 5.1 (1H, m, PhC$\underline{H}$O); 6.9–7.3 (15H, aromatics and carbamate NH); 7.6 (1H, m, 4H-indole); 8.45 (1H, m, amide NH); 10.7 (1H, m, indole N$\underline{H}$); Ms m/e (CI): 442 (M$^+$+H).

EXAMPLE 12

(Scheme III)

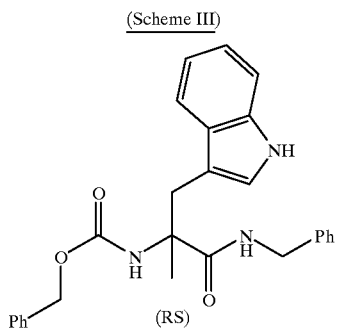

Benzyl chloroformate (0.85 mL, 0.005 mol) was added in one portion to a vigorously stirred suspension of R,S-α-Me-Trp methyl ester (1 g, 0.0043 mol) and potassium carbonate (2 g, 0.015 mol) in dioxane (15 mL) and water (1 mL). The mixture was stirred at room temperature for 2 hours, after which time t.l.c. analysis indicated the consumption of starting material. The solvent was removed in vacuo. The residue was treated with 2 M hydrochloric acid (10 mL), water (40 mL), and extracted with EtOAc (3×20 mL). The organic phase was washed with water (2×20 mL), brine (10 mL), dried (MgSO$_4$), and the solvent removed in vacuo to give the N-protected amino ester as an off-white solid (1.39 g, 87%) which was used in the next reaction without further purification.

υmax (film): 3345 br (NH), 1718 br (C=O, ester and carbamate) cm$^{-1}$. δ (CDCl$_3$): 1.63 (3H, s, α-CH$_3$); 3.60 (5H, br.m, OCH$_3$ and CH$_2$-Ind); 5.08 (2H, m, ArCH$_2$O); 5.5 (1H, br.s, NH urethane); 6.8–7.5 (11H, aromatics); 8.3 (1H, br.s, N$\underline{H}$ indole).

A mixture of this ester (1.49 g, 0.004 mol) and lithium hydroxide monohydrate (0.84 g, 0.02 mol) in THF (15 mL) and water (5 mL) was stirred vigorously at room temperature for 15 hours. The solution was extracted with EtOAc (3×10 mL) and the organic phase discarded. The aqueous phase was acidified with 2 M hydrochloric acid (approx. 20 mL) and extracted with EtOAc (3×20 mL). The organic phase was washed with water (20 mL), brine (20 mL), dried (MgSO$_4$), and the solvent removed in vacuo to give the acid (Scheme III) as a light brown oil (1.31 g, 88%) which was used in the next step without further purification.

υmax (film): 3389 (OH), 1770 (C=O, acid), and 1708 (C=O, carbamate) cm$^{-1}$.

This crude carboxylic acid (1.1 g, 0.003 mol), N,N'-dicyclohexylcarbodiimide (DCC) (0.618 g, 0.003 mol) and pentafluorophenol (PFP) (0.6 g, 0.0033 mol) were dissolved in EtOAc (20 mL) and the reaction mixture stirred at room temperature for 1 hour. The mixture was filtered to remove the white solid and benzylamine (0.35 mL, 0.0033 mol) was added and the mixture stirred for 10 hours at room temperature. The solvent was removed in vacuo and the crude product was purified by column chromatography, eluting with dichloromethane:methanol (8:2), gigging the benzamide, Example 12, Scheme III, as a white solid (0.97 g, 73%); mp 117–119° C.;

IR (film): 3337 (NH), 1709 (C=O, carbamate), 1657 (C=O, amide), 1517, 1456, and 1352 cm$^{-1}$; NMR (DMSO-d$_6$): 1.37 (3H, s, α-Me); 3.33 (2H, m, Ind-C$\underline{H}_2$); 4.28 (2H, d, J=5 Hz, NC$\underline{H}_2$Ph); 5.04 (2H, m, Ph–C$\underline{H}_2$O); 6.9–7.5 (16H, aromatics and carbamate); 8.2 (1H, br.s, amide NH); 10.83 (1H, s, indole N$\underline{H}$); MS m/e (CI); 442 (M$^+$+H).

EXAMPLE 13

(Scheme III)

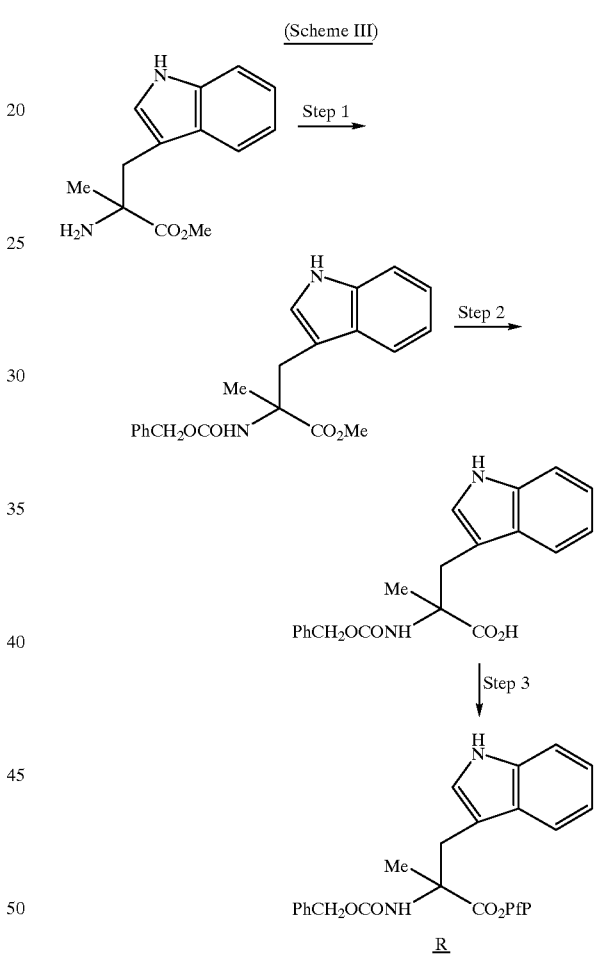

Step 1

A solution of R-α-methyl tryptophan methylester (37.16 g, 160.0 mmol) in dry THF (800 mL) and triethylamine (19.43 g, 192 mmol) was cooled to 0° C. and treated with benzylchloroformate (30.03, 176 mmol) in dry THF (200 mL) dropwise. This was allowed to warm to room temperature slowly, then the solvent removed in vacuo. The residue was redissolved in EtOAc (500 mL), washed with H$_2$O (500 mL), 2N HCl (500 mL), saturated NaHCO$_3$ solution (500 mL), then H$_2$O (500 mL). The organic phase was dried over MgSO$_4$, filtered, and evaporated to dryness in vacuo. The residue was purified by silica gel chromatography using 60% Et$_2$O in n-hexane as eluant to give the product.

[α]$_D^{20}$=+31.7° (c=1, MeOH);

Step 2

The CBZ-αMe-R-tryptophan methyl ester (69.15 g, 150 mmol) was dissolved in THF (800 mL), cooled to 0° C., and treated with LiOH (30 g in 250 mL H₂O). MeOH was added (150 mL) and the mixture stirred for 3 hours. The solvent was removed in vacuo. The residue was diluted with H₂O (500 mL) and extracted with CF₂Cl₂ (2×300 mL). The aqueous phase was acidified using 2 M citric acid and extracted with CH₂Cl₂ (2×500 mL). The organic phase was washed with water, dried (MgSO₄), and filtered and evaporated to dryness to give the crude acid, 57.5 g (2:1 mix acid:ester). This crude material was used in Step 3.

Step 3

The crude carboxylic acid from Step 2 above was redissolved in EtOAc (320 mL) and treated with pentafluorophenol (21 g, 114 mmol), followed by the dropwise addition of a solution of N,N'-dicyclohexylcarbodiimide (23.5 g, 114 mmol) in EtOAc (150 mL). This was stirred 18 hours at room temperature. The reaction mixture was then filtered, and the filtrate evaporated to dryness. The solid residue was redissolved in CH₂Cl₂ (200 mL) and absorbed onto silica, and purified by chromatography using 50% EtOAc in n-hexane to give the product 49.77 g (64%) from α-methyl-R-tryptophan methylester;

IR (film): 1785, 1709, and 1520 cm⁻¹; NMR (CDCl₃): δ 1.72 (3H, s); 3.44 (1H, d, J=14.7 Hz); 3.66 (1H, d, J=14.7 Hz); 5.15 (2H, m,); 5.22 (1H, br.s); 6.97 (1H, d, J=2 Hz); 7.09 (1H, t, J=7.5 Hz); 7.22 (1H, t, J=8.0 Hz, 7.34 (6H, m); 7.58 (1H, d, J=7.9 Hz); 8.11 (1H, br.s).

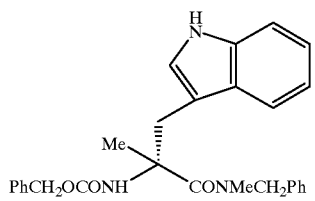

A solution of CBZ-α-methyl-R-tryptophan pentafluorophenyl ester (250 mg, 0.50 mmol) in EtOAc (50 mL) was treated with N-benzylmethylamine (900 mg, 7.40 mmol) and stirred at room temperature for 18 hours. This mixture was washed with 2N HCl (50 mL), then H₂O (50 mL). The organic phase was dried (MgSO₄), filtered, and evaporated to give a crude residue which was purified by reverse-phase chromatography using 50% MeOH in H₂O as eluant to give the product as a white foam (40 mg, 18%); mp 64–68° C. (MeOH/H₂O);

IR (nujol mull): 1703 and 1620 cm⁻¹; NMR (DMSO-d₆): δ 1.30 (3H, s); 2.90 (3H, brs); 3.20 (1H, d, J=14 Hz); 3.50 (1H, d, J=14 Hz); 4.60 (2H, br); 5.00 (2H, br); 6.8–7.6 (16H, m); 10.9 (1H, br.s); MS (CI) m/e 456 (11, M⁺+H), 335 (30), 304 (48) 263 (4.5), 91 (100); Analysis calculated for C, H, N; $C_{23}H_{29}N_3O_3 \cdot 0.25 CCl_4$: C, 68.68; H, 5.92; N, 8.51. Found: C, 68.68; H, 5.90; N, 8.38.

EXAMPLE 14

(Scheme III)

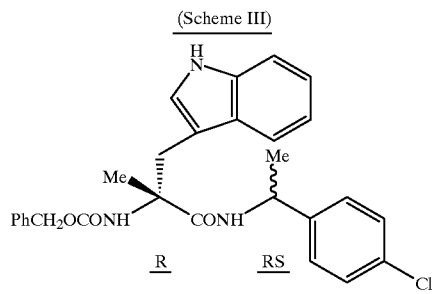

A solution of CBZ-α-methyl-R-tryptophan pentafluorophenyl ester (1000 mg, 1.929 mmol) in EtOAc (50 mL) was treated at room temperature with 4 chloro-α-methylbenzylamine (1100 mg, 7.069 mmol) for 1 hour with stirring. The reaction mixture was then washed with 2N HCl (80 mL), then H₂O (100 mL). The organic phase was dried over MgSO₄, filtered, and evaporated to dryness in vacuo. The residue was purified by chromatography using 20% Et₂O in CH₂Cl₂ as eluant to give the product as a white foam and a 1:1 mixture of diastereoisomers (820 mg, 87%); mp 56–58° C. (Et₂O/CH₂Cl₂);

IR (nujol mull): 710 and 1651 cm⁻¹; NMR (DMSO-d₆): δ 1.20–1.40 (6H, m); 3.10–3.50 (2H, m); 4.80 (1H, m); 5.00 (2H, s); 6.80–7.50 (14H, m); 7.90 1H, d, J=8 Hz); 8.1 (1H, d, J=8 Hz); 10.80 (1H, s).

EXAMPLE 15

(Scheme III)

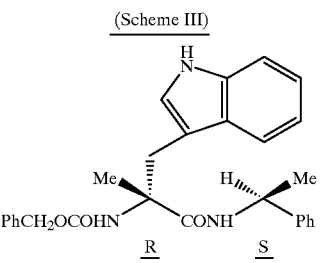

A solution of CBZ-α-methyl-R-tryptophan pentafluorophenyl ester (730 mg, 1.40 mmol) in EtOAc (15 mL) was treated with S(−)-α-methylbenzylamine (940 mg, 7.76 mmol) and left stirring at room temperature for 1 hour. The mixture was washed with 2 M HCl (20 mL) then H₂O (20 mL). The organic phase was dried over MgSO₄, filtered, and evaporated to dryness in vacuo. The residue was then subject to reverse phase chromatography using 80% MeOH; 20% H₂O as eluant to give the product as a white foam (150 mg, 24%); mp 107–109° C. (H₂O/MeOH);

$[\alpha]_D^{20}$=+13° (c=0.5, MeOH); IR (film): 3460–3400, 1711, 1658, 1495, and 1251 cm⁻¹; NMR (DMSO-d₆): δ 1.32 (3H, d, J=7 Hz); 1.38 (3H, s); 3.20–3.40 (2H, m); 4.90 (1H, m); 5.00 (2H, s); 6.80 (1H, s); 6.90 (1H, t, J=7 Hz); 7.00 (1H, t, J=7 Hz); 7.01–7.40 (12H, m); 7.50 (1H, d, J=8 Hz); 8.00 (1H, d, J=8 Hz); 10.80 (1H, s); MS (CI) 456 (30, M⁺+H), 130 (100), 91 (57), 105 (33). Analysis calculated for C, H, N, $C_{28}H_{29}N_3O_3 \cdot 0.5 H_2O$: C, 72.39; H, 6.51; N, 9.04%. Found: C, 72.53; H, 6.48; N, 8.98%.

EXAMPLE 16

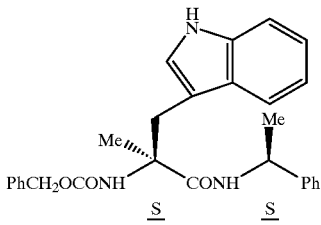

Method as for Example 15, Scheme III except using CBZ-α-methyl-S-tryptophan pentafluorophenyl ester (142 mg, 23%); mp 107–110° C. (MeOH:H₂O);

IR (film): 3327, 1716, and 1653 cm⁻¹; NMR (DMSO-d₆): δ 1.20–1.40 (6H, m); 3.10–3.40 (2H, m); 4.90 (1H, m); 5.00 (2H, s); 6.80–7.50 (16H, m); 7.90 (1H, d, J=8 Hz); 10.80 (1H, br.s). Analysis calculated for C, H, N, $C_{28}H_{29}N_3O_3 \cdot 0.25H_2O$: C, 73.10; H, 6.46; N, 9.13%. Found: C, 73.40; H, 6.41; N, 9.18%.

EXAMPLE 17

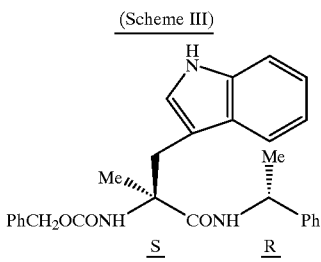

Method as for Example 15, Scheme III except using CBZ-α-methyl-S-tryptophan pentafluorophenyl ester and R(+)-α-methylbenzylamine (190 mg, 30%); mp 109–111° C. (MeOH/H₂O);

$[\alpha]_D^{24}$=−13.2° (c=0.5, MeOH); IR (film): 1719 and 1654 cm⁻¹; NMR (DMSO-d₆): 1.34 (3H, d, J=7.9 Hz); 1.39 (3H, s); 3.28–3.36 (2H, m); 4.92 (1H, m); 5.04 (2H, s); 6.82 (1H, s); 6.87 (1H, br); 6.93 (1H, t, J=7.6 Hz); 7.02 (1H, t, J=7.0 Hz); 7.22–7.47 (11H, m); 7.50 (1H, d, J=7.8 Hz); 8.02 (1H, d, J=8.2 Hz); 10.8 (1H, s); MS (CI) m/e 456 (25, M⁺+H), 130 (100), 91 (73), 105 (35), 304 (29); Analysis calculated for C, H, N, $C_{28}H_{29}N_3O_3 \cdot 0.25H_2O$: C, 73.10; H, 6.46; N, 9.13%. Found: C, 73.27; H, 6.45; N, 9.22%.

EXAMPLE 18

(Scheme III)

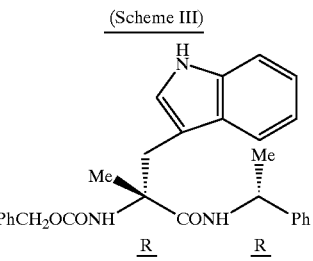

Method as for Example 15, Scheme III, except using (R)(+)α-methylbenzylamine (150 mg, 24%); mp 63–68° C. (MeOH/H₂O);

$[\alpha]_D^{28}$=+9.4° (c=0.5, MeOH); IR (film): 17H, 1658 cm⁻¹; NMR (DMSO-d₆): δ 1.28 (3H, d, J=6.8 Hz); 1.34 (3H, s); 3.16–3.30 (2H, m); 4.89 (1H, m); 5.04 (2H, s); 6.89 (1H, s); 7.00 (1H, t, J=7.9 Hz); 7.20–7.45 (13H, m); 7.48 (1H, d, J=7.8 Hz); 7.88 (1H, d, J=7.5 Hz); 16.80 (1H, s); MS (CI) m/e 456 (20, M⁺+H), 130 (100, 191, 150).

EXAMPLE 19

(Scheme IV)

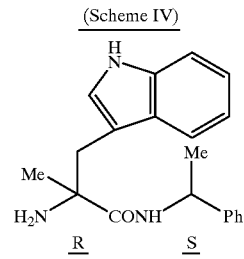

A solution of Example 15, Scheme III (17 g, 37 mmol) in EtOH (200 mL) was treated with 20% Pd(OH)₂ (1 g, 6% w/w) and put under an atmosphere of hydrogen at 30° C. at a pressure of 45 psi for 3 hours. The reaction mixture was then filtered and evaporated to dryness in vacuo, the residue was purified by SiO₂ chromatography using 0.5% NH₄OH, 5% MeOH, 94.5% CH₂Cl₂ as eluant to give the product (8.1 g, 62%);

mp 124.5–125° C.; $[\alpha]_D^{20}$=+7.0° (c=1, MeOH); IR (film): 1643, 1512, and 1454 cm⁻¹; NMR (CDCl₃): δ 1.42 (3H, d, J=6.9 Hz); 1.46 (3H, s); 1.53 (2H, br.s); 2.81 (1H, d, J=14.2 Hz); 3.46 (1H, d, J=14.2 Hz); 5.02 (1H, dq, J=7 Hz); 6.71 (1H, d, J=2.2 Hz); 7.17 (7H, m); 7.33 (1H, d, J=8.0 Hz); 7.59 (1H, d, J=7.8 Hz); 7.82 (1H, d, J=8 Hz); 8.02 (1H, s); MS (CI) m/e 322 (100, M⁺+H); Analysis calculated for C, H, N, $C_{20}H_{23}N_3O$: C, 74.74; H, 7.21; N, 13.07%. Found: C, 74.7; H, 7.25; N, 13.04%.

Step 7

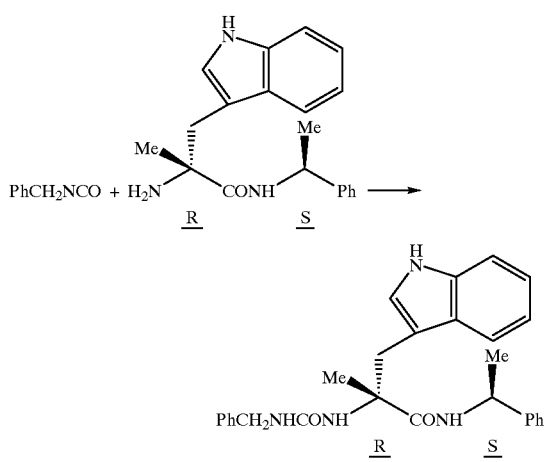

To a stirred solution of the amine (Scheme IV) (321 mg, 1.0 mmol) in THF (10 mL) was added a solution of benzyl isocyanate (146 mg, 1.1 mmol) in THF (5 mL) dropwise. After 1 hour, the solvent was removed in vacuo and the residue chromatographed using 4% MeOH/CH$_2$Cl$_2$. Crystallization from ether gave product (404 mg, 89%); mp 184–187° C.;

$[\alpha]_D^{20}$=27° (c=1, MeOH); IR (film): 3500–3200 (NH), 1646 (broad, CO, urea and amide), 1557, 1455, 1265, 741, and 700 cm$^{-1}$; NMR (CDCl$_3$): δ 1.28 (3H, d, J 6.9 Hz, CHC$_3$); 1.48 (3H, s, CC$\underline{H}_3$); 3.11 (1H, d, J=14.6 Hz, one of C$\underline{H}_2$indole); 3.41 (1H, d, J=14.6 Hz, one of CH$_2$indole); 4.14 (1H, d, J=15.1 and 5.8 Hz, one of C$\underline{H}_2$Ph); 4.24 (1H, dd, H=15.1 and 5.9 Hz, one of CH$_2$Ph); 4.82–4.92 (1H, m, C$\underline{H}$CH$_3$); 5.12 (1H, s, CH$_2$NHCONH); 5.20–5.30 (1H, m, CH$_2$N$\underline{H}$CONH); 6.74 (1H, d, J=2.2 Hz, indole, C$_2$H); 7.00–7.30 (14H, m, aromatics and CON$\underline{H}$CH); 7.51 (1H, d, J=7.7 Hz, indole C$_4$-H); 8.22 (1H, s, indole NH); MS m/e (CI$^+$): 455 (52) (M$^+$+H), 348 (11), 334 (27), 322 (100), 304 (49), 173 (47), 131 (25), 130 (61), 105 (40), 91 (85); Analysis calculated for C, H, N.

EXAMPLE 20 (Scheme V)

Step 8

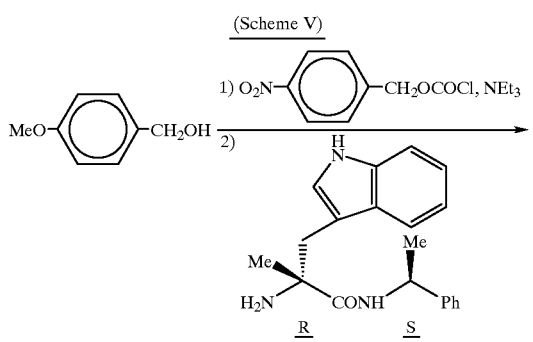

-continued

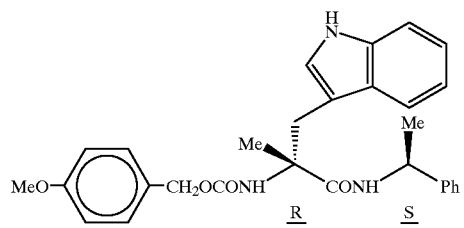

1) To a stirred solution of 4 nitrophenylchloroformate (2.01 g, 10 mmol) in acetone (30 mL), cooled in an ice bath, was added 4-methoxybenzylalcohol (1.38 g, 10 mmol) followed by the dropwise addition of a solution of triethylamine (1.01 g, 10 mmol) in acetone (10 mL). Left to stir overnight, filtered off triethylaminehydrochloride, solvent removed under vacuum. Residue taken up in ethyl acetate (50 mL), washed with citric acid solution (2×30 mL), sodium carbonate solution (5×30 mL), brine (2×30 mL), dried over MgSO$_4$, and solvent removed in vacuo. Crystallization from ether gave carbonate (2.7 g, 89%);

mp 99–100° C.; IR (film): 1747 (CO, carbonate), 1617, 1519, 1353, 1279, 1255, 1034, 866 cm$^{-1}$; NMR (CDCl$_3$): δ 3.83 (3H, s, C$\underline{H}_{3O}$); 5.24 (2H, s, C$\underline{H}_2$O);

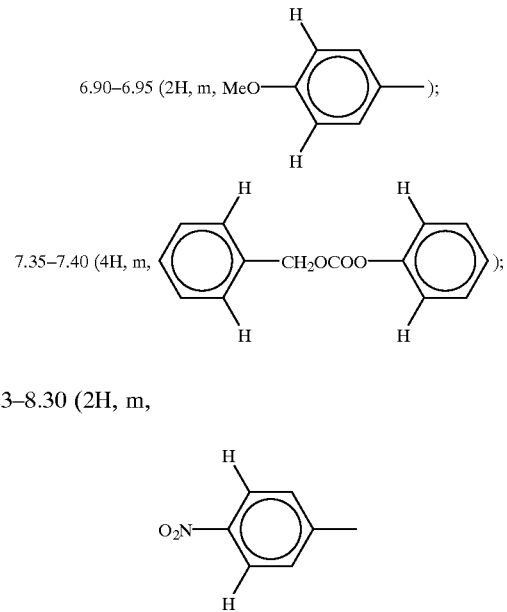

; MS m/e (CI+): 303 (10) (M$^+$+H), 277 (2), 260 (5), 241 (3), 149 (9), 140 (61), 122 (44), 121 (100); Analysis calculated for C, H, N.

2) A solution of carbonate (364 mg, 1.2 mmol), the amine (321 mg, 1.0 mmol), and 4-dimethylamino-pyridine (122 mg, 1.0 mmol) in DMF (20 mL) was stirred overnight before solvent was removed under vacuum. Residue taken up in ethyl acetate (50 mL) and washed with citric acid solution (2×50 mL), brine (30 mL), 2N NaOH solution (5×50 mL), brine (30 mL), dried over MgSO$_4$, filtered, and solvent removed under vacuum. Residue chromatographed using 2% MeOH/CHCl$_2$ and crystallization from ether gave product (360 mg, 80%); mp 86–94° C.;

$[\alpha]_D^{17}$=+16.7° (c=1, MeOH); IR (film): 3500–3200 (NH), 1713 (CO, urethane), 1652 (CO, amide), 1614, 1515, 1457, 1246, 1176, 1070, 822, 742, and 701 cm$^{-1}$; NMR (CDCl$_3$):

δ 1.31 (3H, d, J=6.9 Hz, CHC$\underline{H}_3$); 1.60 (3H, s, CCH$_3$); 3.24 and 3.46 (each 1H each d, J=14.7 Hz, each one of C$\underline{H}_2$indole); 3.79 (3H, s, OMe); 4.95–5.05 (3H, m, C$\underline{H}_2$OCONH and CONHC$\underline{H}$); 5.27 (1H, s, OCONH); 6.35–6.45 (1H, br.d, CON$\underline{H}$CH); 6.75 (1H, s, indole C$_2$-H); 6.85 (2H, d, J=8.6 Hz, ortho protons to OMe group); 7.09 (1H, t, J=7.4 Hz, indole C$_5$ or C$_6$-H); 7.15–7.30 (8H, m, CH$_2$Ph, indole C$_5$ or C$_6$H, meta protons to OMe group); 7.33 (1H, d, J=8.0 Hz, indole C$_7$-H); 7.57 (1H, d, J=7.8 Hz, indole C$_4$-H); 7.95 (1H, s, indole NH); Analysis calculated for C, H, N.

EXAMPLE 21 (Scheme IV)
Step 9

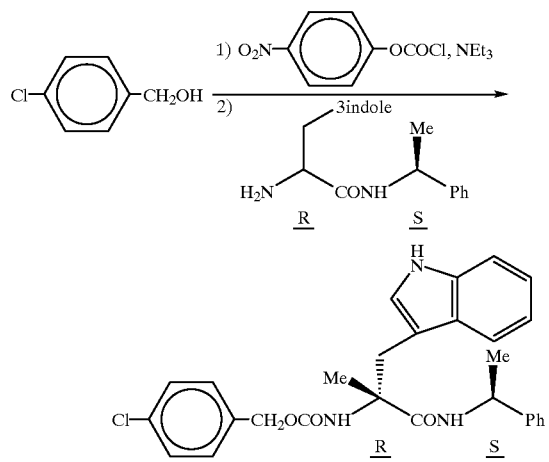

1) Method as for Example 20, Scheme IV, except used 4-chlorobenzyl alcohol (1.42 g, 10 mmol) to give a crystalline carbonate (2.9 g, 94%) from ether;

mp 135–138° C.; IR (film): 1761 (CO, carbonate), 1524, 1492, 1350, 1261, 1215 cm$^{-1}$; NMR (CDCl$_3$): δ 5.26 (2H, s, CH$_2$O); 7.35–7.40 (6H, m, aromatics); 8.25–8.30 (2H, m,

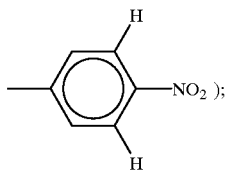

MS m/e (CI$^+$): 308 (6) (M$^+$+H), 292 (4), 278 (7), 266 (15), 264 (41), 140 (43), 127 (82), 125 (100); Analysis calculated for C, H, N, Cl.

2) Method as for Example 20, Scheme IV , except used 4-chlorobenzyl carbonate (368 mg, 1.2 mmol). Chromatography using 3% MeOH/CH$_2$C$_2$ followed by crystallization from ether gave a crystalline product (434 mg, 89%-); mp 98–100° C.;

[α]$_D^{20}$=+12.50 (c=1, MeOH); IR (film): 3450–3200 (NH), 1712 (CO, urethane), 1651 (CO, amide), 1494, 1457, 1251, 1073, 742, and 700 cm$^{-1}$; NMR (CDCl$_3$): δ 1.29 (3H, d, J=6.9 Hz, CHC$\underline{H}_3$); 1.63 (3H, s, CC$\underline{H}_3$); 3.26 (1H, d, J=14.8 Hz, one of CH$_2$indole); 3.45 (1H, d, J=14.8 Hz, one of CH$_2$indole); 4.95–5.05 (3H, m, CH$_2$O and C$\underline{H}$CH$_3$); 5.43 (1H, s, OCONH); 6.27 (1H, d, J=7.5 Hz); 680 (1H, s, indole, C$_2$-H); 7.05–7.30 (11H, m, CHP$\underline{h}$, Cl—A$\underline{r}$, indole C$_5$ and C$_6$-H); 7.34 (1H, d, J=8.0 Hz, indole C$_7$-H); 7.58 (1H, d, J=7.9 Hz, indole C$_4$-H); 8.01 (1H, s, indole NH); Analysis calculated for C, H, N.

EXAMPLE 22 (Scheme (IV)
Step 10

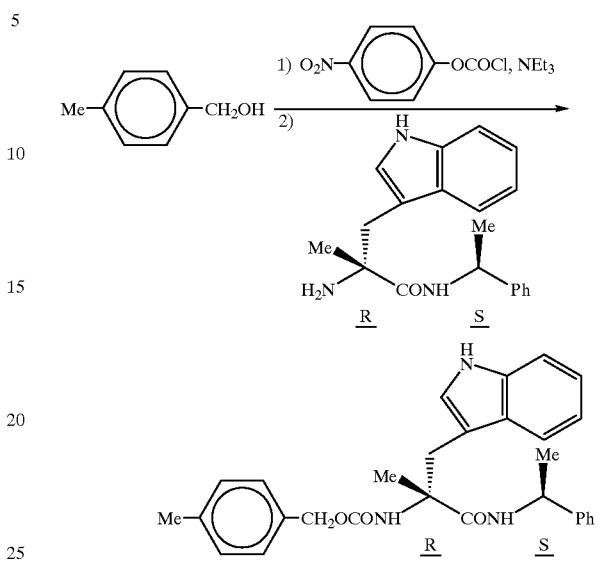

1) Method as for Example 20, Scheme IV except used α-methylbenzylalcohol (1.22 g, 10 mmol) to give a crystalline carbonate (2.3 g, 80%) for ethyl acetate;

mp 93–95° C.; IR (film): 1750 (CO, carbonate), 1536, 1349, 1268, 1218, 865 cm$^{-1}$; NMR (CDCl$_3$): δ 2.37 (3H, s, CH$_3$); 5.26 (2H, s, C$\underline{H}_2$O); 7.15–7.40 (6H, m, aromatics); 8.24–8.30 (2H, m,

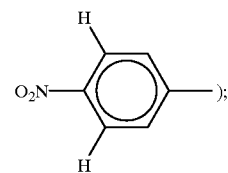

MS m/e (CI$^+$): 288 (6) (M$^+$+H); 244 (41), 239 (12), 198 (49), 140 (36), 122 (25), 106 (51), 105 (100); Analysis calculated for C, H, N.

2) Method as for Example 20, Scheme IV, except used 4-methylbenzylcarbonate (345 mg, 1.2 mmol). Residue chromatographed using 2% MeOH/CH$_2$Cl$_2$ and crystallization from ether gave product (350 mg, 75%);

mp 85–95° C. (Needles); [α]$_D^{24}$=+15.5° (c=1, MeOH); IR (film): 3500–3200 (NH, 3059, 3028, 2977, 2930, 1709 (CO, urethane), 1652 (CO, amide), 1494, 1457, 1251, 1071, 742, and 700 cm$^{-1}$; NMR (CDCl$_3$): δ 1.30 (3H, d, J=6.9 Hz, CHC$\underline{H}_3$); 1.61 (3H, s, CC$\underline{H}_3$); 2.34 (3H, s, Me-aryl); 3.24 (1H, d, J=14.7 Hz, one of CH$_2$indole); 3.46 (1H, d, J=14.8 Hz, one of CH$_2$indole); 4.95–5.07 (3H, m, C$\underline{H}_2$O and C$\underline{H}$CH$_3$); 5.31 (1H, s, OCONH); 6.38 (1H, d, J=7.7 Hz, CON$\underline{H}$CH); 6.77 (1H, d, J=2.2 Hz, indole C$_2$-H); 7.05–7.30 (11H, m, CHPh, pMe-Ph, indole C$_5$ and C$_6$-H); 7.33 (1H, d, J=8.1 Hz, indole C$_7$-H); 7.58 (1H, d, J=7.7 Hz, indole C$_4$-H); 7.98 (1H, s, indole NH); Analysis calculated for C, H, N.

EXAMPLE 23

(Scheme V)

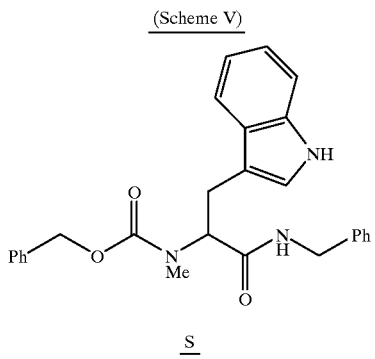

Benzylchloroformate (0.85 mL, 0.005 mol) was added in one portion to a vigorously stirred suspension of S-abrine (1 g, 0.0040 mol), potassium carbonate (1.2 g, 0.009 mol) in dioxane (15 mL) and water (1 mL). The mixture was stirred at room temperature for 1 hour, after which time t.l.c. analysis indicated the consumption of starting material. The solvent was removed in vacuo. The residue was treated with 2 M hydrochloric acid (20 mL), water (40 mL), and extracted with EtOAc (3×30 mL). The organic phase was washed with water (10 mL), brine (2×10 mL), dried ($MgSO_4$), and the solvent removed in vacuo to give the N-protected amino acid (Scheme V) as a dark straw-colored oil (1.25 g, 77%) which was used in the next reaction without further purification; υmax (film): 3345 br (OH), 1740 shoulder (C=0 acid) and 1684 $cm^{-1}$ v. broad (C=0, carbamate).

The carboxylic acid (0.85 g, 0.0024 mol), N,N'-dicyclohexylcarbodiimide (DCC) (0.56 g, 0.0024 mol) and pentafluorophenol (PFP) (0.44 g, 0.0027 mol) were dissolved in EtOAc (20 mL) and the reaction mixture stirred at room temperature for 1 hour. The mixture was filtered to remove the white solid. Benzylamine (0.3 mL, 0.0026 mol) was added and the mixture stirred for 10 hours at room temperature. The solvent was removed in vacuo and the crude product was purified by column chromatography, eluting with dichloromethane:methanol (9:1) giving Example 23 as a white solid (0.66 g, 63%); mp 48–54° C.;

IR (film): 3326 (NH), 1695 (shoulder, C=0, carbamate), 1662 (C=0, amide), 1547, 1497, and 1402 $cm^{-1}$; NMR (DMSO-$d_6$): 2.88 (3H, br.s, $NHCH_3$); 3.10 (1H, br, m, CH $_aH_bInd$); 3.33 (1H, m, $CH_aH_bInd$); 4.32 (2H, d, J=6 Hz, $NHCH_2Ph$); 4.8–5.2 (3H, m, $ArCH_2O$ and CH); 6.8–7.7 (15H, m, aromatics and carbamate NH); 8.65 (1H, s, br, amide NH); 10.85 (1H, s, indole NH); MS m/e (CI) 442 ($M^++H$).

EXAMPLE 24

(Scheme V)

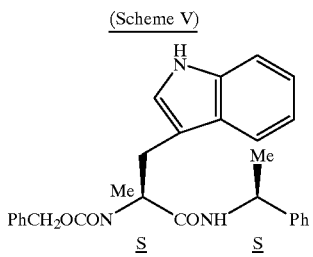

A solution of CBZ-S-abrine pentafluorophenyl ester (100 mg, 0.20 mmol) in EtOAc (10 mL) was treated with S-(–)-α-methylbenzylamine (470 mg, 4.00 mmol) at room temperature for 10 minutes with stirring. The mixture was then washed with diluent HCl (20 mL) then $H_2O$ (20 mL). The organic phase was dried over $MgSO_4$, filtered, and evaporated to dryness in vacuo. The residue was purified by chromatography using 10% $Et_2O$:90% $CH_2Cl_2$ as eluant to give the product as a white foam (68 mg, 77%); mp 58–60° C. ($Et_2O/CH_2Cl_2$);

IR (nujol mull): 1681 and 1656 $cm^{-1}$; NMR (DMSO-$d_6$): δ 1.40 (3H, d, J=7 Hz), 2.80 (3H, s); 3.00 (1H, m); 3.20 (1H, m); 4.80–5.10 (4H, m); 6.80–7.70 (15H, m); 8.50 (1H, d, J=9 Hz); 10.80 (1H, br); MS (CI) m/e, 456 (55, $M^++H$), 290 (100), 91 (55). Analysis calculated for C, H, N, $C_{28}H_{29}N_3O_3.0.25H_2O$: C, 73.10; H, 6.46; N, 9.13%. Found: C, 73.34; H, 6.41; N, 9.19%.

EXAMPLE 25

(Scheme V)

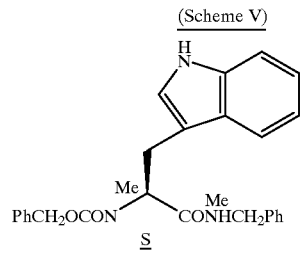

A solution of CBZ-S-abrine pentafluorophenyl ester (100 mg, 0.20 mmol) in EtOAc (20 mL) was treated with N-methyl benzylamine (470 mg, 3.90 mmol) for 10 minutes at room temperature. The mixture was washed with 2N HCl (20 mL, then $H_2O$ (20 mL). The organic phase was dried ($MgSO_4$), filtered, evaporated, and the residue subject to reverse phase chromatography using 60%–70% MeOH in $H_2O$ to give the product as a white foam (66 mg, 75%); mp 44–45° C. (MeOH/$H_2O$);

$[α]_D^{20}$=−49° (c=0.1, MeOH); IR (nujol mull): 1683 and 1633 $cm^{-1}$; NMR (DMSO-$d_6$, 360° K): δ 2.80 (3H, s); 2.90 (3H, s); 3.0–3.4 (2H, m); 4.50 (2H, m); 5.00–5.60 (3H, br, m); 6.90–7.60 (15H, m); 10.60 (1H, br); MS (CI) m/e 456 (42, $M^++H$), 335, 2.90 (100), 91 (62).

EXAMPLE 26

(Scheme V)

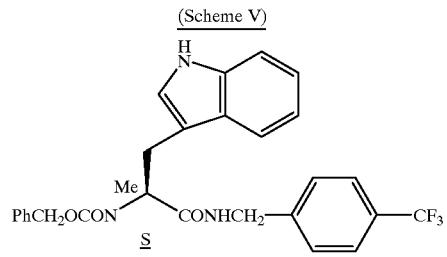

A solution of CBZ-S-abrine pentafluorophenyl ester (100 mg, 0.20 mmol) in EtOAc (20 mL) was treated with 4-trifluoromethylbenzylamine (1.23 g, 7.03 mmol) for 10 minutes at room temperature. The organic phase was washed with diluent HCl (25 mL) then $H_2O$ (25 mL), dried ($MgSO_4$), filtered, and evaporated to dryness in vacuo. The residue was purified by silica gel chromatography using $CH_2Cl_2$ then 20% $Et_2O$ in $CH_2Cl_2$ as eluant to yield the product as a white foam (84 mg, 85%); mp 55–57° C. ($Et_2O/CH_2Cl_2$);

$[α]_D^{20}$=−58° (c=0.1, MeOH); IR (nujol mull): 1689 and 1660 $cm^{-1}$; NMR (DMSO-$d_6$): δ 2.80 (3H, s); 3.10 (1H, m);

3.30 (1H, m); 4.40 (2H, d, J=6 Hz); 4.80–5.10 (3H, br.m); 6.90–7.70 (14H, m); 8.70 (1H, br); 10.90 (1H, br); MS (CI) m/e 510 (50, M$^+$+H), 344 (72), 130 (62), 91 (100). Analysis calculated for C, H, N, C$_{28}$H$_{26}$N$_3$O$_3$F$_3$: C, 66.00; H, 5.14; N, 8.25%. Found: C, 66.17; H, 5.15; N, 8.24%.

EXAMPLE 27

(Scheme V)

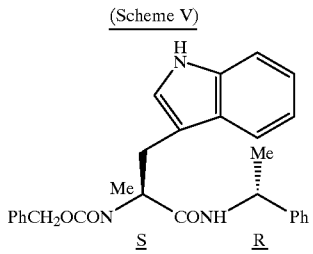

A solution of CBZ-S-abrine pentafluorophenyl ester (100 mg, 0.20 mmol) in EtOAc (10 mL) was treated with R-(+)-α-methylbenzylamine (470 mg, 4.00 mmol) at room temperature for 10 minutes with stirring. The mixture was then washed with 2N HCl (20 mL) then H$_2$O (20 mL). The organic phase was dried over MgSO$_4$, filtered, and evaporated in vacuo to give a residue that was purified by chromatography using 10% Et$_2$O in CH$_2$Cl$_2$ as eluant to give the product as a white foam (62 mg, 71%);

mp 51–56° C. (Et$_2$O/CH$_2$Cl$_2$); [α]$_D^{20}$=−40° (c=0.5, MeOH); IR (nujol mull): 1690 and 1653 cm$^{-1}$; NMR (DMSO-d$_6$): δ 1.30 (3H, d, J=7 Hz); 2.80 (3H, br.s); 3.00–3.30 (2H, m); 4.81–5.10 (4H, br.m); 6.90–7.70 (15H, m); 8.40 (1H, br.d, J=9 Hz); 10.80 (1H, br.s); MS (CI) m/e 456 (33, M$^+$+H); 412 (30), 335 (55), 290 (100), 91 (58). Analysis calculated for C, H, N, C$_{28}$H$_{29}$N$_3$O$_3$.0.25H$_2$O: C, 73.10; H, 6.46; N, 9.13%. Found: C, 73.26; H, 6.32; N, 9.11%.

EXAMPLE 28

(Scheme V)

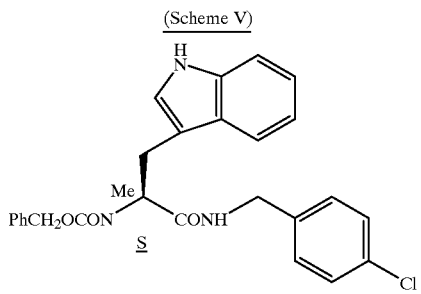

A solution of CBZ-S-abrine pentafluorophenyl ester (100 mg, 0.20 mmol) in EtOAc (30 mL) was treated at room temperature with 4-chlorobenzylamine (600 mg, 4.20 mmol) at room temperature for 10 minutes. The reaction mixture was then washed with 2N HCl (50 mL) then H$_2$O (50 mL). The organic phase was dried over MgSO$_4$, filtered, and evaporated to dryness in vacuo. The residue was purified by chromatography using 10% Et$_2$O:CH$_2$Cl$_2$ as eluant to give the product as a white foam (62 mg, 60%); mp 56–58° C. (Et$_2$O/CH$_2$Cl$_2$);

[α]$_D^{20}$=−65° (c=0.25, MeOH); IR (nujol mull): 1683 and 1659 cm$^{-1}$; NMR (DMSO-d$_6$, 340° C.): δ 2.80 (3H, s); 3.00–3.40 (2H, m); 4.30 (2H, d, J=6 Hz); 5.00 (3H, br); 6.90–7.60 (14H, m); 8.40 (1H, br); 10.60 (1H, br); MS (CI) m/e 476 (55, M$^+$+H), 432 (45), 335 (51), 310 (75), 130 (65), 91 (100). Analysis calculated for C, H, N, C$_{27}$H$_{26}$N$_3$O$_3$Cl: C, 68.13; H, 5.51; N, 8.83%. Found: C, 68.02; H, 5.40; N, 8.76%.

EXAMPLE 29

(Beginning of Scheme VI)

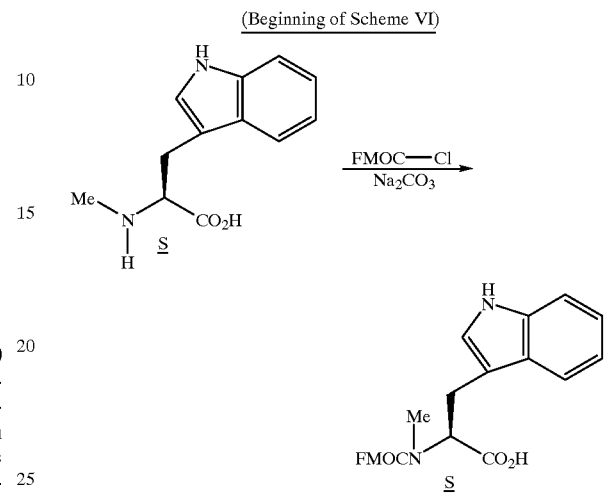

Step 1

To a stirred solution of S-abrine (4.00 g, 18.3 mmol) and sodium carbonate (4.27 g, 40.3 mmol) in aqueous dioxan (1:2, 60 mL), cooled in an ice bath, was added 9-fluorenylmethyl chloroformate (5.69 g, 22 mmol) dropwise in dioxan (40 mL). Mixture was stirred for 4 hours with cooling, then overnight at room temperature. Dioxin was removed in vacuo before diluting with water (100 mL) to obtain a clear solution. Extracted with ether (3×100 mL), ether discarded, aqueous layer acidified using 2N HCl and extracted with ethyl acetate (3×200 mL). Organic layers combined, washed with brine (2×100 mL), dried over MgSO$_4$, filtered, and solvent removed in vacuo to obtain product (8 g, 990%) as a white noncrystalline solid; mp 80–85° C.;

[α]$_D^{20}$=−67.7° (c=1, MeOH); IR (film): 3500–2400, 1715 (CO, carboxylic acid), 1685 (CO, urethane), 1479, 1452, 1404, 1323, 1266, 1198, 1153, 759, and 740 cm$^{-1}$; NMR (DMSO-d$_6$) (340K): δ 2.77 (3H, s, NCH$_3$); 3.05–3.20 (1H, m, one of CH$_2$indole); 3.30 (1H, d.d, J=15.2 and 5.0 Hz, one of CH$_2$indole); 4.00–4.30 (3H, br.m, CHCH$_2$OCONH); 4.89 (1H, d.d, J=10.2 and 5.0 Hz, CH$_2$CHCO$_2$H); 6.90–7.10 (3H, m, aromatics); 7.20–7.55 (8H, m, aromatics); 7.83 (2H, d, J=7.5 Hz, fluorenyl, CH$_3$); 10.65 (1H, s, indole NH); MS m/e (CI$^+$): 441 (2) (M$^+$+H), 245 (2), 219 (14), 207 (9), 188 (5), 179 (100), 130 (17).

Step 2

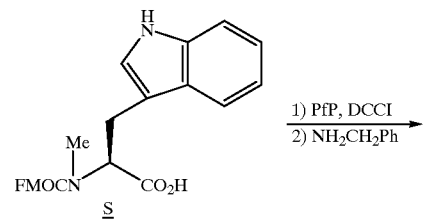

-continued

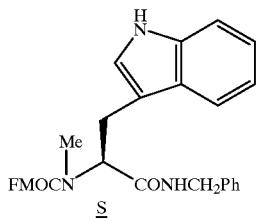

To a stirred solution of Fmoc-S-abrine (4.40 g, 10 mmol) in ethyl acetate (100 mL), cooled in an ice bath, was added pentafluorophenol (1.84 g, 10 mmol) followed by solid N,N'-dicyclohexylcarbodiimide (2.06 g, 10 mmol). After 4 hours at 0° C., dicyclohexylurea was filtered off and the residue washed with cold ethyl acetate (10 mL). A solution of benzylamine (1.07 g, 10 mmol) was added to the filtrate dropwise over 10 minutes (reaction complete after 15 minutes by IR). Reaction mixture was washed with citric acid solution (2×20 mL), sodium hydrogen carbonate solution (2×20 mL), brine (1×20 mL), dried over MgSO$_4$, and solvent removed under vacuum. Residue was chromatographed using 30 then 40% ethyl acetate in hexane to give (4.98 g, 94%) as white noncrystalline solid; mp 74–79° C.;

$[\alpha]_D^{20}$=–47° (c=1, MeOH); IR (film): 3317 (NH), 3061, 2950, 1669 (br., CO, amide and urethane), 1526, 1453, 1402, 1318, 1248, 1152, 1102, 741, and 700 cm$^{-1}$; NMR (DMSO-d$_6$) (340K): δ 2.83 (3H, s, NCH$_3$); 3.06 (1H, d.d, J=15.0 and 9.7 Hz, one of CH$_2$indole); 3.33 (1H, d.d, J=15.0 and 5.8 Hz, one of CH$_2$indole); 4.00–4.40 (3H, brm, CHCH$_2$OCO); 4.30 (2H, d, J=5.9 Hz, NHCH$_2$Ph); 4.97 (1H, d.d, J=9.6 and 5.9 Hz, CHCH$_2$indole); 6.95 (1H, t, J=7.3 Hz, indole CH); 7.00–7.08 (2H, m, indole CH$_2$); 7.15–7.40 (10H, m, aromatics); 7.44 (1H, d, J=7.3 Hz); 7.51 (1H, d, J=7.4 Hz); 7.61 (1H, d, J=7.8 Hz); 7.82 (2H, d, J=7.6 Hz, fluorenyl CH$_2$); 8.20–8.30 (1H, br.m, CONH); 10.65 (1H, s, indole NH); MS m/e (CI$^+$): 530 (1) (M$^+$+H), 309 (8), 308 (35), 276 (6), 207 (24), 180 (36), 179 (100), 178 (90).

Step 3

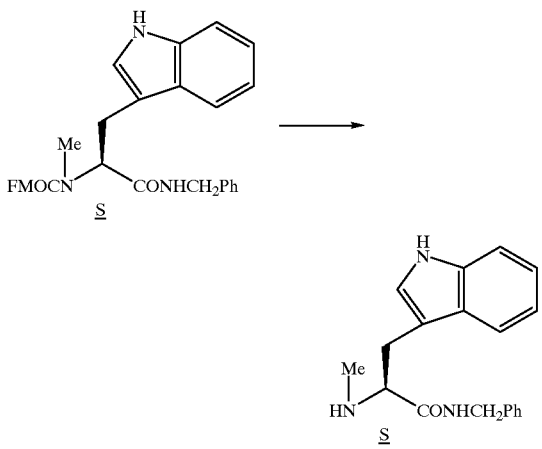

A solution of Fmoc-S-abrine benzylamide (4.0 g, 7.55 mmol) in 20% piperidine in DMF (20 mL) was stirred at room temperature for 5 minutes before removing the solvent under vacuum. Solid residue was stirred vigorously in pet. ether (100 mL), decanted liquid off, and repeated 5 times before leaving to stir overnight in pet. ether (200 mL). Filtered off crystalline product (2.2 g, 95%); mp 140–142° C.;

$[\alpha]_D^{20}$=+29.1° (c=1, MeOH); IR (film): 3306 (NH), 1651 (CO, amide), 1523, 1455, 1340, 1103, 742, and 698 cm$^{-1}$; NMR (DMSO-d$_6$) (340K): δ 1.75 (1H, s, NH); 2.20 (3H, s, NCH$_3$); 2.85 (1H, d, J=14.2 and 7.2 Hz, one of CH$_2$indole); 3.02 (1H, d.d, J=14.2 and 6.3 Hz, one of CH$_2$indole); 3.24 (1H, t, J=6.8 Hz, CHCH$_2$indole); 4.19 (1H, d.d, J=15.1 and 5.6 Hz, one of CH$_2$Ph); 4.30 (1H, d.d, J=15.0 and 5.9 Hz, one of CH$_2$Ph); 6.96 (1H, t, J=7.2 Hz, indole C$_5$ or C$_6$H); 7.00–7.30 (7H, m, CH$_2$Ph and 2 indole CH$_3$); 7.34 (1H, d, J=8.0 Hz, indole C$_7$-H); 7.54 (1H, d, J=7.8 Hz, indole C$_4$-H); 8.25 (1H, t, J=6.0 Hz, CONH); 10.80 (1H, s, indole NH); MS m/e (CI$^+$): 308 (100 (M$^+$+H), 277 (21), 276 (12), 178 (34), 177 (64), 173 (80), 132 (22), 131 (46), 130 (30), 91 (25).

(Scheme VI)

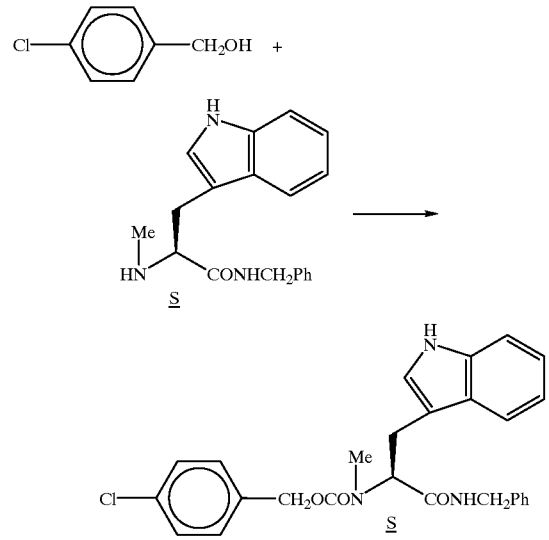

Step 4

To a stirred solution of 4-chlorobenzylalcohol (214 mg, 1.5 mmol) in ethyl acetate (10 mL) at 0° C. was added solid triphosgene (148 mg, 0.5 mmol) followed by the dropwise addition of pyridine (119 mg, 1.5 mmol) in ethyl acetate (5 mL) over 5 minutes. (After 30 minutes IR peak at 1776 cm$^{-1}$.) Filtered off pyridine hydrochloride, removed solvent under vacuum, residue taken up in THF (5 mL) and added dropwise to a solution of S-abrine benzylamide (307 mg, 1 mmol) and pyridine (119 mg, 1.5 mmol) in THF (20 mL). Intense yellow color as chloroformate added, followed by the precipitation of pyridine hydrochloride. After 30 minutes removed solvent under vacuum and residue chromatographed using 4% MeOH/CH$_2$Cl$_2$ to give product (270 mg, 56%) as noncrystalline solid; mp 52–55° C.;

$[\alpha]_D^{20}$=–64.1 (c=1, MeOH); IR (film): 3316 (NH), 1685 (CO, urethane), 1662 (amide), 1530, 1493, 1455, 1399, 1318, 1142, 1092, 1014, and 742 cm$^{-1}$; NMR (DMSO-d$_6$) (340K): δ 2.85 (3H, s, NCH$_3$); 3.07 (1H, d.d, J=15.0 and 9.9 Hz, one of CH$_2$indole); 3.32 (1H, d.d, J=15.0 and 5.8 Hz, one of CH$_2$indole); 4.29 (2H, d, J=5.9 Hz, NHCH$_2$Ph); 4.80–5.05 (3H, br.m, CH$_2$OCONHCH); 6.94 (1H, t, J=7.4 Hz, indole CH); 7.00–7.30 (11H, m, aromatics); 7.34 (1H, d, J=8.5 Hz, indole C$_7$-H); 7.57 (1H, d, J=7.5 Hz, indole C$_4$-H); 8.30–8.40 (1H, br.s, CONH$_2$); 10.65 (1H, s, indole NH); MS m/e (CI$^+$): 476 (32) (M$^+$+H), 434 (17), 432 (44), 369 (23), 297 (17), 276 (100), 177 (24), 171 (24), 130 (57), 125 (51), 91 (24).

EXAMPLE 30

(Scheme VI)

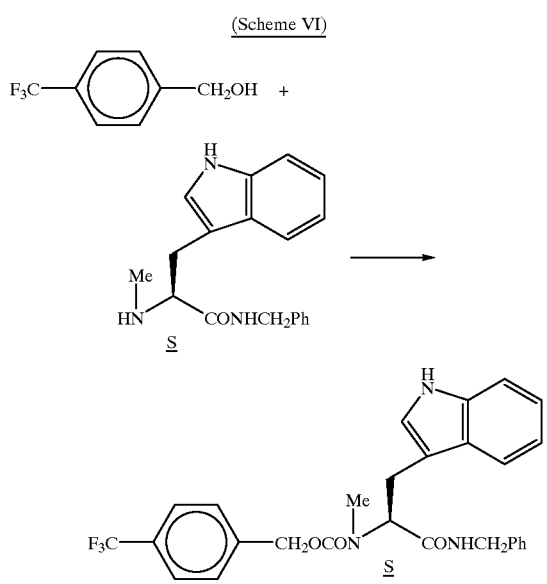

Step 5

Method as for Step 4, Example 29 using 4-trifluoromethylbenzyl alcohol (264 mg, 1.5 mmol) to give product (388 mg, 76%) as noncrystalline solid;

mp 53–57° C.; $[\alpha]_D^{20}=-63.1°$ (c=1, MeOH); IR (film): 3307 (NH), 1663 (br, CO, amide and urethane), 1531, 1326, 1124, 1067, 1018, 824, and 742 cm$^{-1}$; NMR (DMSO-d$_6$) (340K): δ 2.88 (3H, s, NCH$_3$); 3.10 (1H, d.d, J=14.9 and 10.0 Hz, one of CH$_2$indole); 3.33 (1H, d.d, J=14.9 and 5.7 Hz, one of CH$_2$indole); 4.30 (2H, d, J=5.8 Hz, NHCH$_2$Ph); 4.90–5.10 (3H, m, CH$_2$OCO and CHCH$_2$indole); 6.93 (1H, t, J=7.3 Hz, indole CH); 7.00–7.35 (10H, m, aromatics); 7.50–7.65 (3H, m, indole C$_7$-H and

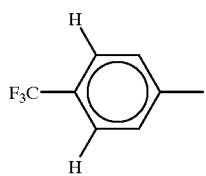

; 8.30–8.40 (1H, br.s, CONH); 10.70 (1H, s, indole NH); MS m/e (CI$^+$): 510 (89) (M$^+$+H), 490 (12), 446 (15), 403 (41), 277 (34), 276 (100), 171 (26), 159 (30), 130 (63), 91 (24).

EXAMPLE 31

(Scheme VI)

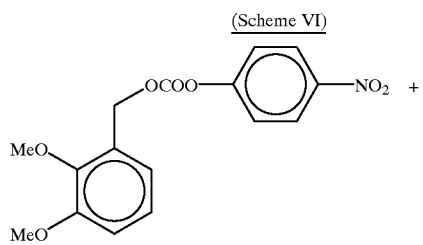

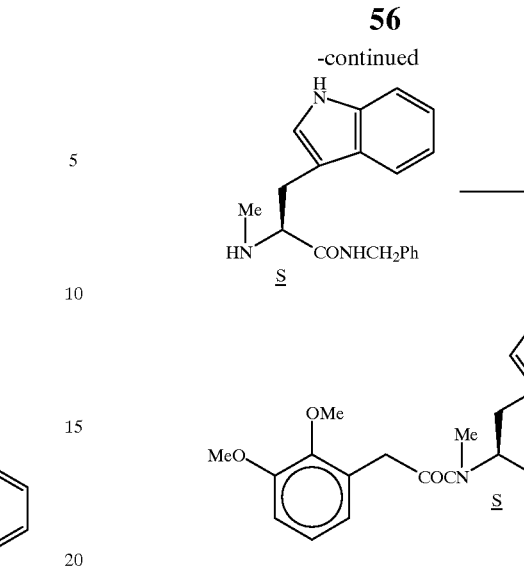

Step 6

A mixture of 2,3-dimethoxybenzyl-4' nitrophenyl carbonate (400 mg, 1.2 mmol) 4-dimethylaminopyridine (122 mg, 1.0 mmol), and S-abrine benzylamide (307 mg, 1.0 mmol) was stirred in DMF (5 mL) for 3 hours before solvent removed under vacuum. Residue taken up in ethyl acetate (50 mL) and washed with citric acid solution (2×50 mL), brine (30 mL), 2N NaOH solution (5×50 mL), brine (30 mL), dried over MgSO$_4$, filtered, and solvent removed under vacuum. Residue chromatographed using 40% MeOH/CH$_2$Cl to give product (500 mg, 100%) as white noncrystalline solid;

mp 49–54° C.; $[\alpha]_D^{20}=-45.3°$ (c=1, MeOH); IR (film): 3631, 3521, 3411, 3321, 2936, 2836, 1665 (br, CO, urethane and amide), 1589, 1527, 1484, 1456, 1400, 1186, 1151, 1085, 1009, 743, and 701 cm$^{-1}$; NMR (DMSO-d$_6$) (340K): δ 2.84 (3H, s, NCH$_3$); 3.07 (1H, d.d, J=14.9 and 9.7 Hz, one of CH$_2$indole); 3.32 (1H, d.d, J=14.9 and 5.9 Hz, one of CH$_2$indole); 3.65 (3H, s, OCH$_3$); 3.79 (3H, s, OMe); 4.29 (2H, d, J=5.9 Hz, NHCH$_2$Ph); 4.90–5.05 (3H, m, CH$_2$OCONCH); 6.65–6.75 (1H, br.s, one of CH$_3$ on OMe ring); 6.90–7.10 (5H, m, aromatics); 7.15–7.30 (5H, m, aromatics); 7.33 (1H, d, J=8.1 Hz, indole C$_7$-H); 7.57 (1H, d, J=7.8 Hz, indole C$_9$-H); 8.25–8.35 (1H, m, CONHCH$_2$); 10.65 (1H, s, indole NH); Ms m/e (CI$^+$): 502 (13) (M$^+$+H), 459 (31), 458 (100), 277 (21), 276 (92), 151 (87), 130 (35).

EXAMPLE 32

(Scheme VII)

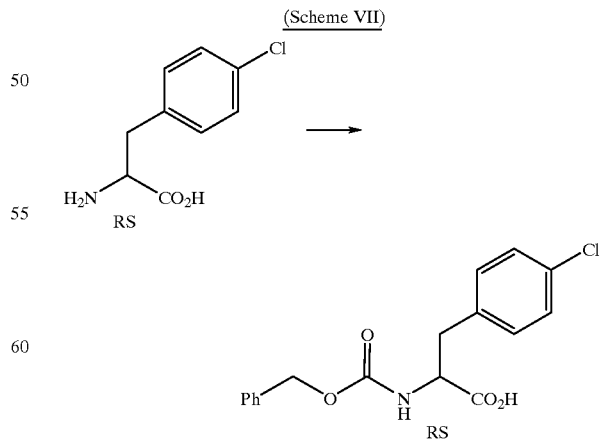

Benzylchloroformate (0.94 g, 5.5 mmol) was added dropwise to a suspension of RS-4-chlorophenylalanine (1.0 g, 5.0 mmol) in 1 M $Na_2CO_3$ (20 mL), cooled to 0° C. The reaction mixture was stirred for 5 hours at room temperature, then acidified to pH 1 with concentrated HCl. The white precipitate formed was collected by filtration and recrystallized from ethyl acetate/hexane to give CBZ-RS-4-chlorophenylalanine (0.95 g, 57%);

mp 152–155° C.; IR (film): 3309, 1692 (urethane CO) and 1592 $cm^{-1}$ (amide II); NMR (DMSO-$d_6$): δ 2.83 (1H, d.d, J=10.9 and 13.7 Hz, one of βCH$_2$); 3.07 (1H, d.d, J=4.3 and 13.7 Hz, one of βCH$_2$); 4.19 (1H, m, αCH); 4.97 (2H, s, C$\underline{H}_2$Ph); 7.31 (9H, m, aromatics); 7.65 (1H, d, J=8.5 Hz, NH); MS m/e (FAB) 334 $[MH]^+$.

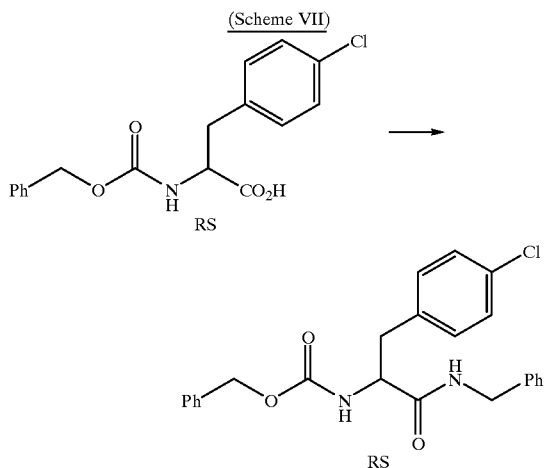

(Scheme VII)

CBZ-RS-4-chlorophenylalanine (0.5 g, 1.5 mmol) was dissolved in ethyl acetate (5 mL) and dicyclohexylcarbodiimide (0.31 g, 1.5 mmol) was added. Pentafluorophenol (0.28 g, 1.5 mmol) was added and the reaction was stirred overnight at room temperature. The white precipitate formed was removed by filtration and the filtrate concentrated in vacuo to give the activated amino acid as a white solid which was redissolved in ethyl acetate (10 mL). Benzylamine (0.16 mL, 1.5 mmol) was added and the reaction was stirred at room temperature for 1 hour. The white precipitate was collected by filtration and purified by chromatography, followed by recrystallization from ethyl acetate to give the product (0.38 g, 60%);

mp 157–158° C.; IR (film): 3232, 1698 (urethane CO), 1657 (amide I), and 1553 $cm^{-1}$ (amide II); NMR (DMSO-$d_6$): δ 2.82 (1H, d.d., J=10.3 and 13.4 Hz, one of βCH$_2$); 3.01 (1H, d.d., J=4.5 and 13.4 Hz, one of βCH$_2$); 4.29 (3H, m, αCH, NHC$\underline{H}_2$Ph); 4.97 (2H, 9, PhC$\underline{H}_2$O); 7.17–7.36 (14H, m, aromatics); 7.58 (1H, d, J=8.6 Hz, NH); 8.53 (1H, t, J=5.8 Hz, $\underline{N}$HCH$_2$Ph); MS m/e (CI) 423 $M^+$.

EXAMPLE 33

(Scheme VII)

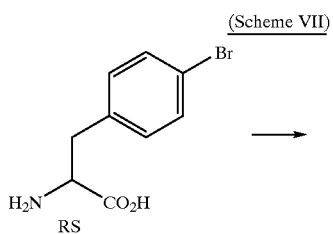

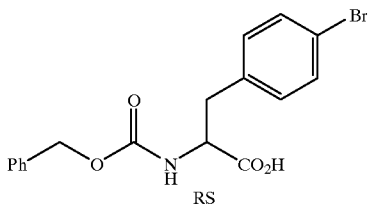

RS-4-Bromophenylalanine (0.98 g, 4 mmol) was suspended in a 1:1 mixture of dioxan/water (20 mL). $NaHCO_3$ (0.67 g, 8 mmol) was added followed by a solution of dibenzyldicarbonate (1.37 g, 4.8 mmol) in dioxan (5 mL). The reaction was stirred at room temperature overnight, then diluted with water (20 mL). After washing with ether (2×20 mL), the aqueous layer was acidified to pH 1 with concentrated HCl and then was extracted with ethyl acetate (3×20 mL). The combined organic extracts were washed with water (3×30 mL), dried over $MgSO_4$, and the solvent was removed in vacuo. The white solid obtained was crystallized from ethyl acetate/hexane to give the product (1.16 g, 77%); mp 161–165° C.;

IR (film): 3310, 1694 (urethane CO), and 1532 $cm^{-1}$ (amide II); NMR (DMSO-$d_6$): 2.81 (1H, d.d, J=10.7 and 13.7 Hz, one of βCH$_2$); 3.06 (1H, d.d, J=4.3 and 13.7 Hz, one of βCH$_2$); 4.19 (1H, m, αCH); 4.97 (2H, s, CH$_2$Ph); 7.31 (9H, m, aromatics); 7.76 (1H, d, J=8.5 Hz, NH); MS m/e (FAB) 378, 380 $M^+$.

Method as for Example 32, Scheme VII. Yield (0.43 g, 61%); mp 163–164° C.;

IR (film): 3296, 1698 (urethane CO), 1656 (amide I), and 1548 $cm^{-1}$ (amide II); NMR (DMSO-$d_6$): δ 2.78 (1H, d.d, J=10.1 and 13.5 Hz, one of βCH$_2$); 2.98 (1H, d.d, J=4.4 and 13.5 Hz, one of βCH$_2$); 4.27 (3H, m, αCH, NHC$\underline{H}_2$Ph); 4.95 (2H, s, PhC$\underline{H}_2$O); 7.16–7.45 (14H, m, aromatics); 7.55 (1H, d, J=8.6 Hz, NH); 8.51 (1H, t, J=5.6 Hz, NHC$\underline{H}_2$Ph); MS m/e (CI) 467, 469 $M^+$.

EXAMPLE 34

(Scheme VII)

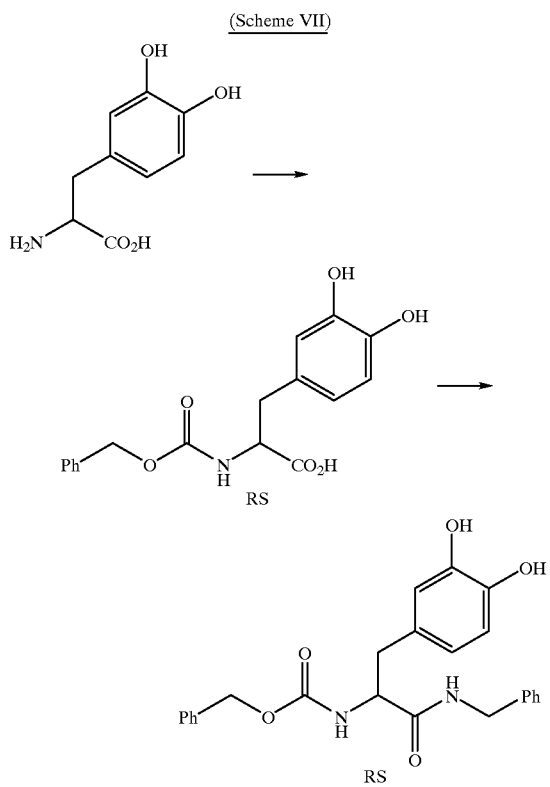

RS-3,4-Dihydroxyphenylalanine (0.99 g, 5 mmol) was suspended in a 1:1 mixture of dioxan water. NaHCO$_3$ (0.84 g, 10 mmol) was added followed by a solution of dibenzyldicarbonate (1.72 g, 6 mmol) in dioxan (5 mL). The reaction was stirred overnight at room temperature under an atmosphere of nitrogen. The solution was diluted with water (20 mL) and was washed with ether (2×20 mL). The aqueous layer was then acidified to pH 1 with concentrated HCl and was extracted with ethyl acetate (3×30 mL). The combined organic extracts were washed with water (3×30 mL) and then were dried over MgSO$_4$. The solvent was removed in vacuo and the brown oil obtained was partially purified by chromatography to give a brown oil (1.49 g, 90%). The oil (1.49 g, 4.5 mmol) was dissolved in ethyl acetate (15 mL), dicyclohexylcarbodiimide (0.93 g, 4.5 mmol), and pentafluorophenol (0.83 g, 4.5 mmol) were added and the reaction was stirred overnight at room temperature. The precipitate formed was removed by filtration. Concentration of the filtrate in vacuo resulted in an orange oil (2.24 g) which was redissolved in ethyl acetate (10 mL). Benzylamine (0.49 mL, 4.5 mmol) was added and the reaction was stirred at room temperature under an atmosphere of nitrogen for 2 hours. Removal of the solvents in vacuo gave a brownish solid which was purified by chromatography to give the product (0.29 g, 16%); mp 207–208° C.;

IR 3500–3000: 1703 (urethane CO), 1662 (amide I), 1609 (aromatic) and 1547 cm$^{-1}$ (amide I); NMR (DMSO-d$_6$): δ 2.62 (1H, d.d, J=9.0 and 13.5 Hz, one of βCH$_2$); 2.81 (1H, d.d, J=4.6 and 13.5 Hz, one of βCH$_2$); 4.18–4.33 (3H, m, αCH, NHCH$_2$Ph); 4.97 (2H, s, PhCH$_2$O); 6.50 (1H, d, J=7.7 Hz, dihydroxy Phe H$_5$); 6.60 (1H, d, J=7.7 Hz, dihydroxyPhe H$_6$); 6.67 (1H, s, dihydroxyPhe H$_2$); 7.14–7.34 (10H, m, aromatics); 7.40 (1H, d, J=8.2 Hz, NH); 8.42 (1H, b.t, NHCH$_2$Ph); 8.66 (2H, s, OH×2); MS m/e (CI) 421 [M$^+$].

EXAMPLE 35

(Scheme I)

Methyl N-[(phenylmethoxy)carbonyl]-, [3,5-bis-(trifluoromethyl)phenyl]-L-tryptophan

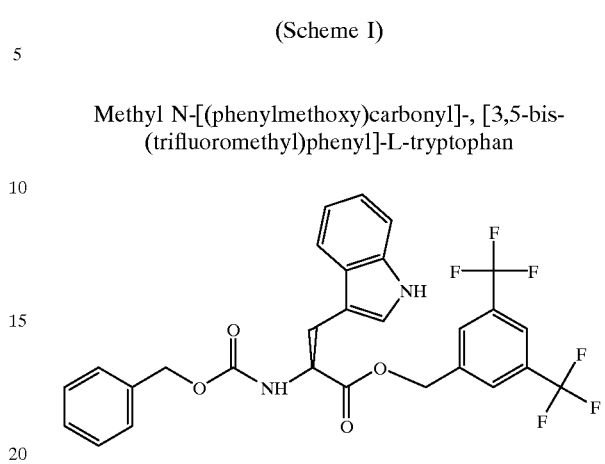

Z-Trp-OPFP (0.2 g, 0.4 mmol) in EtOAc (30 mL) was treated with 3,5-bis(trifluoromethyl)benzyl alcohol (0.12 g, 0.5 mmol) and DMAP (0.03 g). This mixture was warmed to reflux for 20 minutes. The reaction mixture was washed with 2 M HCl (2×50 mL), then H$_2$O (2×50 mL), dried over MgSO$_4$, and evaporated to dryness in vacuo. The residue was purified by silica gel chromatography using 30% EtOAc in CH$_2$Cl$_2$ as eluant, then by reverse phase silica chromatography using 90% MeOH in H$_2$O as eluant to give the product as a white solid (0.192 g, 85%); mp=134–136° C. (MeOH/H$_2$O);

[α]$_D^{20}$=−8° (c=0.25, MeOH); IR (film): 3409, 1745, 1715, 1506 cm$^{-1}$; NMR (DMSO-d$_6$): δ 3.15 (2H, m); 4.38 (1H, m); 4.98 (2H, s); 5.20 (1H, d, J=13.3 Hz); 5.32 (1H, d, J=13.4 Hz); 6.96 (1H, t, J=7.4 Hz); 7.05 (1H, t, J=8.1 Hz); 7.16 (1H, s); 7.30 (6H, m); 7.48 (1H, d, J=8.0 Hz); 7.90 (1H, d, J=7.4 Hz); 7.99 (2H, s), 8.05 (1H, s); 10.82 (1H, br s); MS m/e (CI): 565 (22%), 564 (21%), 521 (31%), 504 (36%), 131 (53%), 130 (100%), 91 (83%); Analysis calculated for C$_{28}$H$_{22}$N$_2$O$_4$F$_6$: C, 59.58; H, 3.93; N, 4.96%. Found: C, 59.87; H, 4.03; N, 4.98%.

EXAMPLES 36 AND 37

Phenylmethyl[1-(1H-indol-3-ylmethyl)-1-methyl-2-[[1-(4-methylphenyl)ethyl]amino]-2-oxoethyl]carbamate Stereoisomer I

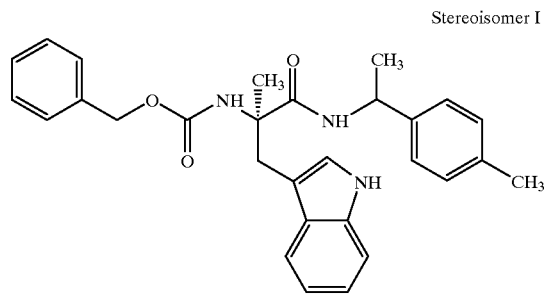

Phenylmethyl[1-(1H-indol-3-ylmethyl)-1-methyl-2-[[1-(4-methylphenyl)ethyl]amino]-2-oxoethyl]carbamate Stereoisomer II

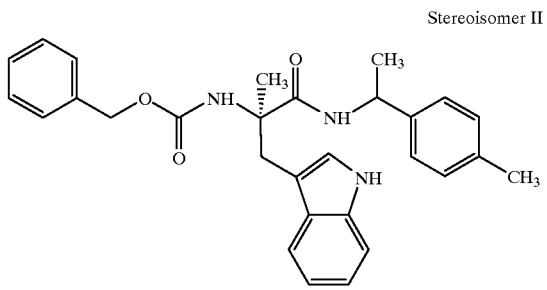

Step 1

4'-Methylacetophenone (93.9 g, 0.70 mol) was treated with EtOH (330 mL), $H_2O$ (400 mL), hydroxylamine hydrochloride (51.1 g, 0.735 mol), potassium hydroxide (94.7 g (85%), 1.44 mmol) and stirred for 12 hours. Solution poured into 1 L of water and treated with excess solid carbondioxide. Filtration and recrystallization from ether/hexane gave pure product (92 g, 88%); mp 82–84° C.;

IR (film): 3327 (broad), 2925, 1607, 1515, 1456, 1369, 1313, 1304, 1180, 1127, 1012, 927, 821, 749 $cm^{-1}$; NMR ($CDCl_3$): δ 2.29 and 2.37 [each 3H, each s, $CH_3$ and Ar—$CH_3$)]; 7.19 (2H, d, J=8.0 Hz, meta to Me); 7.52 (2H, d, J=8.1 Hz, ortho to Me); 9.27 (1H, s, OH); Analysis calculated for $C_9H_{11}NO$: C, 72.46; H, 7.43; N, 9.39%. Found: C, 72.35; H, 7.46; N, 9.38%.

Step 2

Oxime (29.83 g, 0.2 mol) dissolved in absolute EtOH (200 mL) and 10% palladium on carbon (2 g) added. Shaken for 3 hours under an atmosphere of hydrogen at 50 psi before filtering off catalyst using celite. Solvent removed under reduced pressure and residue taken up in 250 mL of ether and amine extracted into 15% hydrochloric acid (50 mL), aqueous phase basified using 50% NaOH solution and product extracted with ether (2×250 mL). Organic phase dried over $K_2CO_3$, ether removed under reduced pressure, and residue distilled to give pure product (24.6 g, 91%); bp 120° C. 10 mm Hg;

NMR ($CDCl_3$): δ 1.37 (3H, d, J=6.6 Hz, $CHCH_3$); 1.47 (2H, s, $NH_2$); 2.33 (3H, s, MeAr); 4.08 (1H, q, J=6.6 Hz, $CHCH_3$); 7.13 (2H, d, J=7.13 Hz); 7.23 (2H, d, J=7.23 Hz); Analysis calculated for $C_9H_{13}N.0.05H_2O$: C, 79.42; H, 9.70; N, 10.29%. Found: C, 79.36; H, 9.76; N, 10.26%.

Step 3

To a stirred solution CBZ-(R)-α-methyltryptophan-pentafluorobenzyl ester (0.259 g, 0.5 mmol) in EtOAc (30 mL) was added amine (0.081 g, 0.6 mmol) and left to stir overnight at room temperature. Reaction mixture washed with 10% citric acid solution (3×30 mL), $H_2O$ (30 mL), saturated $NaHCO_3$ solution (2×30 mL), brine (2×30 mL), dried over $MgSO_4$, and solvent removed under reduced pressure. Residue chromatographed using ether as eluant or normal phase silica. Crystallization from ether (2 mL) over 2 days in freezer gave pure Isomer I (CAM 2676) (0.09 g, 38%). The filtrate was taken, solvent removed under reduced pressure, and a foam obtained from dichloromethane to give CAM 2677 (Mainly Isomer II, de >70% by NMR, 80 mg, 34%).

Isomer I mp 155–158° C.; $[\alpha]_D^{22}$=8.1° (c=0.5, MeOH); IR (film): 3328 (br, NH), 2926, 1713 (CO, urethane), 1651 (CO, amide), 1505, 1456, 1249, 1070, 81 $cm^{-1}$; NMR ($CDCl_3$): δ 1.28 (3H, Cl, $CHCH_3$, J=6.9 Hz); 1.61 (3H, s, $CCH_3$); 2.32 (3H, s, $CH_3Ar$); 3.26 (1H, d, J=14.8 Hz, one of $CH_2$ indole); 3.46 (1H, d, J=14.7 Hz, one of $CH_2$ indole); 4.97 (1H, p, J=7.2 Hz, $NHCHCH_3$); 5.07 (2H, s, $CH_2Ph$); 5.37 (1H, s, OCONH); 6.25–6.35 (1H, br.d, NHCH); 6.80 (1H, s, indole $C_2H$); 7.03–7.35 (12H, m, aromatics); 7.58 (1H, d, J=7.7 Hz, indole $C_4$-H); 7.95 (1H, s, indole NH); MS m/e ($CI^+$): 469 ($M^+$, 0.2%), 362 (1%), 340 (1%), 318 (3%), 244 (3%), 130 (16%), 119 (13%), 108 (20%), 91 (100%); Analysis calculated for $C_{29}H_{31}N_3O_3.0.2H_2O$: C, 73.61; H, 6.69; N, 8.88%. Found: C, 72.68; H, 6.63; N, 8.82%.

Isomer II mp 62–65° C.; $[\alpha]_D^{20}$=+45° (c=0.5, MeOH); IR (film): 3325 (br, $NH_3$), 3057, 2976, 2925 (CH str), 1715 (CO, urethane), 1652 (CO, amide), 1506, 1456, 1341, 1250, 1070, 817, 74 $cm^{-1}$; NMR ($CDCl_3$): δ 1.30 (3H, d, J=6.8 Hz, $CH_3CH$); 1.56 (2.55H, s, $CH_3C$ for major diastereoisomer); 1.60 (0.45H, s, $CH_3C$ for minor diastereoisomer); 2.31 (3H, s, Ar Me); 3.28 and 3.47 (each 1H, each d, J=14.7 Hz, each one of $CH_2$ indole); 4.92–5.06 (2H, m, $CHCH_3$, one of C $H_2O$), 5.11 (1H, d, J=12.1 Hz, one of $CH_2O$); 5.27 (0.85H, s, OCONH); 5.40 (0.15H, s, OCONH); 6.30–6.40 (1H, br.d, CHNH); 6.79 (1H, s, indole $C_2H$); 7.05–7.35 (12H, m, aromatics); 7.57 (1H, d, J=7.9 Hz, indole $C_4H$); 8.06 (1H, s, indole NH); MS m/e ($CI^+$): 470 ($M^+$+H, 9%), 426 (2%), 352 (2%), 340 (11%), 318 (20%), 244 (12%), 130 (94%), 119 (100%), 91 (88%); Analysis calculated for $C_{29}H_{31}N_3O_3.0.2H_2O$: C, 73.61; H, 6.69; N, 8.88%. Found: C, 70.56; H, 6.69; N, 8.88%.

EXAMPLE 38

Phenylmethyl[R-(R*,R*)]-(2-[(1-cyclohexylethyl)-amino]-1-(1H-indol-3-ylmethyl)-1-methyl-2-oxoethyl]carbamate

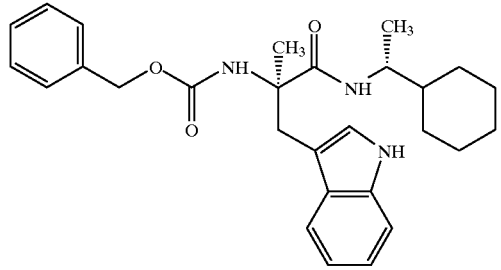

A solution of Z-α-Me-R-Trp-OPFP ester (0.5 g, 0.1 mmol) in EtOAc (30 mL) was treated with cyclohexyl-1-ethyl amine (R isomer) (0.15 g, 1.2 mmol) and stirred for 2 hours at room temperature. The solvent was evaporated and the residue purified by silica gel chromatography using 0–1% MeOH in $CH_2Cl_2$ as eluant then by reverse phase silica gel chromatography using 30% MeOH in $H_2O$ as eluant to give the product as an amorphous white solid (0.277 g, 62%); mp 51–73° C.;

IR (film): 3318, 1709, 1650, 1516, 1655 $cm^{-1}$; NMR ($CDCl_3$): δ 0.73–0.98 (2H, m); 0.89 (3H, d, J=6.7 Hz); 1.00–1.30 (4H, m); 1.47–1.87 (5H, m); 1.56 (3H, s); 3.28 (1H, d, J=14.7 Hz); 3.48 (1H, d, J=14.5 Hz); 3.64–3.82 (1H, m); 5.08 (2H, br.s); 5.46 (1H, s); 6.13 (1H, d, J=8.8 Hz); 6.87 (1H, d, J=2.2 Hz); 7.06 (1H, dt, J=1.0 and 7.0 Hz); 7.14 (1H, dt, J=1.0 and 7.0 Hz); 7.30 (5H, m); 7.55 (1H, d, J=7.8 Hz); 8.61 (1H, s); Analysis calculated for $C_{28}H_{34}N_3O_3.0.25H_2O$: C, 72.31; H, 7.48; N, 9.08%. Found: C, 72.24; H, 7.58; N, 8.81%.

EXAMPLE 39

Phenylmethyl (R,RS)-[2-[[1-[3,5-bis(trifluoromethyl)-phenyl]ethyl]amino]-1-(1H-indol-3-ylmethyl)-1-methyl-2-oxoethyl]carbamate

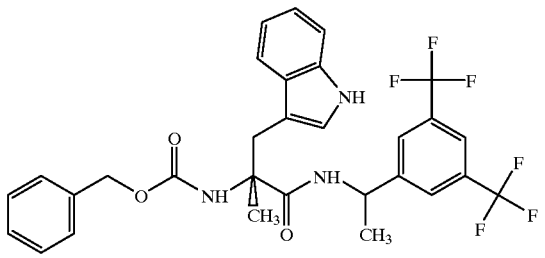

A solution of Z-αMe-R-Trp-OPFP ester (0.25 g, 0.50 mmol) in EtOAc (50 mL) was treated with 3,5-bis-(trifluoromethyl)-α-methyl-benzylamine (RS mixture) (0.245 g, 0.950 mmol). The reacting mixture was stirred at room temperature for 1 hour, washed 2 M HCl (2×50 mL) and H$_2$O (2×50 mL). The organic phase was dried (MgSO$_4$), filtered, and evaporated to dryness in vacuo. The residue was purified by silica gel chromatography using a 10–80% gradient of EtOAc in hexane as eluant, then by r ever se phase silica gel chromatography using 80% MeOH in H$_2$O as eluant to give the product as a white foam (0.232 g, 81%); mp 69–73° C. (CH$_2$Cl$_2$);

[α]$_D^{20}$=+29 (c=0.25, MeOH); IR (film): 3327, 1716, 1661, 1506, 1279 cm$^{-1}$; NMR (DMSO-d$_6$) (340 K): δ 1.25–1.45 (6H, m); 3.20 (1H) and 3.36 (1H) both obscured by H$_2$O; 5.04 (3H, mn); 6.79 (1H, br.s); 6.87–7.10 (3H, m); 7.33 (6H, m); 7.46 (1H, d, J=7.8 Hz); 7.87–8.15 (4H, m); 10.70 (1H, br.s); Analysis calculated for C$_{30}$H$_{27}$N$_3$O$_3$F$_6$: C, 60.91; H, 4.60; N, 7.10%. Found: C, 60.93; H, 4.68; N, 6.96%.

EXAMPLE 40

Phenylmethyl (R,RS)-[1-(1H-indol-3-ylmethyl)-2-[[1-(4-methoxyphenyl)ethyl]amino]-1-methyl-2-oxoethyl]carbamate

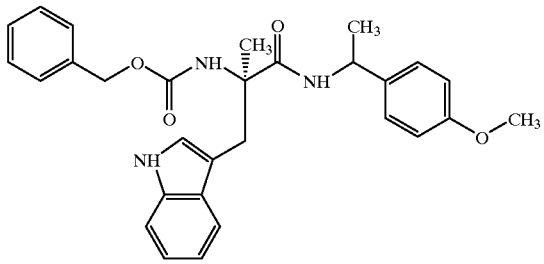

Z-R-α-Me-Trp-OPFP ester (0.2 g, 0.4 mmol) in EtOAc (30 mL) was treated with racemic 4-methoxy-α-methylbenzylamine (0.15 g, 1.00 mmol) as the mixture stirred at room temperature for 20 minutes. Triethylamine (1 g, 9 mmol) was then added and the solution stirred a further 30 minutes. The reaction mixture was washed with 1 M HCl (2×50 mL) then H$_2$O (2×50 mL), dried (MgSO$_4$), filtered, and evaporated to dryness in vacuo. The residue was separated by chromatography over silica gel using CH$_2$Cl$_2$ then 20% Et$_2$O in CH$_2$Cl$_2$ as eluant to give the product as a white foam (0.176 g, 94%);

mp 62–65° C. (MeOH); [α]$_D^{20}$=+19° (c=0.5, MeOH); IR (film): 3338, 2933, 1716, 1652, 1513, 1456, 1247 cm$^{-1}$; NMR (DMSO-d$_6$): δ 1.26 (1.5H, d, J=7.1 Hz); 1.30 (1.5H, d, J=7.1 Hz); 1.33 (1.5H, s); 1.38 (1.5H, s); 3.30 (2H, obscured by H$_2$O); 3.72 (1.5H, s); 3.73 (1.5H, s); 4.85 (1H, m); 5.04 (2H, s); 6.79–6.95 (5H, m); 7.02 (1H, t, J=7.1 Hz); 7.20 (2H, dd, J=8.7 and 12.6 Hz); 7.34 (6H, m); 7.47 (1H, t, J=7.2 Hz); 7.81 (0.5H, d, J=8.0 Hz); 7.93 (0.5H, d, J=8.0 Hz); 10.80 (1H, br.s); MS m/e (FAB): 486 (75%), 356 (100%), 264 (98%); Analysis calculated for C$_{29}$H$_{31}$N$_3$O$_4$.0.25H$_2$O: C, 71.07; H, 6.48; N, 8.57%. Found: C, 71.08; H, 6.58; N, 8.40%.

EXAMPLE 41

4-Pyridinylmethyl[1-(1H-indol-3-ylmethyl)-1-methyl-2-oxo-2-[(1-phenylethyl)amino]carbamate

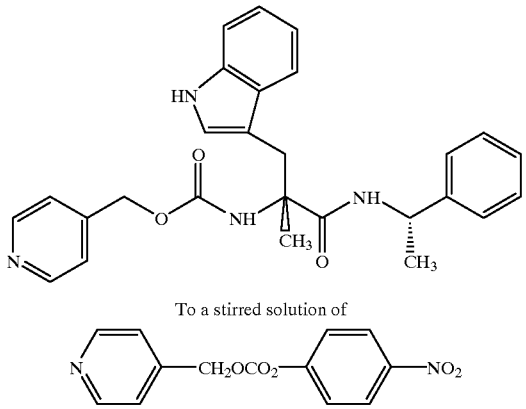

To a stirred solution of (Veber, et al., *J Org Chem* 1977;42:3256) (302 mg, 1.1 mmol) and α-methyltryptophanyl-1-phenethylamide (321 mg, 1 mmol) in DMF (10 mL, anhydrous) was added solid DMAP (122 mg, 1 mmol). After stirring overnight at room temperature, the DMF was removed at 60° C. under reduced pressure and the residue suspended between EtOAc (50 mL) and 1N NaOH solution (50 mL). The organic phase was washed with 5×30 mL portions of 1N NaOH solution, brine (30 mL), dried over MgSO$_4$, filtered, and solvent removed under reduced pressure. Residue chromatographed using normal phase silica with EtOAc/MeOH/NH$_3$ (90:10:1) to obtain desired product which crystallized from ether giving white needles (180 g, 39%); mp 146–148° C.;

[α]$_D^{20}$=+4° (c=0.5, MeOH); IR (film): 3309 (br, NH), 1721 (CDCl urethane), 1650 (CO, amide), 1609, 1494, 1455, 1417, 1342, 1252, 1077, 910, 735, 700, 666 cm$^-$; NMR (CDCl$_3$): δ 1.27 (3H, d, J=6.9 Hz, CH, CH$_3$); 1.67 (3H, s, CCH$_3$); 3.32 (1H, d, J=14.7 Hz, one of CH$_2$ indole); 3.47 (1H, d, J=14.7 Hz, one of CH$_2$ indole); 5.00 (1H, p, J=7.0 Hz, CH$_3$CHNH); 5.07 (2H, s, CH$_2$O); 6.20 (1H, d, J=7.3 Hz CONHCH); 5.67 (1H, s, OCONH); 6.87 (1H, d, J=2.3 Hz, indole C$_2$H); 7.05–7.30 (9H, m, CHPh, 2 indole CH's and 2 pyridyl CH's); 7.36 (1H, d, J=3.0 Hz, indole C$_7$H); 7.59 (1H, d, J=7.9 Hz indole C$_4$H); 8.09 (1H, s, indole NH); 8.54 (2H, d.d, J=4.4 and 1.6 Hz, pyridyl CH's); MS m/e (CI$^+$): 457 (M$^+$+H, 2%), 348 (5%), 244 (4%), 219 (1%), 201 (3%), 138 (10%), 130 (24%), 110 (100%), 92 (52%); Analysis calculated for C$_{27}$H$_{28}$N$_4$O$_3$.0.25H$_2$O: C, 70.34; H, 6.23; N, 12.15%. Found: C, 70.31; H, 6.08; N, 11.99%.

EXAMPLE 42

3-Thienylmethyl[R-(R*,S*)]-[1-(1H-indol-3-ylmethyl)-1-methyl-2-oxo-2-[(1-phenylethyl)amino]ethyl]carbamate

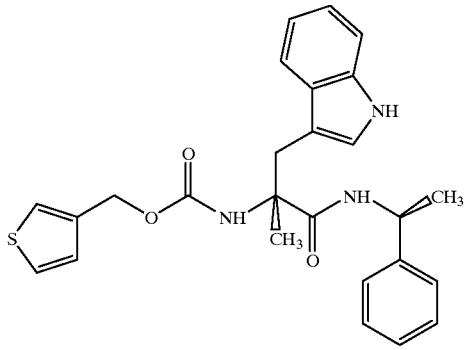

Step 1

To a stirred solution of 3-thiophenmethanol (1.14 g, 10 mmol) and 4-nitrophenylchloroformate (2.01 g, 10 mmol) in dichloromethane (50 mL) at. 0° C. was added dropwise a solution of pyridine (0.79 g, 10 mmol) in dichloromethane (10 mL). Reaction mixture allowed to warm to room temperature overnight. Solvent removed under reduced pressure and residue taken up between EtOAc (50 mL) and 10% citric acid solution (50 mL). Organic phase washed successively with 10% citric acid solution (2×30 mL), $H_2O$ (30 mL), saturated $NaHCO_3$ solution (2×50 mL), and brine (50 mL). Organic phase dried over $MgSO_4$, filtered, and solvent removed under reduced pressure. Two crystallizations from EtOAc gave pure product (1.11 g, 40%); mp 75.0–78.4° C.;

IR (film): 1763 (C=O), 1593 (aromatic C—H), 1522 ($NO_2$), 1491, 1347 ($NO_2$), 1211, 1164, 862 cm$^{-1}$; NMR ($CDCl_3$): δ 5.30 (2H, s, $CH_2$); 7.16–7.18 (1, m, aromatic C-H); 7.35–7.45 (2H, m, aromatic); 7.37 (2H, d, J=9.1 Hz,

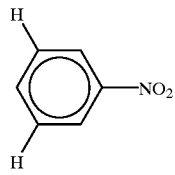

; 8.27 (2H, d, J=9.2 Hz

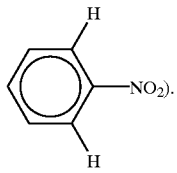

Analysis calculated for $C_{12}H_9NO_5S$: C, 51.61; H, 3.25; N, 5.02; S, 11.48%. Found: C, 51.57; H, 3.21; N, 5.03; S, 11.34%.

Step 2

To a stirred solution of the carbonate (154 mg, 0.55 mmol) and α-methyltryptophanyl-1-phenethylamide (160 mg, 0.5 mmol) in DMF (5 mL, anhydrous) was added solid DMAP (61 mg, 0.5 mmol) and left to stir overnight at room temperature. Solvent removed at 60° C. under reduced pressure and the residue taken up in EtOAc (30 mL) and washed successively with 10% citric acid solution (2×30 mL), $H_2O$ (30 mL), 1N NaOH (5×30 mL, until aqueous phase no longer intense yellow in color), and brine (2×30 mL). Organic phase dried over $MgSO_4$, filtered, solvent removed under reduced pressure, and residue crystallized from ether to give pure product (197 mg, 85%); mp 117–121° C.;

IR (film): 3327 (br, NH), 1711 (CO, urethane), 1651 (CO, amide), 1494, 1454, 1247, 1071, 909, 741 cm$^{-1}$; NMR ($CDCl_3$): δ 1.32 (3H, d, J=6.9 Hz, C$\underline{H}_3$CH); 1.61 (3H, s, $CH_3$C), 3.25 (1H, d, J=14.8 Hz, one of $CH_2$ indole); 3.46 (1H, d, J=15 Hz, one of $CH_2$ indole); 4.95–5.15 (3H, m, C$\underline{H}_2$O and C$\underline{H}$Ph); 5.33 (1H, s, OCON$\underline{H}$); 6.35–6.45 (1H, br.d, CON$\underline{H}$CH); 6.76 (1H, s, indole $C_2\underline{H}$); 7.05–7.35 (11H, m, aromatics); 7.57 (1H, d, J=7.7 Hz, indole $C_4$-H); 8.01 (1H, s, indole NH); MS m/e (CI$^-$): 462 (M$^+$+H, 0.2%), 348 (4%), 304 (2%), 244 (5%), 219 (1%), 158 (1%), 130 (37%), 114 (94%), 97 (100%), 85 (71%); Analysis calculated for $C_{26}H_{27}N_3O_3S$: C, 67.66; H, 5.90; N, 9.10; O, 6.95%. Found: C, 67,51; H, 5.88; N, 9.03; O, 6.94%.

EXAMPLE 43

2-Thienylmethyl[R-(R*,S*)]-[1-(1H-indol-3-ylmethyl)-1-methyl-2-oxo-2-[(1-phenylethyl)amino]ethyl]carbamate

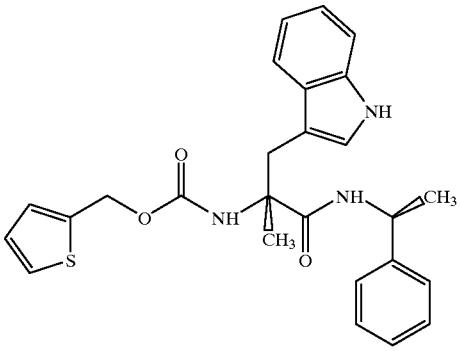

Step 1

See Method as for Example 42. Yield=2.09 g, 75%; mp 67.5–68.5° C.; IR (film): 1766 (CO, carbonate), 1616 and 1594 (aromatic CH); 1523 ($NO_2$); 1493; 1347 ($NO_2$); 1248, 1213, 863 cm$^{-1}$; NMR ($CDCl_3$): δ 5.45 (2H, s, $CH_2O$; 6.98–7.07 (1H, m, aromatic CH); 7.18–7.25 (1H, m, aromatic CH); 7.30–7.43 (1H, m, aromatic CH); 7.38 (2H, d, J=9.2 Hz, CH meta to $NO_2$); 8.28 (2H, d, J=9.2 Hz, CH ortho to $NO_2$); Analysis calculated for $C_{12}H_9NO_5S$: C, 51.61; H, 3.25; N, 5.02%. Found: C, 51.56; H, 3.20; N, 4.94%.

Step 2

See Method as for Example 42. Product chromatographed on normal phase silica using 2% MeOH in $CH_2Cl_2$ followed by crystallization from ether gave pure product (220 mg, 95%); mp 125–127° C.;

$[\alpha]_D^{20}$=+5.7° (c=0.5, MeOH); IR (film): 3327 (br, NH), 1713, 1651, 1494, 1456, 1247, 1068, 740, 699 cm$^{-1}$; NMR ($CDCl_3$): δ 1.32 (3H, d, J=6.9 Hz, C$\underline{H}_3$CH),; 1.62 (3H, s, CC$\underline{H}_3$); 3.24 (1H, d, J=14.7 Hz, one of C$\underline{H}_2$ indole); 3.51 (1H, d, J=14.8 Hz, one of $CH_2$ indole); 5.01 (1H, p, J=7.1 Hz, NHC$\underline{H}$C$H_3$); 5.19 (1H, d J=12.8 Hz, one of C$\underline{H}_2$O); 5.25 (1H, d, J=12.8 Hz, one of $CH_2$O); 5.33 (1H, S, OCON$\underline{H}$); 6.30–6.40 (1H, br.d, CONHCH); 6.77 (1H, s, indole $C_2$H); 6.93–7.30 (10H, m, aromatics); 7.33 (1H, d, J=8.0 Hz, indole $C_7$-H); 7.57 (1H, d, J=7.8 Hz, indole $C_4$-H); 7.95 (1H, s, indole NH); MS m/e (CI⁺): 462 (M⁺+H, 0.2*), 461 (M⁺, 0.2%), 418 (2%), 348 (3%), 304 (3%), 244 (4%), 191 (2%), 130 (30%), 114 (34%), 97 (100%), 85 (47%); Analysis calculated for $C_{26}H_{27}N_3O_3S$: C, 67.66; H, 5.90; N, 9.10; S, 6.95%. Found: C, 67.38; H, 5.82; N, 9.02; S, 7.08%.

EXAMPLE 44

2,3-Dihydro-1H-inden-3-yl [R-(R*,S*)]-[1(1H-indol-3-ylmethyl)-1-methyl-2-oxo-2-[(phenylethyl)amino]ethyl]carbamate

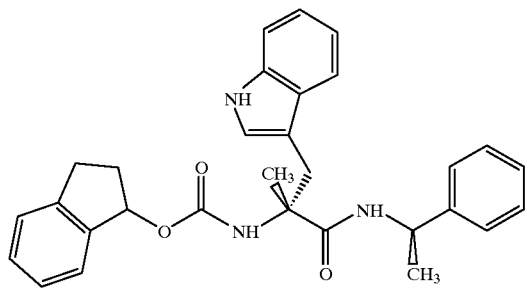

Step 1

See Method for Example 42. Product unstable on standing and unable to obtain a pure crystalline sample. A sample about 90% by NMR was used as soon as possible for Step 2.

Step 2

See Method for Example 42. Crude product chromatographed using normal phase silica using 1.5% MeOH in $CH_2Cl_2$ then rechromatographed using 35% EtOAc in hexane to give pure product (1:1 mix of diastereoisomers, 30 mg, 12%); mp 75–80° C.;

$[\alpha]_D^{20}$=+13.8° (c=0.5, MeOH); IR (film): 3331 (br, NH), 3057, 2976, 2935, 1705 (CO, urethane), 1653 (CO, amide), 1494, 1458, 1376, 1341, 1248, 1070, 742, 700 cm⁻¹; NMR (CDCl₃) mix of 2 diastereoisomers: δ 1.31 (1.5H, C$\underline{H}_3$CH of one diastereoisomer, d, J=6.9 Hz); 1.39 (1.5H, d, J=6.9 Hz, C$\underline{H}_3$CH of one diastereoisomer); 1.61 and 1.62 (each 1.5H, each s, CH₃C for both diastereoisomers); 2.00–2.10 (1H, m, CH of indane); 2.40–2.55 (1H, m, CH of indare); 2.80–2.90 (1H, m, CH of indole); 3.00–3.15 (1H, m, CH of indole); 3.22 (0.5H, d, J=14.7 Hz, one of CH₂ indole for one diastereoisomer); 3.27 (0.5H, d, J=14.6 Hz, one of CH₂ indole for one diastereoisomer); 3.47 (0.5H, d, J=14.1 Hz, one of CH₂ indole for one diastereoisomer); 3.49 (0.5H, d, J=14.0 Hz, one of CH₂ indole for one diastereoisomer); 4.98–5.12 (1H, m, C$\underline{H}$CH₃); 5.20 (1H, s, OCON$\underline{H}$); 6.10–6.15 (1H, m, C$\underline{H}$OCO); 6.40–6.50 (1H, m, CON $\underline{H}$CH); 6.80 and 6.84 (each 0.5H, each s, each half of $C_2$-H, indole); 7.05–7.43 (12H, m, aromatics); 7.59 (1H, d, J=8.0 Hz, indole $C_7$-H); 7.96 and 8.00 (each 0.5H, each s, each half of indole NH); MS m/e (FAB): 5043 (M⁺+Na, 20%), 482.3 (M⁺+H, 12%), 4383 (4%), 366.2 (55%), 322.2 (100%), 304.2 (36%); Analysis calculated for $C_{30}H_{31}N_3O_3$: C, 74.82; H, 6.49; N, 8.73%. Found: C, 74.62; H, 6.46; N, 8.66%.

EXAMPLE 45

1-Naphthalenylmethyl[R-(R*,S*)]-[1-(1H-indol-3-ylmethyl)-1-methyl-2-oxo-2-[(1-phenylethyl)amino]ethyl]carbamate

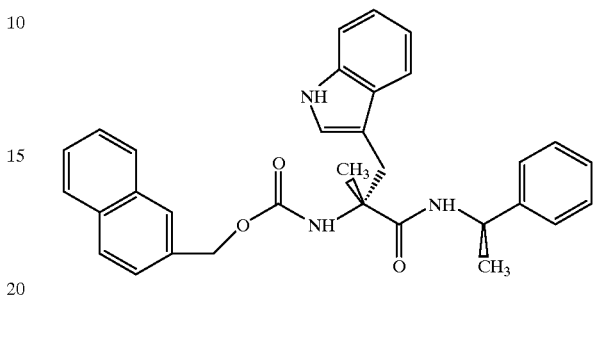

Step 1

See Method for Example 42. Crystallization of product from crude residue using EtOAc followed by washing with 10% citric acid solution (2×30 mL) and multiple water washes gave pure product (2.37 g, 73%);

mp 150.5–152.5° C.; IR (film): 1752 (C=0), 1615, 1595 (aromatic C-H); 1536 (NO₂); 1360 (NO₂); 1281 cm⁻¹; NMR (DMSO-d₆): δ 5.48 (2H, s, Ar CH₂O; 7.50–7.65 (3H, m, aromatics CH); 7.59 (2H, d, J=9.2 Hz, meta to NO₂ group); 7.90–8.05 (4H, m, aromatic CH); 8.32 (2H, d, J=9.1 Hz, ortho to NO₂ group); Analysis calculated for $C_{18}H_{13}NO_5$: C, 66.87; H, 4.05; N, 4.33%. Found: C, 66.74; H, 4.06; N, 4.27%.

Step 2

See Method for Example 45. Crude product chromatographed on normal phase silica using 3% MeOH/$CH_2Cl_2$ then crystallized from ether to give pure product (220 mg, 87%); mp 121–122° C.;

$[\alpha]_D^{20}$=+21.2° (c=0.5, MeOH); IR (film): 3342 (br), 3052, 2924 and 2926 (CH, str); 1717 (CO, urethane); 1653 (CO, amide); 1495, 1457, 1250, 1073, 819, 742 cm⁻¹; NMR (CDCl₃): δ 1.28 (3H, d, J=6.9 Hz, C$\underline{H}_3$CH,); 1.63 (3H, s, C $\underline{H}_3$C); 3.26 (1H, d, J=14.7 Hz, one of CH₂ indole); 3.48 (1H, d, J=14.7 Hz, one of CH₂ indole); 5.00 (1H, p, J=7.0 Hz, NHCHCH₃); 5.24 (1H, d, J=12.5 Hz, one of CH₂O); 5.26 (1H, d, J=12.1 Hz, one of CH₂O); 5.40 (1H, s, OCON$\underline{H}$); 6.30–6.40 (1H, br.d, CON$\underline{H}$CH); 6.74 (1H, s, indole C2-$\underline{H}$); 7.05–7.30 (7H, m, aromatics); 7.31 (1H, d, J=8.0 Hz, indole C7-H)); 7.40–7.52 (3H, m, aromatics); 7.58 (1H, d, J=8.4 Hz, indole C4-H)); 7.75–7.85 (5H, m, aromatics and indole NH); MS m/e (FAB): 506.3 (M⁺+H, 100%), 462.3 (5%), 429.1 (15%), 401.0 (14%), 376.2 (18%) 341.4 (50%), 304.2 (54%), 281.1 (34%), 257.3 (34%); Analysis calculated for $C_{32}H_{31}N_3O_3$: C, 76.02; H, 6.18; N, 8.31%. Found: C, 75.88; H, 6.19; N, 8.28%.

EXAMPLE 46

2,3-Dihydro-1H-inden-2-yl[1-(1H-indol-3-ylmethyl)-1-methyl-2-oxo-2-[(1-phenylethyl)amino]ethyl]carbamate

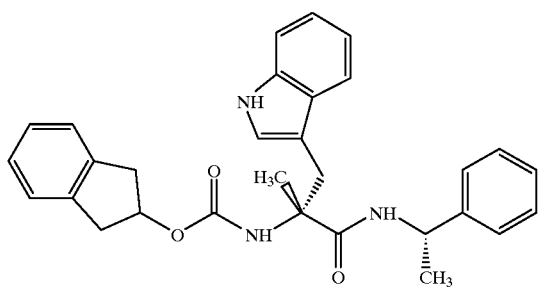

Step 1

See Method for Example 42. Product crystallized from EtOAc and washed with ether to give product (1.8 g, 60%); mp 110.5–113.5° C.;

IR (film): 1765 (CO), 1616, 1594 (aromatic C—H); 1525, 1349 ($NO_2$); 1261; 1226; 1187; 858 $cm^{-1}$; NMR (DMSO-$d_6$): δ 3.21 (2H, d.d, J=17 and 2.8 Hz C$\underline{H}_A H_B$CHC$\underline{H}_A H_B$; 3.41 (2H, d.d, J=17 and 6.1 Hz, CH$_A\underline{H}_B$CHCH$_A\underline{H}_B$); 5.51–5.62 (1H, m, C$\underline{H}$OCOO); 7.18–7.32 (4H, m, aromatic H); 7.37 (2H, d, J=9.2 Hz, H's meta to $NO_2$ group); 8.27 (2H, d, J=9.2 Hz, H's ortho to $NO_2$ group); Analysis calculated for $C_{16}H_{13}NO_5$: C, 64.21; H, 4.38; N, 4.68%. Found: C, 64.36; H, 4.38; N, 4.68%.

Step 2

See Method for Example 42. Used 180 mg (0.6 mmol) of carbonate. Crude product chromatographed using normal phase silica using 2% MeOH/$CH_2Cl_2$ then crystallized from ether to give product (170 mg, 71%);

mp 152–157° C.; $[\alpha]_D^{22}$=+15.3° (c=1, MeOH); IR (film): 3326 (br, NH str), 2924 and 2852 (CH, str), 1705 (CO urethane), 1652 (CO, amide), 1494, 1457, 1252, 1073, 819, 741 $cm^{-1}$; NMR (CDCl$_3$): δ 1.35 (3H, d, J=6.9 Hz, C$\underline{H}_3$CH); 1.58 (3H, s, CC$\underline{H}_3$); 2.90–2.98 (2H, m, indane CH); 3.20–3.32 (3H, m, 2 indane CH and one of C$\underline{H}_2$ indole); 3.46 (1H, d, J=14.5 Hz, one of $CH_2$ indole); 5.02 (1H, p, J=6.9 Hz, NHC$\underline{H}$CH$_3$); 5.20 (1H, s, OCON$\underline{H}$); 5.38–5.48 (1H, m, C$\underline{H}$OCONH); 6.30–6.40 (1H, br.d, CON$\underline{H}$CH); 6.87 (1H, s, indole, $C_2$H); 7.10–7.35 (12H, m, aromatic CH$_3$); 7.59 (1H, d, J=8.1 Hz, indole $C_4$-H); 8.00 (1H, s, indole NH); m/e (CI+): 482 ($M^+$+H, 6%), 348 (14%), 304 (11), 244 (12%), 145 (14%) 134 (78%), 130 (72%), 117 (100%), 105 (88%), 91 (24%); Analysis calculated for $C_{30}H_{31}N_3O_3$: C, 74.82; H, 6.49; N, 8.73%. Found: C, 74.72; H, 6.50; N, 8.76%.

EXAMPLE 47

(2-Fluorophenyl)methyl[R-(R*,S*)]-[1-(1H-indol-3-ylmethyl)-1-methyl-2-oxo-[1-phenylethyl)amino]ethyl]carbamate

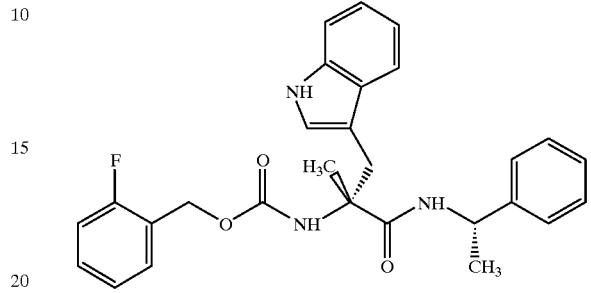

Step 1

See Method for Example 42. Crude residue chromatographed using 10% EtOAc in hexane on normal phase silica then crystallized from ethyl acetate to give pure product (0.990 g, 34%); mp 84–84.5° C.;

IR (film): 1752 (CO, carbonate), 1526 ($NO_2$), 758 $cm^{-1}$; NMR (CDCl$_3$): δ 5.38 (2H, s, PhC$\underline{H}_2$); 7.08–7.23 (2H, m, aromatic CH); 7.32–7.54 (2H, m, aromatic CH); 7.39 (2H, d, J=9.2 Hz, CH meta to $NO_2$); 8.27 (2H, d, J=9.2 Hz, CH's ortho to $NO_2$); Analysis calculated for $C_{14}H_{10}NO_5F$: C, 57.73; H, 3.46; N, 4.81%. Found: C, 57.77; H, 3.52; N, 4.81%.

Step 2

See Method for Example 42 except used 174 mg (0.6 mmol) of carbonate. Crude product chromatographed on normal phase silica using 2% MeOH/$CH_2Cl_2$ then crystallized from ether to give pure product (96 mg, 41%); mp 107–111° C.;

$[\alpha]_D^{22}$=+8° (c=0.25, MeOH); IR (film): 3338 (br, NH), 1713 (CO, urethane); 1652 (CO, amide), 1494, 1456, 1341, 1233, 1111, 1071, 909, 743 $cm^{-1}$; NMR (CDCl$_3$): δ 1.30 (3H, d, J=6.9 Hz, C$\underline{H}_3$CH); 1.62 (2H, s, CH$_3$C); 3.26 (1H, d, J=14.7 Hz, one of $CH_2$ indole); 3.47 (1H, d, J=14.9 Hz, one of $CH_2$ indole); 5.01 (1H, p, J=7.1 Hz, NHC$\underline{H}$CH$_3$); 5.13 (1H, d, J=12.5 Hz, one of C$\underline{H}_2$O); 5.19 (1H, d, J=12.8 Hz, one of C$\underline{H}_2$O); 5.38 (1H, s, OCON$\underline{H}$); 6.35 (1H, d, J=7.6 Hz, N$\underline{H}$CH); 6.81 (1H, d, J=2.2 Hz, indole $C_2$H); 7.00–7.38 (12H, m, aromatics); 7.58 (1H, d, J=7.8 Hz, indole $C_4$-H); 8.00 (1H, s, indole NH); MS m/e ($CI^+$): 474 ($M^+$+H, 5%), 348 (20%), 347 (10%), 304 (9%), 281 (8%), 244 (32%), 219 (8%), 199 (9%), 158 (9%), 131 (23%), 130 (100%), 109 (57%), 105 (27%), 97 (16%); Analysis calculated for $C_{28}H_{28}N_3O_3F$: C, 71.02; H, 5.96; N, 8.87%. Found: C, 71.16; H, 6.01; N, 8.87%.

EXAMPLE 48

3-Furanylmethyl[R-(R*,S*)]-[1-(1H-indol-3-ylmethyl)-1-methyl-2-oxo-2-[(1-phenylethyl)amino]ethyl]carbamate

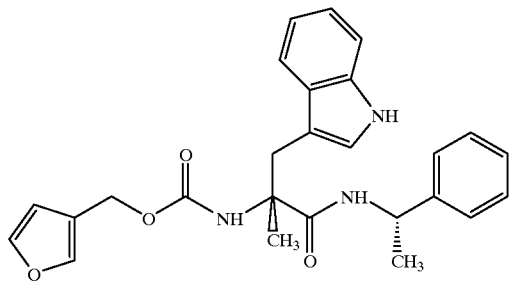

Step 1

See Method for Example 42. Product chromatographed using 14% EtOAc/Hexane then crystallized from EtOAc to give pure product (1.87 mg, 71%); mp 56.5–57.5° C.;

IR (film): 1766 (CO, carbonate), 1617, 1594, 1525, 1348 (NO$_2$), 1214, 1161, 863 cm$^{-1}$; NMR (CDCl$_3$): δ 5.18 (2H, s, PhC$\underline{H}_2$); 6.51 (1H, d, J=1.1 Hz, furan C$_4$-H); 7.37 (2H, d, J=9.2 Hz, CH meta to NO$_2$); 7.45 (1H, s, furan C$_2$ or C$_5$-H); 7.57 (1H, s, furan C$_2$ or C$_5$-H); 8.27 (2H, d, J=9.2 Hz, CH ortho to NO$_2$); Analysis calculated for C$_{12}$H$_9$NO$_6$: C, 54.76; H, 3.45; N, 5.32%. Found: C, 54.68; H, 3.45; N, 5.32%.

Step 2

See Method for Example 42 except used 158 mg (0.6 mmol) of carbonate. Crude product chromatographed using normal phase silica with 1% MeOH n-dichloromethane as eluent then crystallized from ether to give product (164 mg, 74%); mp 126–128° C.;

[α]$_D^{21}$=+4.9° (c=1, MeOH); IR (film): 3332 (br, NH), 1709 (CO, urethane), 1652 (CO, amide), 1495, 1456, 1247, 1066, 1020, 874, 742 cm$^{-1}$; NMR (CDCl$_3$): δ 1.32 (3H, d, J=6.9 Hz, CHC$\underline{H}_3$); 1.61 (3H, s, CC$\underline{H}_3$); 3.25 (1H, d, J=14.7 Hz, one of CH$_2$ indole); 3.45 (1H, d, J=14.8 Hz, one of CH$_2$ indole); 4.93 (2H, s, C$\underline{H}_2$O); 5.02 (1H, p, J=7.2 Hz, NHCHCH$_3$); 5.32 (1H, s, OCON$\underline{H}$); 6.30–6.40 (1H, m, CHN$\underline{H}$); 637 (1H, s, furan C$_4$-H); 6.81 (1H, d, J=2.2 Hz, indole C$_2\underline{H}$); 7.05–7.35 (9H, m, aromatics); 7.43 (1H, s, furan CH); 7.58 (1H, d, J=7.8 Hz, indole C$_4$-H); 8.02 (1H, s, indole NH); MS m/e (CI$^+$): 446 (M$^+$+1, 7%), 445 (2%), 402 (12%), 316 (11%), 304 (26%), 253 (12%), 244 (6%), 199 (8%), 191 (10%), 131 (23%), 130 (100%), 105 (51%), 81 (34%); Analysis calculated for C$_{26}$H$_{27}$N$_3$O$_4$: C, 70.10; H, 6.11; N, 9.43%. Found: C, 70.13; H, 6.13; N, 9.46%.

EXAMPLE 49

2-Furanylmethyl [R,(R*,S*)]-[1-(1H-indol-3-ylmethyl)-1-methyl-2-oxo-2-[(1-phenylethyl)amino]ethyl]carbamate

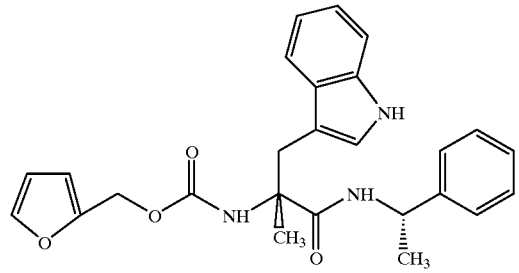

Step 1

See Method for Example 42, however, product was unstable and no pure sample was obtained. Used in the next step after chromatography on normal phase silica using 12.5% EtOAc/Hexane estimated purity >90%; NMR (CDCl$_3$): δ 5.26 (2H, s, CH$_2$O); 6.37–6.45 (1H, m, H$_4$ on ring); 6.54 (1H, d, J=3.2 Hz, H$_3$ on ring); 7.38 (2H, d, J=9.2 Hz, H meta to NO$_2$ Group); 7.43–7.50 (1H, m, H$_5$ on ring); 8.27 (2H, d, J=9.1 Hz, H ortho to NO$_2$ group);

Step 2

See Method for Example 42 except used 158 mg (0.6 mmol) of carbonate. Crude product chromatographed on normal phase silica using 1% MeOH/CH$_2$Cl$_2$ then crystallized from ether to give product (95 mg, 43%);

mp 133–140.5° C.; [α]$_D^{21}$=+9.0° (c=0.5, MeOH); IR (film): 3331 (br, NH), 1713 (CO, urethane), 1652 (CO, amide), 1495, 1248, 1068, 742 cm$^{-1}$; NMR (CDCl$_3$): δ 1.33 (3H, d, J=6.9 Hz, CHC$\underline{H}_3$); 1.61 (3H, s, CC$\underline{H}_3$); 3.24 (1H, d, J=14.7 Hz, one the CH$_2$ indole); 3.46 (1H, d, J=14.8 Hz, one of CH$_2$ indole); 4.95–5.10 (3H, m, C$\underline{H}_2$O and CONHC$\underline{H}$); 5.31 (1H, s, OCON$\underline{H}$); 6.30–6.40 (3H, m, CON$\underline{H}$CH, furan C$_3$ and C$_4$-H); 6.80 (1H, d, J=7.2 Hz, indole C$_2$H); 7.05–7.35 (8H, m, aromatics); 7.38 (1H, s, furan C$_5$-H); 7.57 (1H, d, J=8.1 Hz, indole C$_4$-H); 7.99 (1H, s, indole NH); MS m/e (CI$^+$: 446 (M$^+$+1, 23%), 445 (M$^+$, 11%), 402 (66%), 348 (16%), 316 (16%), 304 (82%), 253 (22%), 244 (24%), 191 (36%), 130 (100%), 105 (88%), 81 (49%); Analysis calculated for C$_{26}$H$_{27}$N$_3$O$_4$: C, 70.10; H, 6.11; N, 9.43%. Found: C, 70.09; H, 6.16; N, 9.37%.

EXAMPLE 50

(3-Fluorophenyl)methyl[R-(R*,S*)]-[1-(1H-indol-3-ylmethyl)-1-methyl-2-oxo-2-[(1-phenylethyl)amino]ethyl]carbamate

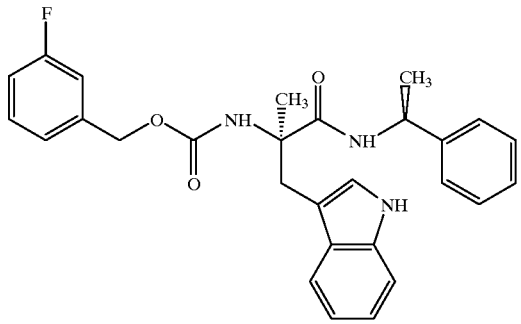

To a stirred solution of 3-fluorobenzyl alcohol (189 mg, 1.5 mmol) and triphosgene (178 mg, 0.6 mmol) under an atmosphere of N$_2$ at 0° C. (ice bath) in CH$_2$Cl$_2$ (10 mL, anhydrous) was added a solution of pyridine (119 mg, 1.5 mmol) in CH$_2$Cl$_2$ (2 mL, anhydrous). IR recorded after 5 and 30 minutes indicated no change with chloroformate at 1776 cm$^{-1}$. Solvent removed under vacuum at 30° C. using a 20% NaOH trap for excess phosgene, added EtOAc (20 mL), and filtered of pyridine hydrochloride. Removed solvent under reduced pressure and added about half of chloroformate to a stirred solution of α-metryptophanyl-1-phenethyl amide (160 mg, 0.5 mmol) and pyridine (40 mg, 0.5 mmol) in THF (20 mL, anhydrous). Precipitate formed immediately and after 5 minutes H$_2$ indicated no starting amine remaining. Removed solvent under reduced pressure and added 50 mL of EtOAc. Organic phase washed successively with 10% citric acid solution (2×30 mL), H$_2$O (30 mL), saturated NaHCO$_3$ (2×30 mL), H$_2$O (2×30 mL), brine (30 mL), then dried over MgSO$_4$. Product recrystallized from ether to give pure product (0.2 g, 84%); mp 109–112.5° C.;

$[\alpha]_D^{21° C.}$=+8.5° (c=1, MeOH); IR (film): 3334 (br, NH str), 1717 (CO, urethane), 1653 (CO, amide); 1592, 1491, 1456, 1256, 1070, 744 cm$^{-1}$; NMR (CDCl$_3$): δ 1.29 (3H, d, J=6.9 Hz, C$\underline{H}_3$CH); 1.63 (3H, s, C$\underline{H}_3$C); 3.27 (1H, d, J=14.8 Hz, one of C$\underline{H}_2$ indole); 3.46 (1H, d, J=14.6 Hz, one of C$\underline{H}_2$ indole); 4.95–5.05 (1H, m, NHC$\underline{H}$CH$_3$); 5.05 (2H, s, C$\underline{H}_2$O); 5.46 (1H, s, OCON$\underline{H}$); 6.29 (1H, d, J=7.3 Hz, CON$\underline{H}$CH); 6.81 (1H, s, indole C$_2$-$\underline{H}$); 6.95–7.30 (11H, m, aromatics); 7.34 (1H, d, J=8.0 Hz, indole C$_7$-$\underline{H}$); 7.58 (1H, d, J=7.9 Hz, indole C$_4$-$\underline{H}$); 8.01 (1H, s, indole NH); Ms m/e (CI$^+$): 475 (M$^+$, 2.27%), 474 (M$^+$+H, 85%); 473 (M$^+$, 13%); 353 (12%); 348 (14%); 348 (14%); 344 (28%); 305 (16%); 304 (67%); 281 (29%); 244 (23%); 199 (14%); 131 (44%); 130 (100%); Analysis calculated for C$_{28}$H$_{28}$N$_3$O$_3$F: C, 71.02; H, 5.96; N, 8.87%. Found: C, 71.01; H, 6.00; N, 8.87%.

EXAMPLE 51

(4-Fluorophenyl)methyl[R-(R*,S*)]-[1-(1H-indol-3-ylmethyl)-1-methyl-2-oxo-2-[(1-phenylethyl)amino]ethyl]carbamate

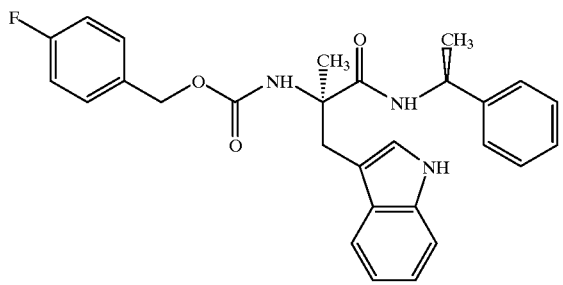

See Method for Example 50. Crystallization from ether gave pure product (191 mg, 81%); mp 101–111° C.;

$[\alpha]_D^{21}$=+7.9 (c=0.5, MeOH); IR (film): 3327 (br, NH str), 1716 (CO, urethane), 1653 (CO, amide), 1511, 1457, 1225, 1071, 825, 743 cm$^{-1}$; NMR (CDCl$_3$): δ 1.29 (3H, d, J=6.9 Hz, C$\underline{H}_3$CH); 1.62 (3H, s, CH$_3$C); 3.26 (1H, d, J=14.8 Hz, one of C$\underline{H}_2$ indole); 3.46 (1H, d, J=14.8 Hz, one of CH$_2$ indole); 4.95–5.05 (1H, m, CONC$\underline{H}$CH$_3$); 5.02 (2H, s, C$\underline{H}_2$O); 5.39 (1H, s, OCON$\underline{H}$); 6.25–6.35 (1H, br.d, CON$\underline{H}$CH); 6.80 (1H, s, indole C$_2$-H); 6.95–7.30 (11H, m, aromatics); 7.34 (1H, d, J=7.8 Hz, indole C$_7$-H); 7.58 (1H, d, J=7.9 Hz, indole C$_4$-H); 7.99 (1H, s, indole NH); MS m/e (CI$^+$): 475 (M$^+$+2, 22%), 474 (M$^+$+H, 68%), 473 (M$^+$, 10%), 430 (35%), 348 (29%), 344 (31%), 305 (22%), 304 (83%), 281 (23%), 244 (36%), 131 (60%), 130 (100%); Analysis calculated for C$_{28}$H$_{28}$N$_3$O$_3$F: C, 71.02; H, 5.96; N, 8.87%. Found: C, 70.80; H, 5.93; N, 8.69%.

EXAMPLE 52

(2,3-Difluorophenyl)methyl[R-(R*,S*)]-[1-(1H-indol-3-methyl)-1-methyl-2-oxo-[(1-phenylethyl)amino]ethyl]-carbamate

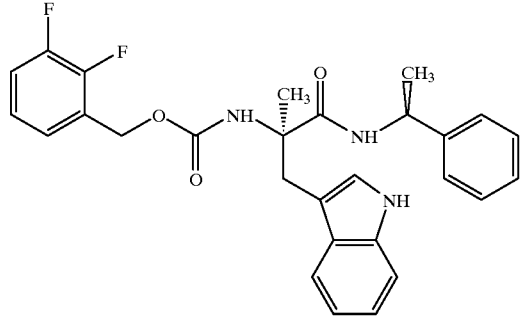

See method for Example 50. Crude product chromatographed using 2% MeOH/CH$_2$Cl$_2$ the crystallized from ether to give pure product (232 mg, 94%);

mp 96–102° C.; $[\alpha]_D^{21}$=+6.7° (c=0.5, MeOH); IR (film): 3336 (br, NH str), 1716 (CO, urethane), 1652 (CO, amide), 1492, 1457, 1288, 1250, 1069, 741 cm$^{-1}$; NMR (CDCl$_3$): δ 1.29 (3H, d, J=6.9 Hz, C$\underline{H}_3$CH); 1.60 (3H, s, CC$\underline{H}_3$); 3.27 (1H, d, J=14.7 Hz, one of C$\underline{H}_2$ indole); 3.46 (1H, d, J=14.6 Hz, one of CH$_2$ indole); 4.95–5.05 (1H, m, NHC$\underline{H}$CH$_3$); 5.13 (1H, d, J=13.0 Hz, one of CH$_2$O); 5.18 (1H, d, J=13.4 Hz, one of CH$_2$O); 5.49 (1H, s, OCONH); 6.29 (1H, d, J=7.2 Hz, N$\underline{H}$CH); 6.84 (1H, s, indole C$_2$H); 6.95–7.35 (11H, m, aromatics); 7.58 (1H, d, J=7.7 Hz, indole C$_4$-H); 8.10 (1H, s, indole NH); MS m/e (CI$^+$): 493 (M$^+$+2, 10%), 492 (M$^+$+1, 4%), 491 (M$^+$, 5%), 371 (11%), 348 (19%), 305 (17%), 304 (54%), 299 (18%), 244 (22%), 199 (12%), 144 (40%), 1310 (98%), 127 (100%), 105 (78%); Analysis calculated for C$_{28}$H$_{27}$N$_3$O$_3$F$_2$: C, 68.42; H, 5.54; N, 8.55%. Found: C, 68,43; H, 5.64; N, 8.51%.

EXAMPLE 53

(2,4-Difluorophenyl)methyl[R-(R*,S*)]-[1-(1H-indol-3-ylmethyl)-1-methyl-2-oxo-2-[(1-phenylethyl)amino]-ethyl]carbamate

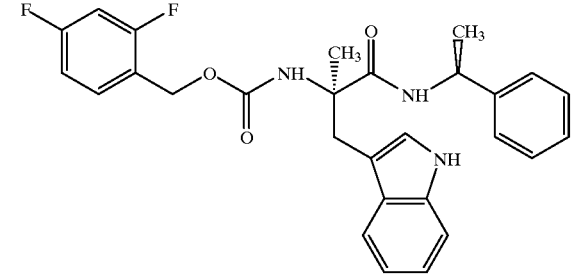

See Method for Example 50. Crude product chromatographed using 2% MeOH/CH$_2$Cl$_2$ then crystallized from ether to give pure product (240 mg, 98%);

mp 77–87° C.; $[\alpha]_D^{21}$=+5.6 (c=1, MeOH); IR (film): 3332 (br, NH str), 1713 (CO, urethane), 1651 (CO, amide), 1507, 1250, 1140, 1101, 1071, 742 cm$^{-1}$; NMR (CDCl$_3$): δ 1.29 (3H, d, J=6.9 Hz, CH$_3$CH); 1.03 (3H, s, CCH$_3$); 3.27 (1H, d, J=14.7 Hz, one of CH$_2$ indole); 3.46 (1H, d, J=14.9 Hz, one of CH$_2$ indole); 4.95–5.05 (1H, m, CHCH$_3$); 5.09 (2H, s, CH$_2$O); 5.43 (1H, s, OCONH); 6.23–6.33 (1H, br.d, CONHCH); 6.75–6.90 (3H, m, aromatics); 7.05–7.35 (9H, m, aromatics); 7.58 (1H, d, J=7.8 Hz, indole C$_4$-H); 8.01 (1H, s, indole NH); MS m/e (CI$^+$): 493 (M$^+$+2, 11%), 492 (M$^+$+1, 40%), 491 (M$^+$, 7%), 448 (12%), 361 (26%), 348 (15%), 304 (56%), 299 (15%), 244 (33%), 199 (14%), 144 (36%), 131 (45%), 130 (100%), 127 (93%), 105 (70%);

Analysis calculated for C$_{28}$H$_{27}$N$_3$O$_3$F$_2$: C, 68.42; H, 5.54; N, 8.55%. Found: C, 68.66; H, 5.63; N, 8.45%.

EXAMPLE 54

(2,5-Difluorophenyl)methyl[R-(R*,S*)]-[1-(1H-indol-3-ylmethyl)-1-methyl-2-oxo-2-[(1-phenylethyl)amino]-ethyl]carbamate

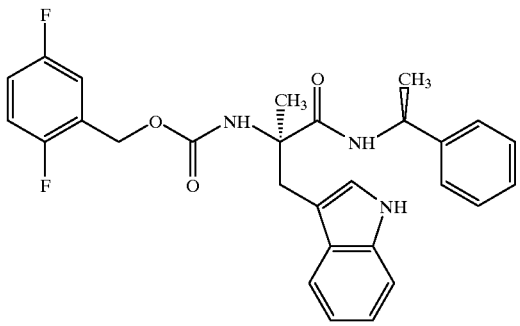

See Method for Example 50. Crystallization from ether gave pure product (229 mg, 95%); mp 121–122° C.;

[α]$_D^{21}$=+6.0 (c=0.5, MeOH); IR (film): 3336 (br, NH str), 1721 (CO, urethane), 1656 (CO, amide), 1496, 1457, 1246, 1191, 1144, 1072, 909, 741 cm$^{-1}$; NMR (CDCl$_3$): δ 1.29 (3H, d, J=6.9 Hz, CH$_3$CH); 1.64 (3H, s, CCH$_3$); 3.28 (1H, d, J=14.7 Hz, one of CH$_2$ indole); 3.47 (1H, d, J=14.0 Hz, one of CH$_2$ indole); 4.95–5.05 (1H, m, NHCHCH$_3$); 5.08 and 5.14 (each 1H, each d, each one of CH$_2$O, J=13.4 Hz); 5.51 (1H, s, OCONH); 6.28 (1H, d, J=7.6 Hz, CONHCH); 6.85 (1H, d, J=2.1 Hz, indole C$_2$H); 6.90–7.33 (10H, m, aromatics); 7.34 (1H, d, J=8.0 Hz, indole C$_7$-H); 7.58 (1H, d, J=7.8 Hz, indole C$_4$-H); 8.05 (1H, s, indole NH); MS m/e (CI$^+$): 493 (M$^+$+2, 14%), 492 (M$^+$+1, 55%), 491 (M$^+$, 6%), 362 (12%), 348 (31%), 347 (17%), 304 (39%), 244 (40%), 131 (50%), 130 (100%), 127 (65%), 105 (66%); Analysis calculated for C$_{28}$H$_{27}$N$_3$O$_3$F$_2$: C, 68.42; H, 5.54; N, 8.55%. Found: C, 68.17; H, 5.46; N, 8.35%.

EXAMPLE 55

Phenylmethyl[R-(R*,S*)] and [S-(R*,R*)]-[1-(1H-indazol-3-ylmethyl-)-2-oxo-2-[(1-phenylethyl)-amino]ethyl]carbamate

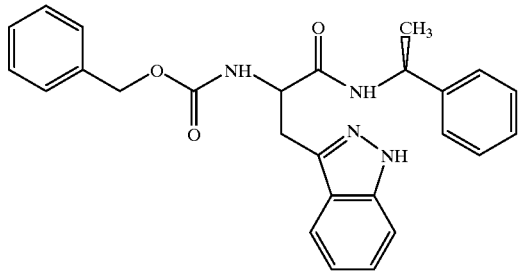

Step 1: N-Benzyloxycarbonyltryptazan

A mixture of tryptazan (PD 018111) (0.09 g, 0.44 mmol), sodium hydrogen carbonate (0.13 g, 1.55 mmol), dibenzyl-dicarbonate (0.18 g, 0.63 mmol), water (5 mL), and dioxan (5 mL) was stirred at room temperature overnight. The mixture was diluted with water, washed twice with ether, acidified with 1N hydrochloric acid, and extracted with ethyl acetate. The combined extracts were washed with water, dried over MgSO$_4$, filtered, and evaporated to dryness. Recrystallization from ethyl acetate/hexane gave colorless crystals (0.12 g).

Step 2: Phenylmethyl[R-(R*,S*)] and [S-(R*,R*)]-[1-(1H-indazol-3-ylmethyl-)-2-oxo-2-[(1-phenylethyl)amino]ethyl] carbamate To a solution of N-benzyloxycarbonyl tryptazan (0.12 g, 0.35 mmol) in ethyl acetate (20 mL) was added hydroxy-benzotriazole hydrate (0.058 g, 0.38 mmol) followed by dicyclohexylcarbodiimide (0.075 g, 0.36 mmol). After stirring at room temperature for 3 hours, the mixture was filtered and (S)-α-methylbenzylamine (0.055 g, 0.45 mmol) in ethyl acetate (5 mL) was added to the filtrate. After stirring at room temperature overnight, the reaction mixture was washed with saturated sodium bicarbonate solution, 1N hydrochloric acid, and water. The solution was then dried over magnesium sulphate, filtered, and evaporated to dryness. The residue was purified by reverse phase chromatography eluting with methanol/water mixtures to give the title compound (0.070 g, 45%); mp 116–120° C.;

NMR (300 MHz, CDCl$_3$): δ 1.23 (3H, d, J=6.9 Hz); 3.32 (1H, dd, J=15.0, 7.3 Hz); 3.59 (1H, ddd, J=15.0, 9.7, and 4.8 Hz); 4.70–4.80 (1H, m); 4.85–4.95 (1H, m); 5.11 (2H, s); 6.14 (0.5H d, J=7.4 Hz); 6.20 (0.5H, d, J=7.1 Hz); 6.60–6.85 (1H, m); 6.90–7.40 (14H, m); 7.70–7.80 (1H, m); Analysis calculated for C$_{26}$H$_{26}$N$_4$O$_3$: C, 70.57; H, 5.92; N, 12.66%. Found: C, 70.41; H, 5.97; N, 12.60%.

EXAMPLE 56

Phenylmethyl[R-(R*,S*)] and [S-(R*,R*)]-[1-[(5-fluoro-1H-indol-3-yl)methyl]-2-oxo-2-[(1-phenylethyl)amino]-ethyl]carbamate

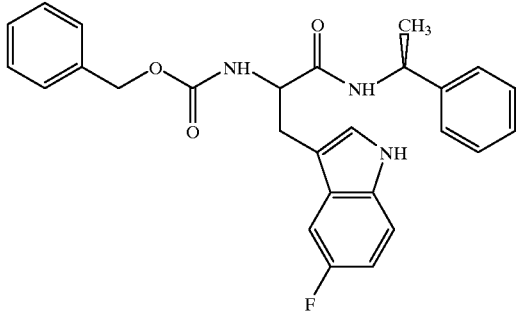

Step 1: N-Benzyloxycarbonyl-5-fluoro-RS-tryptophan

Dibenzyldicarbonate (0.39 g, 3.1 mmol) was dissolved in dioxan (15 mL) and added to a stirred suspension of 5-fluoro tryptophan (0.58 g, 2.6 mmol) and sodium bicarbonate (0.67 g, 8.0 mmol) in water (15 mL). After stirring at room temperature overnight, the reaction mixture was diluted with water and washed with ether twice, acidified with 1N hydrochloric acid, and extracted three times with ethyl acetate. The combined extracts were washed with water, dried MgSO₄, sulphate, filtered, and evaporated. Recrystallization from ethyl acetate and hexane gave colorless crystals (0.75 g, 81%); mp 126–128° C.;

NMR (300 MHz, DMSO-d$_6$): δ 2.96 (1H, dd, J=14.4 and 9.6 Hz); 3.14 (1H, dd, J=14.5 and 4.4 Hz); 4.15–4.25 (1H, m); 4.97 (2H, s); 6.90 (1H, dt, J=9.2 and 2.5 Hz); 7.10–7.35 (8H, m); 7.55 (1H, d, J=8.1 Hz); 10.94 (1H, s); 12.6 (1H, bs); Analysis calculated for $C_{19}H_{17}FN_2O_4$: C, 64.04; H, 4.81; N, 7.86. Found: C, 64.02; H, 4.80; N, 7.84.

Step 2: Phenylmethyl[R-(R*,S*)] and [S-(R*,R*)]-[1-[(5-fluoro-1H-indol-3-yl)methyl]-2-oxo-2-[(1-phenylethyl)amino]ethyl]carbamate To a solution of N-benzyloxycarbonyl-5-fluoro-tryptophan (0.15 g, 0.42 mmol) in ethyl acetate (25 mL) was added 1-hydroxybenzotriazole hydrate (0.06.6 g, 0.43 mmol) followed by dicyclohexylcarbodiimide (0.089 g, 0.43 mmol). After stirring at room temperature for 2 hours, the mixture was filtered and to the filtrate was added a solution of (S)-α-methylbenzylamine (0.065 g, 0.54 mmol) in ethyl acetate (5 mL). After stirring at room temperature for 48 hours, the solution was washed with saturated sodium bicarbonate solution, 1N hydrochloric acid solution, and water. After drying over magnesium sulphate, the solution was filtered, dried, and evaporated. The residue was purified by reverse phase chromatography to give the title compound (0.15 g, 78%); mp 152–155° C.;

NMR (300 MHz, CDCl$_3$): δ 1.18 (1.5H, d, J=6.9 Hz); 1.32 (1.5H, d, J=6.9 Hz); 3.00–3.15 (1H, m); 3.20–3.35 (1H, m); 4.35–4.50 (1H, m); 4.90–5.05 (1H, m); 5.10 (2H, s); 5.35–5.50 (1H, m); 5.70–5.80 (1H, m); 6.78 (0.5H, d); 6.90–7.05 (3.5H, m); 7.20–7.35 (10H, m); 7.80 (0.5H, S); 8.02 (0.5H, s); Analysis calculated for $C_{27}H_{26}FN_3O_3$: C, 70.57; H, 5.70; N, 9.14%. Found: C, 70.67; H, 5.67; N, 9.09%.

EXAMPLE 57

Phenylmethyl[1-(1-methyl-1H-indol-3-ylmethyl]-2-oxo-2-[(1-phenylethyl)amino]ethyl]carbamate

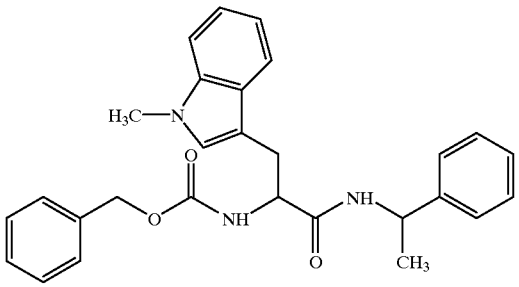

Step 1: CBZ-1-methyl-DL-tryptophan

1-Methyl-DL-tryptophan was suspended in H$_2$O/dioxan (20 mL) and NaHCO$_3$ (0.072 g, 8 mmol) added. A solution of dibenzyldicarbonate (1.37 g, 4.8 mmol) was added and the reaction was stirred at room temperature overnight. The solution was diluted with water then washed with ether. The aqueous was then acidified to pH 1 with concentrated HCl and extracted with ethylacetate. The combined organic extracts were washed with water, dried over MgSO$_4$, and the solvent removed in vacuo. The brown oil obtained was purified by reverse phase chromatography (0.800 g, 65%); mp 58–60° C.;

$[α]_D^{20}$=0 (c=0.25, MeOH); IR (film): 1716 (urethane CO), 1507 cm$^{-1}$ (amide II); NMR (DMSO-d$_6$): δ 2.99 (1H, dxd, J=14.7, 9.5 Hz, one of βCH$_2$); 3.16 (1H, dxd, J=14.7 and 4.5 Hz, one of βCH$_2$); 3.71 (3H, s, NCH$_3$); 4.32 (1H, m, αCH); 4.97 (2H, s, CH$_2$Ph); 7.01–7.65 (11H, m, aromatic protons, urethane NH); 12.65 (1H, s, br, CO$_2$H); MS m/e (CI): 353 MH⁺; Analysis calculated for $C_{20}H_{20}N_2O_4$: C, 68.17; H, 5.72; N, 7.95%. Found: C, 67.80; H, 5.86; N, 8.19%.

Step 2: CBZ-1-Methyl-DL-tryptophan-(+)-α-methylbenzylamine

CBZ-1-methyl-DL-tryptophan (0.39 g, 1.2 mmol), HBTU (0.91 g, 1.2 mmol), and diisopropylethylamine (0.42 mL, 2.4 mmol) were dissolved in DCM (3 mL) and the solution stirred for 10 minutes at room temperature. The (±)-α-methylbenzylamine (0.15 mL, 1.2 mmol) was added and the reaction was stirred for a further 4 hours. The solvent was removed in vacuo and the resulting residue redissolved in ethylacetate. The organic was washed with 5% HCl, 5% NaHCO$_3$, water, and brine. The organic layer was then dried over MgSO$_4$ and the solvent removed in vacuo. The crude material was purified by medium pressure chromatography, ethylacetate/hexane (0.076 g, 14%); mp 69.5–71.8° C.;

$[α]_D^{20}$=0 (c=0.5, MeOH); IR (film): 1712 (urethane CO), 1687 (urethane CO), 1652 (amide I), 1548 cm$^{-1}$ (amide II); NMR (DMSO-d$_6$): δ 1.23, 1.34 (3H, 2×d, J=6.9 and 7.5 Hz, CH$_3$); 2.84–3.19 (2H, m, βCH$_2$); 3.66; 3.71 (3H, 2×s, N—CH$_3$); 4.32–4.37 (1H, m, CH); 4.86–4.97 (3H, m, PhCH$_2$, CH); 6.87–7.66 (16H, m, Ph×2, indole aromatics, urethane NH); 8.32–8.41 (1H, 2×d, J=7.7 and 7.9 Hz, amide NH); MS m/e (CI): 456.3 MH⁺; Analysis calculated for $C_{28}H_{29}N_3O_3$: C, 73.82; H, 6.42; N, 9.22%. Found: C, 73.89; H, 6.57; N, 8.95%.

EXAMPLE 58

Phenylmethyl[R-(R*,S*)]-[1-(2-naphthalenylmethyl-2-oxo-2-[(1-phenylmethyl)amino]ethyl]carbamate

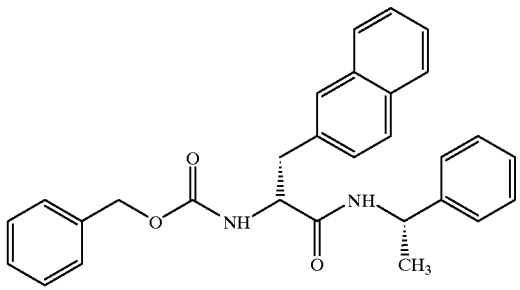

Step 1: CBZ-D-3-(1-naphthyl)alanine

See Method for CBZ-1-methyl-DL-tryptophan in Example 57 (0.17 g, 22%);

IR (film): 1709 (urethane CO), 1532 cm$^{-1}$ (amide II); NMR (DMSO-d$_6$): δ 2.97–3.23 (2H, m, βCH$_2$); 4.32 (1H, m, αCH); 4.94 (2H, s, PhCH$_2$); 7.21–7.89 (13H, m, aromatics, urethane NH).

Step 2: CBZ-D-3-(2-naphthyl)alanine-3-(–)-α-methyl-benzylamine

See Method as for the 1-methyl-DL-tryptophan derivative (0.081 g, 14%); mp 100.2–102.7° C.;

[α]$_D^{20}$=–26° (c=0.25, MeOH); IR (film): 1709 (urethane CO), 1656 (amide I), 1537 cm$^{-1}$ (amide II); NMR (DMSO-d$_6$): δ 1.24 (3H, d, J=7.0 Hz, CH$_3$); 2.97 (1H, dxd, J=13.4 and 9.9 Hz, one of βCH$_2$); 3.13 (1H, dxd, J=13.4 and 5.0 Hz, one of βCH$_2$); 4.42 (1H, m, αH, methylbenzylamine); 4.89 (3H, m, PhCH$_2$, αCH); 7.23–7.48 (14H, m, naphthyl H$_{3,6,7}$, Phx2, urethane NH); 7.84 (4H, m, naphthyl H$_{1,4,5,8}$); 8.38 (1H, d, J=8.0 Hz, amide NH); MS m/e (CI): 453 MH$^+$; Analysis calculated for C$_{29}$H$_{28}$N$_2$O$_3$: C, 76.34; H, 6.41; N, 6.36%. Found: C, 76.74; H, 6.22; N, 6.06%.

EXAMPLE 59

1-Phenylethyl N-[(phenylmethoxy)carbonyl]-DL-tryptophan

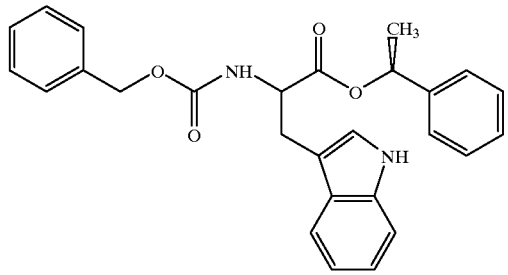

To a solution of N-benzyloxycarbonyl-RS-tryptophan (1.07 g, 3.16 mmol), (S)-sec-phenethyl alcohol (0.39 g, 3.19 mmol) and dimethylaminopyridine (0.04 g, 0.33 mmol) in ethyl acetate (60 mL) was added dicyclohexylcarbodiimide (0.65 g, 3.16 mmol). After stirring at room temperature overnight, the mixture was filtered and evaporated to dryness. Purification by column chromatography eluting with 2% ethyl acetate in dichloromethane gave a colorless gum (1.1 g, 79%);

NMR (300 MHz, CDCl$_3$): δ 1.41 and 1.49 (3H, two d, J=6.5 Hz); 3.10–3.30 (2H, m); 4.70–4.80 (1H, m); 5.00–5.15 (2H, m); 5.20–5.35 (1H, m); 5.80–5.95 (1H, two m); 6.49 and 6.89 (1H, two s); 7.00–7.35 (13H, m); 7.42 (0.5H, d, J=8.0 Hz); 7.55–7.60 (0.5H, m); 7.81–7.94 (1H, two s); Analysis calculated for C$_{27}$H$_{26}$N$_2$O$_4$: C, 73.29; H, 5.92; N, 6.33%. Found: C, 73.03; H, 6.01; N, 6.21%.

EXAMPLE 60

Phenylmethyl[1-(benzo[b]thien-3-ylmethyl)-1-methyl-2-oxo-2-[(1-phenylethyl)amino]ethyl] carbamate

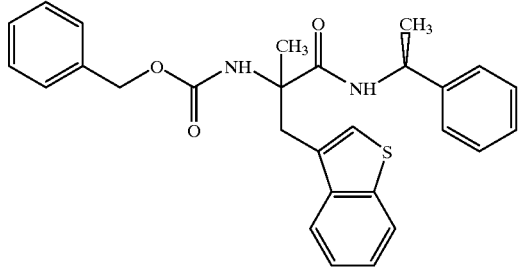

Step 1: Methyl N-CBZ-α-methyl-3-benzothiophenylalanine

A solution of methyl α-methyl-3-benzothiophenylalanine (Horwell, et al., WO9204025 A1. Mar. 19, 1992) (0.5 g, 2.0 mmol), sodium hydrogen carbonate 1:0.50 g, 6.00 mmol), dibenzyldicarbonate (0.7 g, 2.4 mmol), water (10 mL), and dioxan (10 mL) was stirred at room temperature overnight. The reaction mixture was diluted with water and ether. The organic phase was separated, washed with water, dried over MgSO$_4$, filtered, and evaporated to dryness. Purification by column chromatography eluting with 2% ethyl acetate in dichloromethane gave an oil (0.6 g, 78%);

NMR (300 MHz, CDCl$_3$): δ 1.68 (3H, s); 3.48 (1H, d, J=14.5 Hz); 3.60–3.75 (4H, m); 5.05–5.20 (2H, m); 5.53 (1H, bs); 6.94 (1H, s); 7.20–7.40 (7H, m); 7.65–7.75 (1H, m); 7.80–7.85 (1H, m); Analysis calculated for C$_{21}$H$_{21}$NO$_4$S: C, 65.78; H, 5.52; N, 3.65%. Found: C, 65.85; H, 5.50; N, 3.49%.

Step 2: N-CBZ-α-methyl-3-benzothiophenylalanine

A solution of methyl N-CBZ-α-methyl-3-benzothiophenylalanine (0.6 g, 1.57 mmol), lithium hydroxide hydrate (0.14 g, 3.33 mmol) in water (20 mL), and dioxan (20 mL) was stirred at room temperature overnight. The reaction mixture was diluted with water, washed with ether, acidified with 1N hydrochloric acid, and extracted with ethyl acetate three times. The combined extracts were washed with water, dried over magnesium sulphate, filtered, and evaporated to dryness. Crystallization from ether/hexane gave colorless crystals 0.48 g (83%);

mp 133–135° C.; NMR (300 MHz, CDCl$_3$): δ 1.28 (3H, s); 3.27 (1H, d, J=14.4 Hz); 3.59 (1H, d, J=14.4 Hz); 5.02 (1H, d, J=12.6 Hz); 5.08 (1H, d, J=12.3 Hz); 7.25–7.40 (8H, m); 7.75 (1H, d, J=7.9 Hz); 7.90–8.00 (1H, m); 12.6 (1H, s); Analysis calculated for C$_{20}$H$_{19}$NO$_4$S: C, 65.02; H, 5.15; N, 3.79%. Found: C, 64.99; H, 5.15; N, 3.80%.

Step 3: Phenylmethyl[1-(benzo[b]thien-3-ylmethyl)-1-methyl-2-oxo-2-(1-phenylethyl)amino]ethyl]-carbamate To a solution of N-CBZ-α-methyl-3-benzothiophenylalanine (0.12 g, 0.33 mmol) in ethyl acetate (10 mL) was added hydroxybenzotriazole hydrate (0.055 g, 0.36 mmol) and followed by dicyclohexylcarbodiimide (0.072 g, 0.35 mmol). After stirring at room temperature for 15 minutes, the mixture was filtered and (S)-sec-phenylethylamine (0.051 g, 0.42 mmol) in ethyl acetate was added to the filtrate. After stirring at room temperature overnight, the mixture was diluted with ethyl acetate and washed with saturated sodium hydrogen carbonate solution, 1N hydrochloric acid solution and water. The solution was dried over magnesium sulphate, filtered, and evaporated to dryness. Purification by column chromatography eluting with dichloromethane/ethyl acetate 98:2 and crystallization from ether gave colorless crystals (0.09 g, 58%); mp 147–150° C.;

NMR (300 MHz, DMSO-$d_6$): δ 1.20–1.40 (6H, m); 3.30–3.60 (2H, m); 4.85–4.95 (1H, m); 5.05 (2H, s); 7.00–7.40 (14H, m); 7.75–7.90 (1H, m); 7.90–7.95 (1H, m); 8.0 and 8.1 (1H, two d).

EXAMPLE 61

Phenylmethyl[R-(R*,R*)]-[1-(4,5-dihydro-4-phenyl-2-thiazoly-1)-2-(1H-indol-3-yl)-1-methylethyl] carbamate

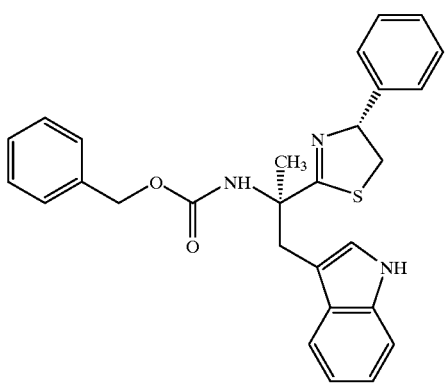

A solution of Z-α-Me-R-tryphophanyl-R-phenyl-glycinol (0.14 g, 0.30 mmol) in toluene (20 mL) was treated with Lawesson's reagent (0.2 g, 0.5 mmol) and the mixture heated at reflux for 90 minutes. The crude reaction mixture was loaded onto a silica gel column and eluted with $CH_2Cl_2$, then $Et_2O$. Further purification was then carried out using reverse phase silica gel and 85% MeOH in $H_2O$ as eluant to give the product as a white foam (0.08 g, 57%); mp 64–66° C.;

$[α]_D^{20}$=-3° (c=0.25, MeOH); IR (film): 3391, 1715, 1617, 1496, 1456 cm$^{-1}$; NMR (DMSO-$d_6$): δ 1.41 (3H, s); 2.94 (1H, br.t); 3.30 (1H, obscured by $H_2O$); 3.54 (1H, d, J=13.9 Hz); 3.71 (1H, br.t); 5.09 (2H, m); 5.46 (1H, m); 6.92 (1H, t, J=7.1 Hz); 7.00–7.39 (13H, m); 7.53 (1H, d, J=7.8 Hz); 7.58 (1H, br.s); 10.92 (1H, br.s); Analysis calculated for $C_{28}H_{27}N_3O_2S.0.25H_2O$: C, 70.93; H, 5.85; N, 8.86%. Found: C, 70.93; H, 5.73; N, 8.84%.

EXAMPLE 62

(See Scheme X)

Phenylmethyl[1-(cyanomethyl)-1-(1H-indol-3-ylmethyl)-2-oxo-2-[(1-phenylethyl)amino]-ethyl] carbamate

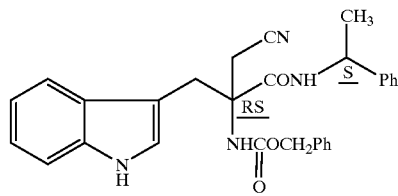

Step 1

RS-Tryptophanmethylester (2.03 g, 9.30 mmol) was stirred and dissolved in formic acid (15 mL) at room temperature. To this was added acetic anhydride (4.4 mL, 46.5 mmol) in one portion and the mixture stirred for 2.5 hours. The solution was poured into water (100 mL) and the mixture neutralized by the addition of $Na_2CO_3$. The product was extracted into EtOAc (2×100 mL) and the combined extracts washed with saturated $NaHCO_3$ solution (50 mL) and once with brine (50 mL). The EtOAc solution was dried over $MgSO_4$, filtered, and the solvent removed in vacuo to give the product as a syrup. This was crystallized from 50% EtOAc/50% n-hexane as a white solid 11.55 g, 68%); mp 113–119° C.;

IR (film): 3370, 2920, 1740, 1672, and 1212 cm$^{-1}$; NMR (CDCl$_3$): δ 3.29–3.41 (2H, m, C$\underline{H}_2$ indole); 3.71 (3H, s, CO$_2$C$\underline{H}_3$); 5.00–5.05 (1H, m, CH$_2$C$\underline{H}$); 6.13 (1H, b, N $\underline{H}$CHO); 6.98 (1H, s, indole-H$_2$); 7.09–7.21 (2H, m, indole-H$_5$H$_6$); 7.35 (1H, d, J=8.0 Hz indole-H$_7$); 7.53 (1H, d, J=7.8 Hz, indole-H$_4$); 8.14 (1H, s, NHC$\underline{H}$O); 8.20 (1H, b, indole-N $\underline{H}$).

Step 2

N-Formyl-RS-tryptophanmethylester (1.50 g, 6.09 mmol) was stirred and dissolved in anhydrous DMF (20 mL) and cooled in an ice bath. 4-Dimethylaminopyridine (0.075 g, 0.61 mmol) was added followed by dropwise addition of ditertbutyldicarbonate (1.33 g, 6.09 mmol) in anhydrous DMF (20 mL) added over 1 hour. The cold solution was stirred for 18 hours with slow rewarming to room temperature. The mixture was poured into water (300 mL) and extracted with $Et_2O$ (3×100 mL). The combined $Et_2O$ extracts were washed with water (3×100 mL), dried over $MgSO_4$, filtered and the solvent removed in vacuo. The residue was purified by chromatography on silica using 50% n-hexane/50% EtOAc as eluant giving the product as a white solid (1.71 g, 81%); mp 61–62° C.;

IR (film): 3306, 2979, 1733, 1688, 1454, 1371, and 1158 cm$^{-1}$; NMR (CDCl$_3$): δ 1.66 (9H, s,

); 3.20–3.34 (2H, m, C$\underline{H}_2$ indole); 3.71 (3H, s, CO$_2$C$\underline{H}_3$); 4.98–5.04 (1H, m, CH$_2$C$\underline{H}$CO$_2$CH$_3$); 6.32 (1H, d, J=7.4 Hz, N$\underline{H}$CHO); 7.20–7.33 (2H, m, indole-H$_5$H$_6$); 7.39 (1H, s, indole-H$_2$); 7.48 (1H, d, J=7.9 Hz, indole-H$_4$); 8.09 (1H, d, J=8.1 Hz, indole-H$_7$); 8.18 (1H, s, NHC$\underline{H}$O).

Step 3

BOC-N-formyl-RS-tryptophanmethylester (3.25 g, 9.38 mmol) was stirred and dissolved in $CH_2Cl_2$ (75 mL) and cooled in an ice bath. Et₃N (7.84 mL, 56.28 mmol) was added followed by a solution of triphosgene (1.02 g, 3.44 mmol) in CH₂Cl₂ (25 mL) added dropwise over 45 minutes. The cold solution was stirred for 3 hours with slow rewarming to room temperature. The CH₂Cl₂ solution was then washed with 5% citric acid solution (3×25 mL), saturated NaHCO₃ solution (25 mL) and brine (25 mL), dried over MgSO₄, filtered, and the solvent removed in vacuo. The residue was purified by chromatography on silica using 67% n-hexane/33% EtOAc as eluant giving the product as an off-white solid (2.26 g, 73%); mp 90–91° C.;

IR (film): 2980, 2149, 1760, 1733, 1454, 1372, 1157, and 1088 cm⁻¹; NMR (CDCl₃): δ 1.67 (9H, s,

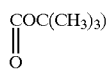

; 3.28 (1H, dd, J=14.7 and 8.0 Hz, CHH indole); 3.41 (1H, dd, J=14.7 and 4.9 Hz, CHH indole); 3.79 (3H, s, CO₂CH₃); 4.54–4.58 (1H, m, CH₂CHCO₂CH₃); 7.23–7.36 (2H, m, indole-H₅H₆); 7.50 (1H, d, J=7.8 Hz, indole-H₄); 7.59 (1H, s, indole-H₂); 8.16 (1H, d, J=8.2 Hz, indole-H₇).

Step 4

1,3-Dimethyl-3,4,5-tetrahydro-2(1H)-pyrinidinone (DMPU) (0.121 mL, 1.0 mmol) was added to a stirred solution of the isonitrile (0.328 g, 1.0 mmol) in anhydrous THF (10 mL) at −78° C. To this was added lithiumhexamethyldisilazide (1.1 mL, 1.0 mmol, 1.1 mmol) and the mixture stirred for 30 minutes. Bromoacetonitrile (0.077 mL, 1.1 mmol) was added and the mixture stirred for 1 hour at −78° C. and then at room temperature for 1.5 hours. The mixture was poured into water (25 mL) and extracted with Et₂O (2×25 mL), the combined extracts washed once with brine (25 mL), the Et₂O dried over MgSO₄, filtered, and the solvent removed in vacuo. The residue was purified by chromatography on silica using 75% n-hexane/25% EtOAc as eluant giving the product as a white solid (0.315 g, 86%); mp 92–93° C.;

IR (film): 2981, 1737, 1454, 1371, 1259, and 1156 cm⁻¹; NMR (CDCl₃): δ 1.68 (9H, s, CO₂C(CH₃)₃); 2.9 (1H, d, J=16.7 Hz, indole CHH); 3.09 (1H, d, J=16.8 Hz indole C HH); 3.47 (2H, d, J=3.7 Hz, CH₂CN); 3.76 (3H, s, CO₂C H₃); 7.24–7.37 (2H, m, indole-H₅H₆); 7.51 (1H, d, J=7.6 Hz, indole-H₄); 7.62 (1H, s, indoles-H₂); 8.15 (1H, d, J=8.1 Hz, indole-H₇); Analysis calculated for C₂₀H₂₁N₃O₄: C, 65.38; H, 5.76; N, 11.44%. Found: C, 65.23; H, 5.90; N, 11.36%.

Step 5

4.7 M HCl in 1,4-dioxan (1.0 mL, 4.7 mmol) was added to a stirred solution of the isonitrile (0.413 g, 1.12 mmol) in EtOAc (10 mL) cooled to 5° C. To this mixture was added water (1.0 mL) and the solution stirred at room temperature for 1 hour. The solvents were removed in vacuo and the residual solid partitioned between saturated NaHCO₃ solution (10 mL) and EtOAc (2×25 mL). The combined EtOAc extracts were washed once with brine (25 mL), dried over MgSO₄, filtered, and the solvent removed in vacuo. The residue was purified by chromatography on silica using 50% n-hexane/50% EtOAc as eluant giving the product as a syrup (0.301 g, 75%).

IR (film): 3380, 2979, 2256, 1734, 1454, 1370, 1258, 1157 cm⁻¹; NMR (CDCl₃): δ 1.67 (9H, s,

1.88 (2H, bs, NH₂); 2.74 (1H, d, J=16.5 Hz, CHHCN); 2.89 (1H, d, J=16.4 Hz, CHHCN); 3.12 (1H, d, J=14.3 Hz, indole CHH); 3.25 (1H, d, J=14.2 Hz, indole CHH); 3.69 (3H, s, CO₂CH₃); 7.22–7.35 (2H, m, indole-H₅H₆); 7.46 (1H, s, indole-H₂); 7.52 (1H, d, J=7.6 Hz, indole-H₄); 8.13 (1H, d, J 8.1 Hz, indole-H₇); Analysis calculated for C₁₉H₂₃N₃O₄.0.3H₂O: C, 63.85; H, 6.49; N, 11.76%. Found: C, 63.82; H, 6.64; N, 11.49%.

Step 6

The amine (0.561 g, 1.57 mmol) was stirred and dissolved in 1,4-dioxan (10 mL) and water (0.5 mL) added. Na₂CO₃ (0.832 g, 7.85 mmol) was added followed by benzylchloroformate (0.448 mL, 3.14 mmol) and the reaction stirred at room temperature for 1 hour. The 1,4-dioxan was removed in vacuo and the residue partitioned between EtOAc (50 mL) and brine (2×25 mL). The EtOAc solution was dried over MgSO₄, filtered, and the solvent removed in vacuo. The residue was purified by chromatography on silica using 67% n-hexane/33% EtOAc as eluant to give the product as a syrup (0.662 g, 86%);

IR (film): 3342, 2929, 2253, 1732, 1454, 1372, 1156, 1089 cm⁻¹; NMR (CDCl₃): δ 1.66 (9H, s,

3.24–3.34 (2H, m, CH₂CN); 3.47–3.62 (2H, m, CH₂ indole); 3.67 (3H, s, CO₂CH₃); 5.14 (2H, s, PHCH₂OCO); 5.78 (1H, s, NHCOO); 7.15–7.20 (1H, m, indole); 7.28–7.43 (12H, m, Ar); 8.10 (1H, d, J=8.4 Hz, indole-H₇); Analysis calculated for C₂₇H₂₉N₃O₆: C, 65.97; H, 5.95; N, 8.55%. Found: C, 65.72; H, 6.01; N, 8.29%

Step 7

The BOC protected ester (0.119 g, 0.24 mmol) was stirred and dissolved in CH₂Cl₂ (2 mL) at room temperature. Trifluoroacetic acid (1.0 mL) was added and the mixture stirred at room temperature for 2 hours. The solvents were removed in vacuo to give the product as a syrup which formed a foam out of Et₂O (0.078 g, 87%);

IR (film): 3358, 2254, 1718, 1457 cm⁻¹; NMR (CDCl₃): δ 3.27 (1H, d, J=6.2 Hz, CHHCN); 3.32 (1H, d, J=8.8 Hz, CHHCN); 3.53–3.63 (2H, m, CH₂ indole); 3.70 (3H, s, CO₂CH₃); 5.11 (1H, d, J=12.1 Hz, OCHHPh); 5.21 (1H, d, J=12.1 Hz, OCHHPh); 5.87 (1H, s, NHCOO); 7.22–7.45 (10H, m, indole, C₆H₅); 8.17 (1H, d, J=8.2 Hz, indole-NH);

Step 8

LiOH-H₂O (0.040 g, 0.95 mmol) was added to a stirred solution of the methylester (0.070 g, 0.19 mmol) in THF:H₂O (4 mL, 3:1 mixture) at room temperature. The mixture was stirred at room temperature for 16 hours and the THF removed in vacuo. The residue was diluted with water (10 mL) and extracted once with Et₂O (10 mL). The aqueous solution was made pH 4 with 5% citric acid solution and the product extracted into EtOAc (3×10 mL). The combined EtOAc extracts were dried over MgSO₄, filtered, and the solvent removed in vacuo giving the product as a foam (0.045 g, 65%);

IR (film): 3401, 2586, 1712 cm⁻¹; NMR (CDCl₃): δ 3.25–3.37 (3H, m, CH₂CN, CHH indole); 3.54–3.59 (1H, m, CHH indole); 5.05 (1H, d, J=12.3 Hz, OCHHPh); 5.14 (1H, d, J=12.1 Hz, OCHHPh); 5.76 (1H, b, NHCOO); 6.89 (1H, s, indole-H₂); 7.02–7.16 (2H, m, indole-H₅H₆); 7.28–7.31 (6H, m, indole, C₆H₅); 7.58 (1H, d, J=7.7 Hz, indole); 8.24 (1H, s, indole-NH);

Step 9

N,N'-dicyclohexylcarbodiimide (0.028 g, 0.138 mmol) was added to a stirred solution of the acid (0.045 g, 0.125 mmol) and 1-hydroxybenzotriazole monohydrate (0.023 g, 0.150 mmol) in EtOAc (2 mL). The mixture was stirred for 2 hours at room temperature and the N,N'-dicyclohexylurea filtered off. A solution of (S)-(−)-α-methylbenzylamine (0.023 g, 0.188 mmol) in EtOAc (0.5 mL) was added and the mixture stirred at room temperature for 21 hours. The mixture was filtered and diluted with EtOAc (25 mL) and the EtOAc solution washed with 5% citric acid solution (2×10 mL), once with saturated NaHCO₃ solution (10 mL), and once with brine (10 mL). The EtOAc solution was dried over MgSO₄, filtered, and solvent removed in vacuo. The residue was purified by chromatography on silica using 67% n-hexane/33% EtOAc as eluant giving the product as a white amorphous solid (0.023 g, 40%);

IR (film): 3337, 3033, 2931, 2251, 1717, 1656, 1496, 1257 cm⁻¹; NMR (CDCl₃): δ 0.98 (1.5H, d, J=6.7 Hz, 0.5 CH₃); 1.29 (1.5H, d, J=7.4 Hz, 0.5 CH₃); 3.16–3.57 (4H, m, indole CH₂, CH₂CN); 4.82–4.95 (1H, m, PhCHNHCO); 5.01–5.19 (2H, m, CH₂Ph); 5.55 (1H, d, J=8.9 Hz, NHCOO); 6.03 (0.5H, d, J=7.3 Hz, 0.5 CONH); 6.12 (0.5H, d, J=7.7 Hz, 0.5 CONH); 6.56 (0.5H, s, 0.5 indole-H₂); 6.97–7.37 (13.5H, m, Ar); 7.54–7.61 (1H, m, Ar); 7.98 and 8.29 (1H, two s, indole-NH). Analysis calculated for C₂₉H₂₈N₄O₃: C, 72.48; H, 5.87; N, 11.66%. Found: C, 72.29; H, 5.97; N, 11.48%.

EXAMPLE 63

Carbamic acid, [1-(1H-indol-3-ylmethyl)-1-methyl-2-oxo-2-[(1-phenylethyl)amino]ethyl]-, 2-benzofuranylmethyl ester, [R-(R*,S*)]

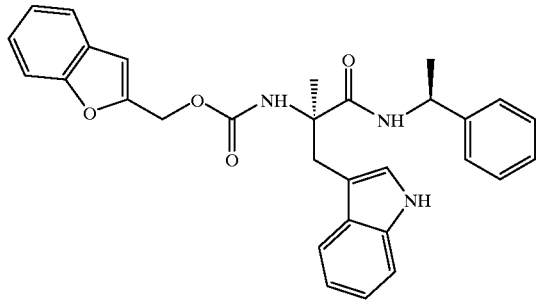

Step 1

To a stirred solution of 2-benzofuranylmethanol (Garter R, *J Am Chem Soc* 1951;73:4400) (1.48 g, 10 mmol) and 4-nitrophenylchloroformate (2.01 g, 10 mmol) in CH₂Cl₂ (50 mL, a) at 0° C. was added dropwise a solution of pyridine (0.79 g, 10 mmol) in CH₂Cl₂ (10 mL). The reaction mixture was allowed to warm to room temperature overnight. The solvent removed under reduced pressure and the residue taken up between EtOAc (50 mL) and 10% citric acid solution (50 mL). The organic phase was washed successively with 10% citric acid solution (2×50 mL), H₂O (50 mL), saturated NaHCO₃ solution (5×50 mL), brine (50 mL), dried (MgSO₄), filtered, and solvent removed under reduced pressure. The product was then recrystallized from Et₂O to give pure carbonate (1.80 g, 58%);

mp 90.5–92.5° C.; ¹H NMR (CDCl₃): δ 5.41 (2H, s, CH₂O); 6.90 (1H, s, benzofuran C3-H); 7.21–7.42 (2H, m, ArH); 7.39 (2H, d, 9.2 Hz, ArH's meta to NO₂); 7.52 (1H, d, 7.8 Hz, ArH); 7.60 (1H, d, 7.1 Hz, ArH); 8.28 (2H, d, 9.2 Hz, ArH's ortho to NO₂); IR (film): 3119, 1770, 1617, 1594, 1524 cm⁻¹; MS m/e (CI) 313; Analysis calculated for C₁₆H₁₁NO₆ (C,H,N).

Step 2

To a stirred solution of the carbonate (185 mg, 0.6 mmol) and α-methyltryptophanyl-1-phenethylamide (160 g, 0.5 mmol) in DMF (5 mL) was added 4-dimethylaminopyridine (61 mg, 0.5 mmol) and the mixture left to stir overnight at room temperature. The solvent was removed at 60° C. under reduced pressure, the residue taken up in EtOAc (100 mL) and washed successively with 10% citric acid solution (3×30 mL), H₂O (30 mL), 1N NaOH (5×30 mL), brine (2×50 mL), dried (MgSO₄), filtered, and the solvent removed under reduced pressure. The residue was then purified by chromatography on reverse phase silica eluting with 35% H₂O in MeOH. Crystallization from Et₂O gave pure product (140 mg, 56%); mp 103–111° C.;

¹H NMR (CDCl₃): δ 1.31 (3H, d, 6.9 Hz, CHCH₃); 1.63 (3H, s, CCH₃); 3.25 (1H, d, 14.8 Hz, CHH-indole); 3.47 (1H, d, 14.8 Hz, CHH-indole); 4.95–5.05 (1H, m, NHCHCH₃); 5.14 and 5.21 (each 1H, each d, 13.2 Hz, CHHO); 5.41 (1H, s, OCONH); 6.30–6.35 (1H, bd, CONHCH); 6.74 (1H, s, benzofuran C3-H); 6.78 (1H, d, 2.3 Hz, indole C2-H); 7.05–7.33 (10H, m, ArH); 7.45 (1H, d, 8.4 Hz); 7.52–7.58 (2H, m, ArH); 7.85 (1H, s, indole NH);

[α]_D=+17.6° C. (c=0.5, 21° C., MeOH); IR (film): 3334, 1715, 1651 cm⁻¹; MS m/e (FAB) 496.3 (M⁺+H); Analysis calculated for C₃₀H₂₉N₃O₄ (C,H,N).

EXAMPLE 64

Carbamic acid, [1-(1H-indol-3-ylmethyl)-1-methyl-2-oxo-2-[(1-phenylethyl)amino]ethyl]-, benzo[b]thien-2-yl-methyl ester, [R-(R*,S*)]-

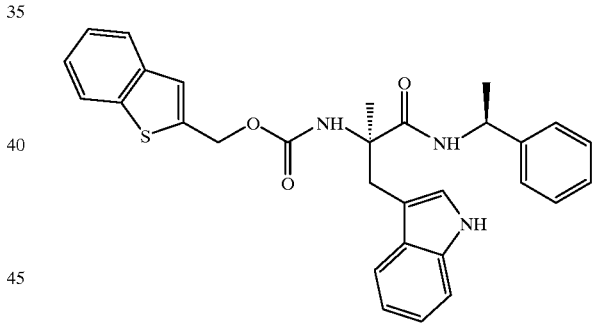

Step 1

Method as for Example 63 using benzo[b]thiophene-2-methanol (Blicke F F, Sheets D G. *J Am Chem Soc.* 1949;71:2856) (1.64 g, 10 mmol). On removal of ethylacetate under reduced pressure, a crystalline solid formed. This was washed with ether to give carbonate (1.78 g, 54%); mp 119–121.5° C.;

¹H NMR (CDCl₃): δ 5.54 (2H, s, CH₂O); 7.34–7.45 (3H, m, ArH); 7.39 (2H, d, 9.1 Hz, ArH's meta to NO₂); 7.74–7.90 (2H, m, ArH); 8.28 (2H, d, 9.2 Hz, ArH's ortho to NO₂); IR (film): 3083, 1763, 1616, 1593, 1523, 1349, 1214, 860 cm⁻¹; MS m/e (CI) 329; Analysis calculated for C₁₆H₁₁NO₅S (C,H,N,S).

Step 2

Method as for Example 63 using 198 mg (0.6 mmol) of carbonate. The crude product was purified using normal phase silica eluting with 40% EtOAc in hexane. Crystallization from Et₂O gave pure product (236 mg, 92%); mp 146–150° C.;

¹H NMR (CDCl₃): δ 1.28 (3H, d, 6.9 Hz, CHCH₃); 1.64 (3H, s, CCH₃); 3.25 (1H, d, 14.8 Hz, CHH-indole); 3.47 (1H, d, 14.8 Hz, CHH-indole); 4.95–5.05 (1H, m, NHCHCH₃); 5.27 (1H, d, 13.0 Hz, CHHO); 5.34 (1H, d, 13.1 Hz, CHHO); 5.42 (1H, s, OCONH); 6.28–6.35 (1H, bd, CONHCH); 6.78 (1H, s, indole C₂-H); 7.05–7.35 (11H, m, ArH); 7.58 (1H, d, 7.9 Hz, indole C₄-H); 7.70–7.80 (2H, m, ArH); 7.89 (1H, s, indole NH); [α]_D=+18° C. (c=0.5, 19° C., MeOH); IR (film): 3344, 1714, 1651, 1494, 1456, 1249, 1128, 1067, 744 cm⁻¹; MS m/e (FAB) 512.2 (M⁺+H); Analysis calculated for C₃₀H₂₉N₃O₃S (C,H,N,S).

EXAMPLE 65

[2-(1H-Indol-3-yl)-1-methyl-1-(1-phenyl-ethyl-carbamoyl)-ethyl]-carbamic acid 2-fluoro-5-methyl-benzyl ester

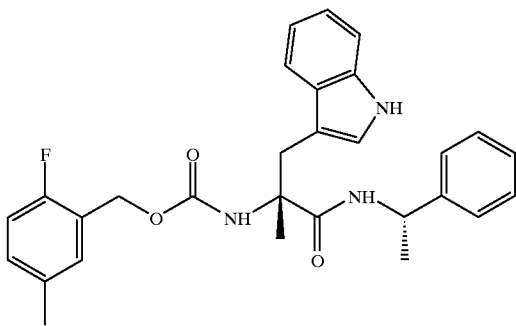

Step 1

A solution of 2-fluoro-5-methylbenzoic acid (2 g, 13 mmol) in THF (30 mL) was added slowly to a stirred suspension of NaBH₄ (593 mg, 15.6 mmol) in THF (30 mL) at room temperature under nitrogen. The mixture was stirred until effervescence ceased, before iodine was added slowly (1.65 g, 6.5 mmol) to the reaction mixture. The reaction mixture was stirred for a further 72 hours during which time an extra equivalent each of NaBH₄ and iodine were added to cause the reaction to go to completion. 2 M HCl (5 mL) was carefully added to the reaction mixture under nitrogen. Ether was then added and the organic phase was separated from the aqueous phase. This was washed with NaHCO₃(aq), water, dried (MgSO₄) and concentrated in vacuo. The residue was purified by silica gel flash chromatography, eluting with a gradient of hexane to hexane:EtOAc (9:1) to provide the alcohol as a clear oil (1.42 g, 78% yield);

¹H NMR (CDCl₃): δ 2.28 (3H, s, CH₃); 2.37 (1H, Bs, OH); 4.65 (2H, d, J=4.8 Hz, CH₂OH); 6.86–6.91 (1H, m, ArH); 6.99–7.03 (1H, m, ArH); 7.15–7.17 (1H, m, ArH); IR (film): 3346, 2926 (sm), 2886 (sm), 1501, 1457 (sm), 1247, 1228, 1205, 1140, 1121, 1042, 1020, 814 cm⁻¹; MS m/e (CI) M=140;

Step 2

The alcohol was converted to the carbonate via the method used for Example 63;

¹H NMR (CDCl₃): δ 2.32 (3H, s, CH₃); 5.31 (2H, s, CH₂O); 6.96–7.0 (1H, m, ArH of F-Ph); 7.13–7.16 (1H, m, ArH of F-Ph); 7.21–7.23 (1H, m, ArH of F-Ph); 7.35–7.39 (2H, m, 2ArH of P-NO₂Ph); 8.22–8.27 (2H, m, 2ArH of p-NO₂Ph); IR (film): 1767, 1617 (sm), 1594 (sm), 1525, 1504, 1348, 1210, 1164, 862 cm⁻¹; MS m/e (CI) 306=M+H⁺.

Step 3

The carbonate (366 mg, 1.2 mmol), the α-methyl tryptophonyl-1-phenethylamide (385 mg, 1.2 mmol) and dimethylaminopyridine (147 mg, 1.2 mmol) were stirred in DMF (100 mL) at room temperature overnight. The reaction mixture was taken up in EtOAc and washed with NaHCO₃ (aq), Na₂CO₃ (aq), 1N HCl, dried (MgSO₄) and concentrated in vacuo. The residue was purified by flash chromatography on silica gel eluting with 7:3 hexane:EtOAc to give 9 (iii) as a white solid (0.195 g, 77%); mp 104–106° C.;

¹H NMR (CDCl₃): 1.28 (3H, d, J=7.2 Hz, NHCHCH₃); 1.60 (3H, s, αMe); 2.26 (3H, s, Ph-CH₃); 3.24 (1H, d, J=14.8 Hz, CHH indole); 3.45 (1H, d, J=14.8 Hz, CHHindole); 4.95–5.03 (1H, m, NHCHCH₃; 5.06 and 5.12 (2H, 2× d, J=12.5 and 12.0 Hz, CH₂OCONH 5.3–5.4 (1H, m, OCONH); 6.34 (1H, bd, J=7.8 Hz, CONHCH); 6.79–7.32 (12H, m, 12 ArH); 7.56 (1H, d, J=8.1 Hz, ArH); 7.90–7.95 (1H, Bs, NHindole); [α]_D^{23.2° C.}=+7.74° C. (C=0.155 g 100 mL⁻¹, MeOH); IR (film): 3334, 2927, 1715, 1652, 1505, 1456, 1251, 1072, 743 cm⁻¹; MS m/e (FAB): 488.3=M+H⁺; Analysis calculated for C₂₉H₃₀FN₃O₃ (C,H,N).

EXAMPLE 66

Carbamic acid, [1-(1H-indol-3-ylmethyl)-1-methyl-2-oxo-2-[[1-(4-pyridinyl)ethyl]amino]ethyl]-, 2-benzofuranyl-methyl ester, monohydrochloride, [R-(R*,S*)]

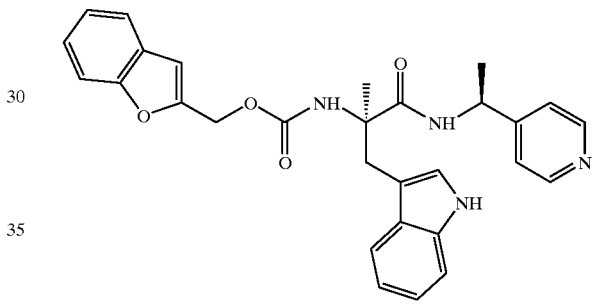

Step 1

To a suspension of lithium aluminum hydride (2.82 g, 63 mmol) in dry THF (150 mL) at −50° C. under nitrogen was added dropwise a solution of benzofuran-2-carboxylic acid (10.2 g, 63 mmol) in THF (100 mL). The reaction mixture was allowed to warm to room temperature and stirred for 16 hours. 1N HCl was added slowly with cooling (cardice-acetone bath) and the resulting solution was washed with 1N HCl, NaHCO₃(aq), dried (MgSO₄) and the solvent removed in vacuo. The residue was purified by flash chromatography on silica eluting with a mixture of hexane:EtOAc (1:1) to give the alcohol as a yellow oil (7.2 g, 77%);

¹H NMR (CDCl₃): δ 2.68 (1H, s, OH); 4.70 (2H, s, CHHOH); 6.58 (1H, s, ArH3); 7.15–7.27 (2H, m, ArH); 7.42 (1H, d, 8.1 Hz, ArH); 7.48–7.51 (1H, m, ArH); Analysis calculated for C₉H₈O₂ (C,H,N).

Step 2

To a stirred solution of the alcohol from Step 1 (8.58 g, 58 mmol) and pyridine (4.82 mL, 58 mmol) in CH₂Cl₂ (150 mL) at 10° C. was added dropwise a solution of p-nitrophenyl chloroformate (14 g, 70 mmol) in CH₂Cl₂ (150 mL). The reaction mixture was allowed to warm to room temperature and stirred for 18 hours. The solvent was removed in vacuo and the residue taken up in EtOAc, washed with 1N HCl, NaHCO₃(aq), dried (MgSO₄) and concentrated in vacuo. The resultant yellow solid was purified using hexane:ether (9:1) as eluant to give the carbonate as a cream solid (9.8 g, 54%);

IR (film): 3119, 1770, 1617, 1594, 1524, 1346, 1251, 1213, 862, 753 cm$^{-1}$; mp 90.5–92.5° C.; $^1$H NMR (CDCl$_3$): δ 5.41 (2H, s, CHHO); 6.90 (1H, s, H2 of benzofuran); 7.21–7.42 (2H, m, ArH); 7.39 (2H, d, 9.2 Hz, H2, H6 of phenyl); 7.52 (1H, d, 7.8 Hz, ArH); 7.60 (1H, d, 7.1 Hz, Ar H); 8.28 (2H, d, 9.2 Hz, H3, H5, of phenyl); Analysis calculated for C$_{16}$H$_{11}$NO$_6$ (C,H,N).

Step 3

The mixed carbonate from Step 2 (7 g, 22 mmol), (R)α-methyltryptophan, methyl ester (5.2 g, 22 mmol), and dimethylaminopyridine (2.7 g, 22 mmol) were stirred in DMF (60 mL) at room temperature overnight. The reaction mixture was taken up in ether, washed with NaCO$_{3(aq)}$, 1N HCl, dried (MgSO$_4$) and concentrated in vacuo. The residue was purified by flash chromatography on silica gel eluting with hexane:EtOAc (7:3) to give the urethane as a yellow sticky solid (8.57 g, 96%);

$^1$H NMR (CDCl$_3$): δ 1.70 (3H, s, α CH$_3$); 3.36 (1H, d, 14.6 Hz, CHH indole); 3.54 (1H, bd, 13.9 Hz, CHH indole); 3.67 (3H, s, CO$_2$CH$_3$); 5.17 (1H, d, 13.4 Hz, CHHOCONH); 5.27 (1H, d, 13.2 Hz, CHHOCONH); 5.58 (1H, bs, OCON H); 6.78 (1H, s, ArH); 6.81 (1H, s, ArH); 7.00 (1H, t, 7.6 Hz, ArH); 7.12 (1H, t, 7.3 Hz, ArH); 7.23–7.34 (3H, m, ArH); 7.47–7.50 (2H, m, ArH); 7.81 (1H, bs, indole NH).

Step 4

To a solution of the urethane (8.57 g, 21 mmol) in THF (90 mL) was added lithium hydroxide (30 mL, 10 M), methanol (30 mL) and water (60 mL) and the reaction was stirred at room temperature for 2 days. The volatiles were removed in vacuo and the aqueous mixture was acidified with 1N HCl, and extracted with EtOAc. The organic phase was washed with water, dried (MgSO$_4$) and concentrated in vacuo to yield the acid as a yellow oil (8.23 g, 100%) which was used without further purification in the next step.

Step 5

To a solution of the acid (8.23 g, 21 mmol) in EtOAc was added dicyclohexylcarbodiimide (4.3 g, 21 mmol) followed by pentafluorophenol (3.86 g, 21 mmol) and the mixture was stirred at room temperature for 16 hours. The mixture was cooled to 0° C. for 30 minutes and the resulting precipitate of dicyclo hexylurea was removed by filtration. The filtrate was washed with 1N HCl, NaCO$_{3(aq)}$, dried (MgSO$_4$) and the solvents removed in vacuo. The residue was purified by flash chromatography on silica gel eluting with a mixture of hexane:EtOAc (9:1) to give the pentafluorophenyl ester as a cream solid (7.5 g, 64%).

IR (film): 3418, 1785, 1707, 1652, 1520, 1455, 1254 cm$^{-1}$; MS m/e (CI): 559 (M+H); $^1$H NMR (CDCl$_3$): δ 1.74 (3H, s, α CH$_3$); 3.44 (1H, d, 14.9 Hz, CHH indole); 3.66 (1H, d, 14.6 Hz, CHH indole); 5.18–5.29 (3H, m, C HHOCONH); 6.79 (1H, s, ArH); 7.0 (1H, s, ArH); 7.04 (1H, t, 7.6 Hz, ArH); 7.18 (1H, t, 7.5 Hz, ArH); 7.21–7.36 (3H, m, ArH); 7.46 (1H, d, 8.1 Hz, ArH); 7.55–7.58 (2H, m, Ar H); 8.02 (1H, bs, indole NH); Analysis calculated for C$_{28}$H$_{19}$F$_5$N$_2$O$_5$ (C,H,N).

Step 6

Hydroxyl amine sulfate (11.13 g, 68 mmol) and potassium hydroxide (7.58 g, 135 mmol) as aqueous solutions, were added in quick succession to a methanolic solution (100 mL) of 4-acetylpyridine (2.73 g, 23 mmol) and the mixture was stirred overnight. The solvent was removed and the residue was taken up in EtOAc and washed with water, dried (MgSO$_4$) and concentrated in vacuo. The resulting solid was washed with ether and dried to yield the oxime as a solid (2.25 g, 72%).

Step 7

To a solution of the oxime (2.079 g, 15.3 mmol) in methanol (50 mL) was added Pearlman's catalyst: in methanol (2 micro spatulas in 5 mL). The reaction mixture was shaken under a hydrogen pressure of 46 psi and at 30° C. in a Parr Apparatus for 18 hours. The reaction mixture was filtered through Keiselguhr and the filtrate concentrated in vacuo to yield a racemic mixture of the free amine. The amine was taken up in methanol (5 mL) and one equivalent of (S)-tartaric acid (2.3 g, 15.3 mmol) in H$_2$O (3 mL) was added. The tartrate salt was filtered off and recrystallized in aqueous methanol twice to yield the (S)(S) tartrate salt of the amine homochirally pure (H$_2$O, C=0.625 g 100 mL$^{-1}$). The tartrate salt of the amine ([s] [s]) was taken up in water, basified to pH 14 and re-extracted with EtOAc. The organic layer was dried and concentrated in vacuo to yield the free amine;

$[α]_D^{20.6}$=23.12 (EtOH). (*J Am Chem Soc* 95:7525 (1973))

Step 8

The pentafluorophenyl ester from Step 5 (335 mg, 0.6 mmol) and the amine from Step 7 (73 mg, 0.6 mmol) were stirred at room temperature in DMF (80 mL) for 24 hours. The reaction mixture was washed with NaHCO$_{3(aq)}$, brine, dried (MgSO$_4$) and concentrated in vacuo. The residue was purified by silica gel flash chromatography, eluting with a gradient of hexane:EtoAc (6:4) to hexane:EtoAc (2:8). The amide was obtained as a white solid (165 mg, 55%); mp 198.5–199.5° C.;

$[α]_D^{21.1° C.}$=+34.62 (c=0.065 g 100 mL$^{-1}$, MeOH); IR (film): 3395, 3322, 1715, 1645, 1521, 1455, 1253, 1070 cm$^{-1}$; MS m/e (FAB): 497.3=M+H$^+$; $^1$H NMR (CDCl$_3$): δ 1.28 (3H, d, J=6.8 Hz, CHCH$_3$); 1.62 (3H, s [obscured by water peak], αCH$_3$); 3.22 (1H, d, J=14.8 Hz, CHH indole); 3.53 (1H, d, J=14.8 Hz, CHH indole); 4.91–5.00 (1H, m, NHCH Pyr); 5.17 (1H, d, J=13.4 Hz, CHHOCONH); 5.25 (1H, d, J=13.2 Hz, CHHOCONH); 5.33 (1H, s, OCONH); 6.49 (1H, bd, NHCHCH$_3$); 6.79 (2H, d, J=12 Hz, 2ArH); 7.06–7.36 (7H, m, 7ArH); 7.46 (1H, d, J=8.4 Hz, 1ArH); 7.56 (2H, d, J=8 Hz, 2ArH); 7.97 (1H, s, indole NH); 8.47 (2H, d, J=4.4 Hz, 2Ar pyridyl protons); Analysis calculated for C$_{29}$H$_{28}$N$_4$O$_4$ (C,H,N).

Step 9

To a solution of the pyridine derivative from Step 8 in EtOAc was added over one equivalent of HCl in dioxan (2 mL, 4 M) causing the hydrochloride salt to precipitate out. The salt was filtered and washed thoroughly with ether before repeated triturations with EtOAc/ether mixtures yielded the hydrochlorine salt as a white solid (0.134 g, 45%); mp 125–128° C.;

$[α]_D^{23.0° C.}$=+57.5 (c=0.08 g 100 mL$^{-1}$, MeOH); IR (film): 3270, 3060, 1710, 1660, 1614, 1505, 1455, 1362, 1251, 1070 cm$^{-1}$; MS m/e (FAB): 497.4=M+H$^+$-Cl; $^1$H NMR (DMSO): δ 1.31 (3H, s, CHCH$_3$); 1.33 (3H, s, αCH$_3$); 3.13 (1H, d, J=14.4 Hz, CHH indole); 3.33–3.38 (1H, m, CH H indole); 4.98–5.07 (1H, m, NHCHCH$_3$); 5.19 (2H, 2×d, no J value available, CH$_2$OCONH); 6.82 (1H, t$^t$, J=7.6 and 7.2 Hz, ArH); 6.95–6.97 (2H, m, 2ArH); 7.2–7.38 (4H, m, 4ArH); 7.40 (1H, d, J=8 Hz, ArH); 7.52 (1H, d, J=8.4 Hz, Ar H); 7.61 (1H, d, J=8 Hz, ArH); 7.91 (1H, d, J=5.2 Hz, ArH); 8.36 (1H, d, J=6.8 Hz, CONHCH); 8.78 (2H, d, J=5.6 Hz, H$^2$ and H$^6$ of pyridine); 10.89 (1H, s, indole NH); Analysis calculated for C$_{29}$H$_{29}$ClN$_4$O$_4$·0.85 H$_2$O (C,H,N).

EXAMPLE 67

Carbamic acid, [1-(1H-indol-3-ylmethyl)-2-[methyl-(phenylmethyl)amino]-2-oxoethyl]-, 2-benzofuranylmethyl ester, (S)-

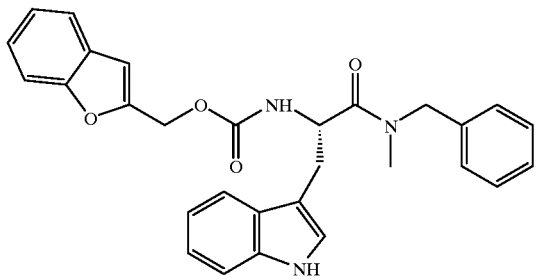

Step 1

To a stirred solution of Boc-(S)-tryptophan-O-succinimidyl ester (5.1 g, 12.6 mmol) in ethyl acetate (150 mL) at room temperature was added N-methyrlbenzylamine (1.68 g, 13.9 mmol) in ethyl acetate (50 mL) dropwise. The mixture was stirred at room temperature for 120 hours and then washed with 1N HCl (aq), NaHCO$_3$ (aq), brine, dried (MgSO$_4$), and concentrated in vacuo. The residue was chromatographed on silica gel using a gradient of 10% ether in dichloromethane to 50% ether in dichloromethane to elute the pure compound. Concentration in vacuo gave the product as a white foam (5.13 g, 95%); mp 56–58° C.;

IR (film): 3303, 1699, 1635 cm$^{-1}$; $^1$H NMR (CDCl$_3$): δ 1.41 (3H, s, t-Bu); 1.44 (6H, s, t-Bu); 2.55 (2H, s, N-Me); 2.75 (1H, s, N-Me); 3.19 (2H, d, 7 Hz, β-CH$_2$); 3.96 (0.3H, d, 16 Hz, CH$_2$Ph); 4.34 (0.3H, d, 16 Hz, CH$_2$Ph), 4.43 (1.4H, s, CH$_2$Ph); 5.00 (1H, m, α-H); 5.47 (1H, m, OCONH); 6.90–7.35 (9H, m, aromatics); 7.54 (0.33H, d, 7.5 Hz, aromatics); 7.68 (0.66H, d, 7.5 Hz, aromatics); 7.98 (0.66H, s, indole NH); 8.04 (0.33H, s, indole NH); Analysis calculated for C$_{24}$H$_{29}$N$_3$O$_3$.0.25 EtoAc C,H,N).

Step 2

Boc-(S)-tryptophan-N-methylbenzylamide (5.00 g, 12.3 mmol) was dissolved in a mixture of trifluoroacetic acid:water (9:1) (50 mL) and stirred for 45 minutes at room temperature. The solvent was removed in vacuo, the residue taken up in ethyl acetate (100 mL), washed with NaHCO$_3$ (aq), brine, dried (MgSO$_4$) and concentrated in vacuo. The residue was chromatographed on silica gel, eluting with methanol:dichloromethane (10–20%, 60 minutes) to give the product as a white solid (2.60 g, 69%);

mp 118–122° C.; IR (film): 3290, 1633 cm$^{-1}$; $^1$H NMR (CDCl$_3$): δ 2.74 (2H, s, N-Me); 2.92 (1H, s, N-Me); 2.98 (1H, m, β-CH$_2$); 3.17 (1H, m, β-CH$_2$); 3.98 (0.33H, t, 7 Hz, α-H); 4.11 (0.66H, t, 7 Hz, α-H); 4.20 (0.5H, d, 17 Hz, CH$_2$Ph); 4.44 (0.5H, d, 17 Hz, CH$_2$Ph); 4.49 (0.5H, d, 14.5 Hz, CH$_2$Ph); 4.60 (0.5H, d, 14.5 Hz, CH$_2$Ph); 7.01–7.37 (10.3H, m, aromatics); 7.59 (0.66H, d, 8 Hz, aromatics); 8.20 (1H, s, indole NH); Analysis calculated for C$_{19}$H$_{21}$N$_3$O.0.3 H$_2$O (C,H,N).

Step 3

To a stirred solution of 2-benzofuranyl p-nitrophenyl carbonate (157 mg, 0.5 mmol) in DMF (3 mL) was added (S)-tryptophan-N-methylbenzylamide (154 mg, 0.5 mmol) in DMF (2 mL) and stirring continued overnight at room temperature. The solvent was removed in vacuo and the residue taken up in ethyl acetate, washed with 1N HCl (aq), NaHCO$_3$ (aq), brine, dried (MgSO$_4$) and concentrated in vacuo. The residue was chromatographed on reverse phase silica (C18) using a gradient of 70% to 90% acetonitrile in water (0.1% TFA) to elute the pure compound (93 mg, 39%); mp 63–65° C.;

IR (film): 3296, 1714, 1634 cm$^{-1}$; MS m/e (FAB): 482.6= M+H; $^1$H NMR (CDCl$_3$): δ 2.48 (2H, m, N-Me); 2.80 (1H, m, N-Me); 3.20 (2H, m, β-CH$_2$); 3.98 (0.5H, d, 16.5 Hz, CH$_2$Ph); 4.37 (0.5H, d, 16.5 Hz, CH$_2$Ph); 4.40 (0.5H, d, 15 Hz, CH$_2$Ph); 4.47 (0.5H, d, 15 Hz, CH$_2$Ph); 5.11 (1H, m, α-H); 5.22 (2H, m, ArCH$_2$O); 5.78 (1H, m, OCONH); 6.70–7.69 (15H, m, aromatics); 7.87 (0.5H, s, indole NH); 7.95 (0.5H, s, indole NH); Analysis calculated for C$_{29}$H$_{27}$N$_3$O$_4$ (C,H,N).

EXAMPLE 68

Carbamic acid, [1-(1H-indol-3-ylmethyl)-2-[methyl-(phenylmethyl)amino]-2-oxoethyl]-, benzo[b]thien-2-ylmethyl ester, (S)-

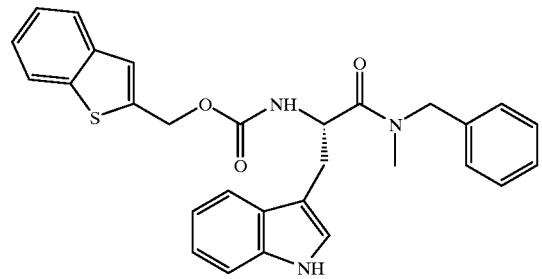

To a stirred solution of 2-benzothiophenyl p-nitrophenyl carbonate (165 mg, 0.5 mmol) in DMF (3 mL) was added (S)-tryptophan-N-methylbenzylamide (154 mg, 0.5 mmol) in DMF (2 mL) and stirring continued overnight at room temperature. The solvent w,as removed in vacuo and the residue taken up in ethyl acetate, washed with 1N HCl (aq), NaHCO$_3$ (aq), brine, dried (MgSO$_4$), and concentrate in vacuo. The residue was chromatographed on reverse-phase silica (C18) using a gradient of 70% to 90% acetonitrile in water (0.1% TFA) to elute the pure compound (72 mg, 29%); mp 64–67° C.;

IR (film): 3292, 1713, 1634 cm$^{-1}$; MS m/e (FAB): 5020.6=M+Na$^+$ $^1$NMR (CDCl$_3$): δ 2.50 (2H, m, N-Me); 2.78 (1H, m, N-Me); 3.20 (2H, m, β-CH$_2$); 3.96 (0.5H, d, 16 Hz, H$_3$CH$_2$Ph); 4.35 (0.5H, d, 16 Hz, CH$_2$Ph); 4.41 (0.5H, d, 15 Hz, CH$_2$Ph); 4.46 (0.5H, d, 15 Hz, CH$_2$Ph); 5.05 (1H, m, α-H); 5.33 (2H, m, ArCH$_2$O); 5.78 (1H, m, OCOHN); 6.80–7.83 (15H, m, aromatics); 7.86 (0.5H, s, indole NH); 7.93 (0.5H, s, indole NH); Analysis calculated for C$_{29}$H$_{27}$N$_3$O$_3$S.0.2 H$_2$O (C,H,N,S).

We claim:

1. A compound selected from the group consisting of:
   (R)-Trp (S)-NHCH(CH3)-phenyl,
   (R)-α-MeTrp (S)-NHCH(CH$_3$)-phenyl, and
   (S)-Trp N(CH$_3$)CH$_2$-phenyl.

2. A compound of formula

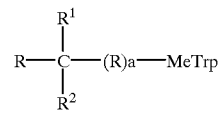

wherein R is phenyl,
pyridine, thiophene,
furan,
naphthalene,
indole,
benzofuran, or
benzothiophene each unsubstituted,
mono-, di-, or trisubstituted by
  alkyl
    hydroxy,
    alkoxy,
    $NO_2$,
    halogen,
    $NH_2$, or
    $CF_3$;
$R^1$ and $R^2$ are each independently hydrogen or alkyl of from 1 to 4 atoms; and
R and $R^2$, when joined by a bond, may form a ring.

* * * * *